(12) United States Patent
Magill

(10) Patent No.: US 8,104,190 B2
(45) Date of Patent: *Jan. 31, 2012

(54) WOOD KILN MOISTURE MEASUREMENT CALIBRATION AND METERING METHODS

(75) Inventor: Richard Magill, Cheyene, WY (US)

(73) Assignee: Signature Control Systems, Inc., Sheridan, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/683,023

(22) Filed: Jan. 6, 2010

(65) Prior Publication Data

US 2010/0171513 A1 Jul. 8, 2010

Related U.S. Application Data

(63) Continuation of application No. 11/617,910, filed on Dec. 29, 2006, now Pat. No. 7,676,953.

(51) Int. Cl.
*F26B 11/02* (2006.01)

(52) U.S. Cl. .................. 34/282; 34/396; 34/90; 705/14; 147/17; 43/132.1; 700/275; 700/150; 73/73; 73/866

(58) Field of Classification Search .................... 34/282, 34/522, 389, 396, 90, 310, 218, 242; 43/132.1; 147/17; 700/275, 150; 705/14; 144/380, 144/363; 73/73, 866
See application file for complete search history.

(56) References Cited

U.S. PATENT DOCUMENTS

| 1,567,559 | A | 12/1925 | Berchmans |
| 1,583,376 | A | 5/1926 | Berchmans |
| 1,593,890 | A | 7/1926 | Berchman |
| 2,197,823 | A | 4/1940 | Harold |
| 2,230,119 | A | 1/1941 | Fredrich |
| RE22,894 | E * | 7/1947 | Lavoie ........................ 324/76.51 |
| 2,666,897 | A | 1/1954 | Hobart |
| 2,765,219 | A | 10/1956 | Shawhan |
| 2,821,682 | A | 1/1958 | Bauer |
| 2,838,424 | A | 6/1958 | Depew |
| 2,868,673 | A | 1/1959 | Depew |

(Continued)

FOREIGN PATENT DOCUMENTS

DE 2932445 2/1981

(Continued)

OTHER PUBLICATIONS

Notice of Allowance for Canadian Patent Application No. 2,673,820, dated Apr. 8, 2011.

(Continued)

*Primary Examiner* — Stephen M. Gravini
(74) *Attorney, Agent, or Firm* — Sheridan Ross P.C.; Dennis J. Dupray

(57) ABSTRACT

A moisture metering calibration method and system for, e.g., determining the moisture lumber within a lumber drying kiln is disclosed. Calibration of moisture indicative electrical signals obtained from, e.g., moisture sensing capacitive plates spaced apart within a stack of drying lumber is performed, wherein long lengths (e.g., up to 1000 linear feet or more) of coaxial cable can be used for transmitting the signals, and effectively removing signal anomalies induced in such cabling so that accurate lumber moisture measurements result. Such extended cable lengths provides flexibility with respect to placement of electronic moisture metering equipment. This flexibility allows such equipment to be placed in an environmentally-controlled enclosure, rather than on the weather exposed exterior of a kiln whose lumber is being monitored.

11 Claims, 19 Drawing Sheets

U.S. PATENT DOCUMENTS

| | | | |
|---|---|---|---|
| 3,041,877 A | 7/1962 | Miklos | |
| 3,151,850 A | 10/1964 | Wellford | |
| 3,269,715 A | 8/1966 | Wellford | |
| 3,337,526 A | 8/1967 | Adams | |
| 3,425,267 A * | 2/1969 | Pfeiffer | 73/78 |
| 3,430,357 A * | 3/1969 | Perry | 34/403 |
| 3,440,525 A * | 4/1969 | Cardeiro | 324/438 |
| 3,448,530 A | 6/1969 | Mortensen | |
| 3,456,700 A | 7/1969 | Ahlstedt | |
| 3,510,956 A | 5/1970 | Hirth et al. | |
| 3,521,373 A | 7/1970 | Pagnozzi | |
| 3,523,243 A * | 8/1970 | Wagner | 324/669 |
| 3,593,128 A | 7/1971 | Perry | |
| 3,600,676 A | 8/1971 | Lugwig et al. | |
| 3,614,074 A | 10/1971 | Wellford | |
| 3,710,062 A * | 1/1973 | Peters, Jr. | 219/627 |
| 3,714,716 A | 2/1973 | Dedrick | |
| 3,744,147 A | 7/1973 | Pless | |
| 3,746,975 A | 7/1973 | Maltby | |
| 3,748,578 A * | 7/1973 | Ward | 324/695 |
| 3,753,092 A | 8/1973 | Ludlow et al. | |
| 3,778,705 A | 12/1973 | Maltby | |
| 3,781,671 A * | 12/1973 | Preikschat | 324/670 |
| 3,781,672 A | 12/1973 | Maltby et al. | |
| 3,791,792 A | 2/1974 | Lindsay | |
| 3,807,055 A * | 4/1974 | Kraxberger | 34/402 |
| 3,824,461 A * | 7/1974 | Preikschat | 324/666 |
| 3,879,644 A | 4/1975 | Maltby | |
| 3,887,781 A * | 6/1975 | Peters, Jr. | 219/627 |
| 3,953,783 A * | 4/1976 | Peters, Jr. | 363/124 |
| 3,985,712 A | 10/1976 | Garst | |
| 3,992,665 A * | 11/1976 | Preikschat | 324/666 |
| 4,020,785 A | 5/1977 | Palmer | |
| 4,104,584 A | 8/1978 | Miyai et al. | |
| 4,107,599 A * | 8/1978 | Preikschat | 324/689 |
| 4,151,387 A * | 4/1979 | Peters, Jr. | 219/626 |
| 4,176,464 A | 12/1979 | Randolph | |
| 4,182,794 A | 1/1980 | Smith et al. | |
| 4,213,404 A | 7/1980 | Spaulding | |
| 4,250,628 A | 2/1981 | Smith et al. | |
| 4,259,147 A | 3/1981 | Gordy | |
| 4,259,151 A | 3/1981 | Gordy | |
| 4,261,525 A | 4/1981 | Wagner | |
| 4,331,516 A | 5/1982 | Meighan | |
| 4,338,163 A | 7/1982 | Rittenhouse | |
| 4,344,142 A | 8/1982 | Diehr, II et al. | |
| 4,356,641 A | 11/1982 | Rosenau | |
| 4,373,010 A | 2/1983 | Oberley | |
| 4,373,092 A | 2/1983 | Zsolnay | |
| 4,377,783 A | 3/1983 | Wagner | |
| 4,381,250 A | 4/1983 | Rittenhouse | |
| 4,389,578 A | 6/1983 | Wagner | |
| 4,399,100 A | 8/1983 | Zsolnay et al. | |
| 4,423,371 A | 12/1983 | Senturia et al. | |
| 4,431,405 A | 2/1984 | Eatherton | |
| 4,433,286 A | 2/1984 | Capots | |
| 4,448,943 A | 5/1984 | Golba, Jr. et al. | |
| 4,496,697 A | 1/1985 | Zsolnay et al. | |
| 4,510,103 A | 4/1985 | Yamaguchi et al. | |
| 4,510,436 A | 4/1985 | Raymond | |
| 4,515,545 A | 5/1985 | Hinrichs et al. | |
| 4,546,438 A | 10/1985 | Prewitt et al. | |
| 4,551,103 A | 11/1985 | Vitale | |
| 4,551,807 A | 11/1985 | Hsich et al. | |
| 4,580,233 A | 4/1986 | Parker et al. | |
| 4,580,354 A | 4/1986 | Lindberg | |
| 4,588,943 A | 5/1986 | Hirth | |
| 4,612,802 A | 9/1986 | Clarke et al. | |
| 4,616,425 A | 10/1986 | Burns | |
| 4,620,373 A | 11/1986 | Laskowski et al. | |
| 4,621,229 A | 11/1986 | Hirth | |
| 4,676,101 A | 6/1987 | Baughman | |
| 4,683,418 A | 7/1987 | Wagner et al. | |
| 4,710,550 A | 12/1987 | Kranbuehl | |
| 4,723,908 A | 2/1988 | Kranbuehl | |
| 4,773,021 A | 9/1988 | Harris et al. | |
| 4,777,336 A | 10/1988 | Asmussen | |
| 4,777,431 A | 10/1988 | Day et al. | |
| 4,777,604 A | 10/1988 | Robinson | |
| 4,827,872 A | 5/1989 | Sommers | |
| 4,868,769 A | 9/1989 | Persson | |
| 4,881,025 A | 11/1989 | Gregory | |
| 4,896,098 A | 1/1990 | Haritonidis et al. | |
| 4,953,298 A | 9/1990 | Carter et al. | |
| 5,008,307 A | 4/1991 | Inomata | |
| 5,024,091 A | 6/1991 | Pellerin et al. | |
| 5,032,525 A | 7/1991 | Lee et al. | |
| 5,129,267 A | 7/1992 | Nicholls | |
| 5,168,681 A | 12/1992 | Ayraoetyan | |
| 5,184,077 A | 2/1993 | Day et al. | |
| 5,201,956 A | 4/1993 | Humphrey et al. | |
| 5,207,956 A | 5/1993 | Kline et al. | |
| 5,208,544 A | 5/1993 | McBrearty et al. | |
| 5,210,499 A | 5/1993 | Walsh | |
| 5,212,453 A * | 5/1993 | Koehler et al. | 324/664 |
| 5,219,498 A | 6/1993 | Keller et al. | |
| 5,223,796 A | 6/1993 | Waldman et al. | |
| 5,269,076 A | 12/1993 | Breckenridge | |
| 5,283,731 A | 2/1994 | Lalonde et al. | |
| 5,291,422 A | 3/1994 | Esztergar | |
| 5,307,679 A | 5/1994 | Ross | |
| 5,308,653 A | 5/1994 | Rondy | |
| 5,317,252 A | 5/1994 | Kranbuehl | |
| 5,325,604 A | 7/1994 | Little | |
| 5,334,941 A * | 8/1994 | King | 324/637 |
| 5,394,097 A | 2/1995 | Bechtel et al. | |
| 5,402,076 A | 3/1995 | Havener et al. | |
| 5,432,435 A | 7/1995 | Strong et al. | |
| 5,442,293 A | 8/1995 | Lange | |
| 5,453,689 A | 9/1995 | Goldfine et al. | |
| 5,459,406 A | 10/1995 | Louge | |
| 5,486,319 A | 1/1996 | Stone et al. | |
| 5,488,312 A | 1/1996 | Havener et al. | |
| 5,504,281 A * | 4/1996 | Whitney et al. | 181/286 |
| 5,507,988 A | 4/1996 | Eagan et al. | |
| 5,512,834 A * | 4/1996 | McEwan | 324/642 |
| 5,521,515 A | 5/1996 | Campbell | |
| 5,528,155 A | 6/1996 | King et al. | |
| 5,564,199 A | 10/1996 | Yamamoto et al. | |
| 5,569,591 A | 10/1996 | Kell et al. | |
| 5,585,732 A | 12/1996 | Steele et al. | |
| 5,605,290 A * | 2/1997 | Brenholdt | 241/21 |
| 5,621,391 A | 4/1997 | Elseth | |
| 5,647,364 A * | 7/1997 | Schneider et al. | 600/445 |
| 5,654,643 A | 8/1997 | Bechtel et al. | |
| 5,680,315 A | 10/1997 | Rimondi et al. | |
| 5,687,490 A | 11/1997 | Harrison | |
| 5,693,296 A | 12/1997 | Holtzapple et al. | |
| 5,694,653 A * | 12/1997 | Harald | 4/623 |
| 5,694,821 A | 12/1997 | Smith | |
| 5,716,711 A | 2/1998 | Calder et al. | |
| 5,736,197 A | 4/1998 | Gaveske | |
| 5,749,986 A | 5/1998 | Wyatt | |
| 5,752,328 A | 5/1998 | Yamamoto | |
| 5,756,975 A | 5/1998 | Harris et al. | |
| 5,775,003 A | 7/1998 | Goodwin | |
| 5,852,880 A | 12/1998 | Harrison | |
| 5,865,898 A | 2/1999 | Holtzapple et al. | |
| 5,872,447 A | 2/1999 | Hager, III | |
| 5,874,832 A | 2/1999 | Gabelich | |
| 5,892,208 A | 4/1999 | Harris et al. | |
| 5,898,309 A | 4/1999 | Becker et al. | |
| 5,911,195 A | 6/1999 | Tripp et al. | |
| 5,915,811 A | 6/1999 | DeVore et al. | |
| 5,919,242 A | 7/1999 | Greatline et al. | |
| 5,927,359 A | 7/1999 | Kersten | |
| 5,935,071 A * | 8/1999 | Schneider et al. | 600/445 |
| 5,943,789 A | 8/1999 | Yamamoto | |
| 5,950,326 A | 9/1999 | Scott | |
| 5,961,913 A | 10/1999 | Haase | |
| 5,970,624 A | 10/1999 | Moriya | |
| 5,992,048 A | 11/1999 | DeVore et al. | |
| 5,996,006 A | 11/1999 | Speicher | |
| 6,021,662 A | 2/2000 | Moulu et al. | |
| 6,023,879 A | 2/2000 | Katz et al. | |
| 6,043,308 A | 3/2000 | Tanahashi et al. | |
| 6,055,915 A | 5/2000 | Bickell et al. | |

| | | | |
|---|---|---|---|
| 6,072,890 A | 6/2000 | Savard et al. | |
| 6,114,863 A | 9/2000 | Krahn et al. | |
| 6,122,599 A * | 9/2000 | Mehta | 702/100 |
| 6,124,584 A | 9/2000 | Blaker et al. | |
| 6,138,379 A | 10/2000 | DeVore et al. | |
| 6,141,888 A | 11/2000 | Cammarata | |
| 6,178,834 B1 | 1/2001 | Cates | |
| 6,182,610 B1 | 2/2001 | Tripp et al. | |
| 6,189,393 B1 | 2/2001 | Cates | |
| 6,202,320 B1 | 3/2001 | Chow | |
| 6,229,318 B1 | 5/2001 | Suda | |
| 6,234,008 B1 | 5/2001 | Sjoblom et al. | |
| 6,235,349 B1 | 5/2001 | Grantham et al. | |
| 6,242,726 B1 | 6/2001 | Harris et al. | |
| 6,249,988 B1 | 6/2001 | Duske et al. | |
| 6,272,437 B1 | 8/2001 | Woods et al. | |
| 6,281,801 B1 | 8/2001 | Cherry et al. | |
| 6,303,166 B1 | 10/2001 | Kolbe et al. | |
| 6,313,646 B1 * | 11/2001 | Davis et al. | 324/690 |
| 6,323,659 B1 | 11/2001 | Krahn | |
| 6,327,910 B1 | 12/2001 | Beall | |
| 6,329,139 B1 * | 12/2001 | Nova et al. | 506/30 |
| 6,340,892 B1 | 1/2002 | Rynhart et al. | |
| 6,347,542 B1 | 2/2002 | Larsson et al. | |
| 6,378,408 B2 | 4/2002 | Smith | |
| 6,382,062 B1 | 5/2002 | Smith | |
| 6,411,106 B1 | 6/2002 | Holmes et al. | |
| 6,426,615 B1 * | 7/2002 | Mehta | 324/71.4 |
| 6,439,069 B1 | 8/2002 | Cates | |
| 6,447,639 B1 | 9/2002 | Warren et al. | |
| 6,466,168 B1 | 10/2002 | McEwan | |
| 6,472,885 B1 | 10/2002 | Green et al. | |
| 6,485,296 B1 | 11/2002 | Bender et al. | |
| 6,490,501 B1 | 12/2002 | Saunders | |
| 6,524,442 B2 | 2/2003 | Tanner et al. | |
| 6,525,319 B2 | 2/2003 | Meglen et al. | |
| 6,528,175 B2 | 3/2003 | Grantham et al. | |
| 6,586,483 B2 | 7/2003 | Kolb et al. | |
| 6,593,572 B2 | 7/2003 | Kelley | |
| 6,594,590 B2 | 7/2003 | Woods et al. | |
| 6,606,568 B2 | 8/2003 | Meglen et al. | |
| 6,607,619 B1 | 8/2003 | Foucht et al. | |
| 6,657,173 B2 | 12/2003 | Flugstad et al. | |
| 6,673,596 B1 * | 1/2004 | Sayler et al. | 435/288.7 |
| 6,690,320 B2 * | 2/2004 | Benway et al. | 342/124 |
| 6,691,563 B1 * | 2/2004 | Trabelsi et al. | 73/73 |
| 6,701,816 B2 | 3/2004 | Smith | |
| 6,703,847 B2 * | 3/2004 | Venter et al. | 324/663 |
| 6,708,555 B1 | 3/2004 | Lyons, Jr. et al. | |
| 6,747,461 B2 | 6/2004 | Corak et al. | |
| 6,773,545 B2 | 8/2004 | Tanner et al. | |
| 6,774,643 B2 | 8/2004 | Magill | |
| 6,784,405 B2 | 8/2004 | Flugstad et al. | |
| 6,784,671 B2 * | 8/2004 | Steele et al. | 324/640 |
| 6,784,672 B2 * | 8/2004 | Steele et al. | 324/663 |
| 6,797,660 B2 | 9/2004 | Komatsu | |
| 6,831,468 B2 | 12/2004 | Anderson et al. | |
| 6,846,446 B2 | 1/2005 | Mbachu et al. | |
| 6,855,791 B2 | 2/2005 | Van Doren et al. | |
| 6,886,618 B2 | 5/2005 | Foucht et al. | |
| 6,901,352 B2 | 5/2005 | Woods et al. | |
| 6,903,557 B2 | 6/2005 | Holmes et al. | |
| 6,905,834 B1 * | 6/2005 | Simpson et al. | 435/7.32 |
| 6,942,826 B2 | 9/2005 | Mbachu et al. | |
| 6,974,035 B2 | 12/2005 | Dai et al. | |
| 6,989,678 B2 * | 1/2006 | Venter et al. | 324/663 |
| 7,017,413 B2 | 3/2006 | Floyd et al. | |
| 7,043,970 B2 | 5/2006 | Ristea et al. | |
| 7,043,990 B2 | 5/2006 | Wang et al. | |
| 7,047,153 B2 | 5/2006 | Woods et al. | |
| 7,068,050 B2 * | 6/2006 | Steele et al. | 324/640 |
| 7,068,051 B2 | 6/2006 | Anderson | |
| 7,072,809 B2 | 7/2006 | Egermann et al. | |
| 7,078,913 B1 | 7/2006 | Pelletier | |
| 7,090,992 B2 * | 8/2006 | Simpson et al. | 435/7.32 |
| 7,128,270 B2 * | 10/2006 | Silverbrook et al. | 235/472.01 |
| 7,131,471 B2 | 11/2006 | McIntosh | |
| 7,138,810 B2 * | 11/2006 | Lesher et al. | 324/750.26 |
| 7,141,193 B2 | 11/2006 | Mbachu et al. | |
| 7,146,747 B2 | 12/2006 | Studd et al. | |
| 7,149,597 B2 | 12/2006 | Billings | |
| 7,167,773 B2 | 1/2007 | Schneider et al. | |
| 7,172,897 B2 * | 2/2007 | Blackburn et al. | 435/287.2 |
| 7,186,102 B2 | 3/2007 | Laver et al. | |
| 7,190,181 B2 * | 3/2007 | Peters et al. | 324/750.27 |
| 7,194,822 B2 | 3/2007 | Kolari | |
| 7,202,613 B2 * | 4/2007 | Morgan et al. | 315/312 |
| 7,208,286 B2 * | 4/2007 | Simpson et al. | 435/7.32 |
| 7,220,365 B2 | 5/2007 | Qu et al. | |
| 7,221,172 B2 * | 5/2007 | Dunklee | 324/754.05 |
| 7,241,322 B2 | 7/2007 | Graham | |
| 7,243,050 B2 | 7/2007 | Armstrong | |
| 7,245,985 B2 * | 7/2007 | Magill et al. | 700/198 |
| 7,246,452 B1 | 7/2007 | Roy | |
| 7,250,779 B2 * | 7/2007 | Dunklee et al. | 324/754.03 |
| 7,265,351 B2 | 9/2007 | De Villers et al. | |
| 7,286,956 B2 | 10/2007 | Floyd et al. | |
| 7,293,570 B2 | 11/2007 | Jackson | |
| 7,295,025 B2 * | 11/2007 | Lesher et al. | 324/756.03 |
| 7,319,037 B1 | 1/2008 | Albeck-Marom | |
| 7,324,904 B2 | 1/2008 | Floyd et al. | |
| 7,330,023 B2 * | 2/2008 | Schwindt et al. | 324/750.19 |
| 7,330,034 B1 | 2/2008 | Pelletier et al. | |
| RE40,156 E * | 3/2008 | Sharps et al. | 606/32 |
| 7,347,912 B2 | 3/2008 | Engel et al. | |
| 7,348,787 B2 * | 3/2008 | Harwood et al. | 324/750.14 |
| 7,352,168 B2 * | 4/2008 | Dunklee | 324/756.02 |
| 7,371,538 B2 * | 5/2008 | Simpson et al. | 435/7.32 |
| 7,373,863 B2 * | 5/2008 | O'Banion et al. | 83/63 |
| 7,383,730 B2 | 6/2008 | Huang et al. | |
| 7,385,835 B2 * | 6/2008 | Leedy | 365/114 |
| 7,423,419 B2 * | 9/2008 | Dunklee | 324/756.01 |
| 7,431,872 B2 | 10/2008 | Dostal et al. | |
| 7,433,755 B2 * | 10/2008 | Magill et al. | 700/198 |
| 7,436,170 B2 * | 10/2008 | Peters et al. | 324/750.27 |
| 7,466,403 B2 | 12/2008 | Carman et al. | |
| 7,468,155 B2 | 12/2008 | Mbachu et al. | |
| 7,468,609 B2 * | 12/2008 | Dunklee | 324/754.05 |
| 7,471,764 B2 | 12/2008 | Kaval | |
| 7,492,147 B2 * | 2/2009 | Schwindt et al. | 324/757.03 |
| 7,492,172 B2 * | 2/2009 | Stewart et al. | 324/756.02 |
| 7,498,828 B2 * | 3/2009 | Dunklee et al. | 324/756.01 |
| 7,499,171 B2 | 3/2009 | Huang et al. | |
| 7,501,810 B2 * | 3/2009 | Dunklee | 324/756.01 |
| 7,514,915 B2 * | 4/2009 | Dunklee | 324/756.01 |
| 7,518,358 B2 * | 4/2009 | Dunklee | 324/756.07 |
| 7,535,247 B2 * | 5/2009 | Andrews et al. | 324/760.01 |
| 7,539,533 B2 * | 5/2009 | Tran | 600/509 |
| 7,550,931 B2 * | 6/2009 | Lys et al. | 315/291 |
| 7,550,984 B2 * | 6/2009 | Lesher et al. | 324/755.11 |
| 7,558,622 B2 * | 7/2009 | Tran | 600/509 |
| 7,571,554 B2 | 8/2009 | Sprague | |
| 7,581,446 B2 * | 9/2009 | Troxler | 73/623 |
| 7,584,652 B2 | 9/2009 | Floyd et al. | |
| 7,585,681 B2 | 9/2009 | Hunt et al. | |
| 7,589,518 B2 * | 9/2009 | Schwindt et al. | 324/757.03 |
| 7,595,632 B2 * | 9/2009 | Harwood et al. | 324/757.03 |
| 7,605,940 B2 * | 10/2009 | Silverbrook et al. | 358/1.17 |
| 7,606,592 B2 * | 10/2009 | Becker | 455/523 |
| 7,615,837 B2 * | 11/2009 | Leedy | 257/433 |
| 7,626,379 B2 * | 12/2009 | Peters et al. | 324/750.27 |
| 7,630,847 B2 | 12/2009 | Jones et al. | |
| 7,646,029 B2 * | 1/2010 | Mueller et al. | 257/84 |
| 7,652,268 B2 | 1/2010 | Patel | |
| 7,665,226 B2 | 2/2010 | Tsuruta et al. | |
| 7,667,462 B2 | 2/2010 | Song et al. | |
| 7,676,953 B2 * | 3/2010 | Magill | 34/282 |
| 7,680,304 B2 | 3/2010 | Biernacki et al. | |
| 7,690,148 B2 | 4/2010 | Hedman | |
| 7,705,614 B2 * | 4/2010 | Troxler et al. | 324/663 |
| 7,711,938 B2 * | 5/2010 | Wise et al. | 712/300 |
| 7,715,011 B2 | 5/2010 | Huang et al. | |
| 7,748,137 B2 | 7/2010 | Wang | |
| 7,783,005 B2 | 8/2010 | Kaval | |
| 7,789,024 B2 | 9/2010 | Muirhead | |
| 7,795,390 B2 * | 9/2010 | Mori et al. | 530/350 |
| 7,814,799 B2 | 10/2010 | Tiitta et al. | |
| 7,816,002 B2 | 10/2010 | Matsuda et al. | |

| | | | | | |
|---|---|---|---|---|---|
| 7,827,889 B2* | 11/2010 | Carrier .................. 83/63 | 2008/0130562 A1* | 6/2008 | Shorty et al. ............ 370/329 |
| 7,837,932 B2 | 11/2010 | Hedman | 2008/0146890 A1* | 6/2008 | LeBoeuf et al. ........... 600/300 |
| 7,860,544 B2* | 12/2010 | Say et al. ................ 600/347 | 2008/0146892 A1* | 6/2008 | LeBoeuf et al. ........... 600/300 |
| 7,869,853 B1* | 1/2011 | Say et al. ................ 600/347 | 2008/0151795 A1* | 6/2008 | Shorty et al. ............ 370/310 |
| 7,876,115 B2* | 1/2011 | Stewart et al. ........ 324/754.07 | 2008/0151824 A1* | 6/2008 | Shorty et al. ............ 370/329 |
| 7,885,699 B2* | 2/2011 | Say et al. ................ 600/347 | 2008/0151825 A1* | 6/2008 | Shorty et al. ............ 370/329 |
| 7,940,069 B2* | 5/2011 | Andrews et al. ....... 324/755.01 | 2008/0151826 A1* | 6/2008 | Shorty et al. ............ 370/329 |
| 7,969,173 B2* | 6/2011 | Dunklee .............. 324/756.07 | 2008/0151827 A1* | 6/2008 | Shorty et al. ............ 370/329 |
| 2001/0002282 A1 | 5/2001 | Grantham | 2008/0154396 A1* | 6/2008 | Shorty et al. ............ 700/90 |
| 2001/0050629 A1* | 12/2001 | Benway et al. ............ 342/124 | 2008/0159213 A1* | 7/2008 | Shorty et al. ............ 370/329 |
| 2002/0046712 A1 | 4/2002 | Tripp et al. | 2008/0161972 A1* | 7/2008 | Magill .................. 700/275 |
| 2002/0047009 A1* | 4/2002 | Flugstad et al. ........... 219/771 | 2008/0165712 A1* | 7/2008 | Shorty et al. ............ 370/310 |
| 2002/0062545 A1 | 5/2002 | Niedermair | 2008/0170511 A1* | 7/2008 | Shorty et al. ............ 370/254 |
| 2003/0001595 A1* | 1/2003 | Steele et al. ............ 324/717 | 2008/0184856 A1 | 8/2008 | Koskovich |
| 2003/0062908 A1* | 4/2003 | Venter et al. ............ 324/661 | 2008/0187565 A1 | 8/2008 | Hill et al. |
| 2003/0079365 A1* | 5/2003 | Corak et al. ............ 34/89 | 2008/0194591 A1 | 8/2008 | Entwistle et al. |
| 2003/0117321 A1 | 6/2003 | Furse et al. | 2008/0197054 A1 | 8/2008 | Lindstrom |
| 2003/0146767 A1* | 8/2003 | Steele et al. ............ 324/640 | 2008/0213532 A1 | 9/2008 | Engel et al. |
| 2003/0205571 A1* | 11/2003 | Flugstad et al. ........... 219/497 | 2008/0227216 A1 | 9/2008 | Albeck-Marom |
| 2004/0026268 A1 | 2/2004 | Maki et al. | 2008/0243424 A1 | 10/2008 | Jones et al. |
| 2004/0028554 A1 | 2/2004 | Hedman | 2008/0283151 A1 | 11/2008 | Floyd et al. |
| 2004/0124856 A1* | 7/2004 | Venter et al. ............ 324/664 | 2008/0286557 A1 | 11/2008 | Tucker |
| 2004/0128712 A1 | 7/2004 | Jiang et al. | 2008/0295602 A1 | 12/2008 | Wallace |
| 2004/0133301 A1 | 7/2004 | Van Doren et al. | 2009/0017709 A1 | 1/2009 | Fliedner et al. |
| 2004/0157961 A1 | 8/2004 | Tullos et al. | 2009/0045258 A1 | 2/2009 | Sabeta |
| 2004/0160199 A1* | 8/2004 | Morgan et al. ............ 315/312 | 2009/0077405 A1* | 3/2009 | Johansen ................. 713/323 |
| 2004/0190085 A1* | 9/2004 | Silverbrook et al. ......... 358/474 | 2009/0077920 A1 | 3/2009 | Korman et al. |
| 2004/0190092 A1* | 9/2004 | Silverbrook et al. ......... 358/539 | 2009/0082888 A1* | 3/2009 | Johansen ................. 700/94 |
| 2004/0210289 A1* | 10/2004 | Wang et al. ............ 607/116 | 2009/0105076 A1 | 4/2009 | Stewart et al. |
| 2004/0226424 A1* | 11/2004 | O'Banion et al. ........... 83/397 | 2009/0113752 A1 | 5/2009 | Weir |
| 2004/0254419 A1* | 12/2004 | Wang et al. ............ 600/8 | 2009/0218249 A1 | 9/2009 | Stalter |
| 2005/0013727 A1 | 1/2005 | Hedman | 2009/0286295 A1* | 11/2009 | Medoff et al. ........... 435/162 |
| 2005/0025797 A1* | 2/2005 | Wang et al. ............ 424/422 | 2009/0311237 A1* | 12/2009 | Frost .................. 424/94.62 |
| 2005/0040832 A1* | 2/2005 | Steele et al. ............ 324/640 | 2009/0314090 A1* | 12/2009 | Troxler ................. 73/623 |
| 2005/0079132 A1* | 4/2005 | Wang et al. ............ 424/1.11 | 2009/0325240 A1 | 12/2009 | Daniell |
| 2005/0080520 A1 | 4/2005 | Kline et al. | 2009/0325628 A1* | 12/2009 | Becker .................. 455/523 |
| 2005/0082626 A1* | 4/2005 | Leedy .................. 257/432 | 2010/0014784 A1* | 1/2010 | Silverbrook et al. ......... 382/313 |
| 2005/0103446 A1 | 5/2005 | Foucht et al. | 2010/0108567 A1* | 5/2010 | Medoff .................. 208/49 |
| 2005/0107870 A1* | 5/2005 | Wang et al. ............ 623/1.44 | 2010/0112242 A1* | 5/2010 | Medoff .................. 428/22 |
| 2005/0149002 A1* | 7/2005 | Wang et al. ............ 606/1 | 2010/0171145 A1* | 7/2010 | Morgan et al. ............ 257/99 |
| 2005/0149169 A1* | 7/2005 | Wang et al. ............ 623/1.15 | 2010/0171513 A1* | 7/2010 | Magill .................. 324/601 |
| 2005/0156265 A1* | 7/2005 | Leedy .................. 257/432 | 2010/0217099 A1* | 8/2010 | LeBoeuf et al. ........... 600/301 |
| 2005/0165471 A1* | 7/2005 | Wang et al. ............ 623/1.15 | 2010/0317836 A1* | 12/2010 | Mori et al. .............. 530/387.9 |
| 2005/0216075 A1* | 9/2005 | Wang et al. ............ 623/1.15 | 2011/0079124 A1* | 4/2011 | Carrier .................. 83/63 |
| 2005/0220662 A1 | 10/2005 | Hedman | 2011/0098112 A1* | 4/2011 | LeBoeuf et al. ........... 463/31 |
| 2005/0254106 A9* | 11/2005 | Silverbrook et al. ......... 358/539 | 2011/0106627 A1* | 5/2011 | LeBoeuf et al. ........... 705/14.66 |
| 2006/0014228 A1* | 1/2006 | Simpson et al. ........... 435/7.32 | | | |
| 2006/0022214 A1* | 2/2006 | Morgan et al. ............ 257/99 | | FOREIGN PATENT DOCUMENTS | |
| 2006/0025367 A1 | 2/2006 | Simari | DE | 4424832 A1 * | 1/1996 |
| 2006/0178064 A1 | 8/2006 | Balthes et al. | DE | 19748035 | 5/1999 |
| 2006/0185441 A1 | 8/2006 | Wang et al. | EP | 0313435 | 4/1989 |
| 2006/0196398 A1 | 9/2006 | Graham | EP | 531551 A1 * | 3/1993 |
| 2006/0201022 A1* | 9/2006 | Logan .................. 34/550 | EP | 0540103 | 5/1993 |
| 2006/0226857 A1* | 10/2006 | Troxler et al. ............ 324/663 | EP | 0733456 | 9/1996 |
| 2006/0281067 A1* | 12/2006 | Simpson et al. ........... 435/4 | EP | 0743153 | 11/1996 |
| 2007/0003994 A1* | 1/2007 | Simpson et al. ........... 435/25 | EP | 0815458 | 1/1998 |
| 2007/0010702 A1* | 1/2007 | Wang et al. ............ 600/8 | EP | 1050888 | 11/2000 |
| 2007/0015424 A1 | 1/2007 | Toas et al. | FR | 2645275 | 10/1990 |
| 2007/0017113 A1 | 1/2007 | Scharpf | JP | 51122261 A * | 10/1976 |
| 2007/0023954 A1 | 2/2007 | Laver et al. | JP | S58-103361 | 7/1983 |
| 2007/0046289 A1* | 3/2007 | Troxler ................. 324/334 | JP | S62-110743 | 5/1987 |
| 2007/0063914 A1* | 3/2007 | Becker .................. 343/840 | JP | 02247488 A * | 10/1990 |
| 2007/0116991 A1 | 5/2007 | Balthes et al. | JP | H03-502728 | 6/1991 |
| 2007/0157994 A1 | 7/2007 | Scoville et al. | JP | 03156281 A * | 7/1991 |
| 2007/0184552 A1 | 8/2007 | Lynn | JP | 06003049 A * | 1/1994 |
| 2007/0187223 A1 | 8/2007 | Graham | JP | H07-198642 | 8/1995 |
| 2007/0246125 A1 | 10/2007 | Latos | JP | H08-285802 | 11/1996 |
| 2007/0248047 A1* | 10/2007 | Shorty et al. ............ 370/329 | JP | 08-323775 | 12/1996 |
| 2007/0263918 A1 | 11/2007 | Jenya | JP | H09-049817 | 2/1997 |
| 2007/0289589 A1 | 12/2007 | McFarland | JP | 09-076251 | 3/1997 |
| 2007/0291483 A1* | 12/2007 | Lys .................. 362/227 | JP | 10286212 A * | 10/1998 |
| 2008/0000547 A1 | 1/2008 | Barker et al. | JP | H11-506838 | 6/1999 |
| 2008/0000548 A1 | 1/2008 | Liu et al. | JP | 2001-018240 | 1/2001 |
| 2008/0066340 A1 | 3/2008 | Kakuno | JP | 2002046108 A * | 2/2002 |
| 2008/0078470 A1* | 4/2008 | O'Branion et al. ........... 144/356 | JP | 2005048967 A * | 2/2005 |
| 2008/0088049 A1 | 4/2008 | Dostal | JP | 2006150705 A * | 6/2006 |
| 2008/0090477 A1 | 4/2008 | Balthes et al. | JP | 2007322123 A * | 12/2007 |
| 2008/0115231 A1* | 5/2008 | Mori et al. .............. 800/3 | WO | WO 89/03047 | 4/1989 |
| 2008/0130535 A1* | 6/2008 | Shorty et al. ............ 370/310 | WO | WO 9107261 A1 * | 5/1991 |

| | | |
|---|---|---|
| WO | WO 9215435 A1 * | 9/1992 |
| WO | WO 9534945 | 12/1995 |
| WO | WO 96/28741 | 9/1996 |
| WO | WO 96/39623 | 12/1996 |
| WO | WO 97/04299 | 2/1997 |
| WO | WO 98/39639 | 9/1998 |
| WO | WO 99/13346 | 3/1999 |
| WO | WO 00/79266 | 12/2000 |
| WO | WO 01/01056 | 1/2001 |
| WO | WO 03/067275 | 8/2003 |
| WO | WO2004/004998 | 1/2004 |
| WO | WO 2004/004998 | 1/2004 |
| WO | WO 2005069021 | 7/2005 |
| WO | WO 2005/086965 | 9/2005 |
| WO | WO 2007083863 A1 * | 7/2007 |
| WO | WO 2007083864 A1 * | 7/2007 |
| WO | WO 2008010602 A1 * | 1/2008 |

OTHER PUBLICATIONS

U.S. Appl. No. 09/815,342, filed Mar. 21, 2001, John Van Doren.
"Automatic, Computer Controlled, Processing of Advanced Composites," Defense Small Business Innovation Research (SBIR) Program, Apr. 7, 1988, 25 pages.
Baumgartner et al., "Computer Assisted Dielectric Cure Monitoring in Material Quality and Cure Process Control," SAMPE Journal, 1983, pp. 6-16.
Buczek, "Considerations in the Dielectric Analysis of Composites," 40th International SAMPE Symposium, May 8-11, 1995, pp. 696-710.
Buczek et al., "Self-Directed Process Control System for Epoxy Matrix Composites," 40th International SAMPE Symposium, May 8-11, 1995, 8 pages.
"Critical Point Control/Statistical Quality Control Software Module," Micromet Instruments, 1993, 2 pages.
Day, "Cure Characterization of Thick Polyester Composite Structures Using Dielectric and Finite Difference Analysis," Composite Material Technology, ASME, 1993, vol. 53, pp. 249-252.
Desanges et al., "Changes in the Electrical Properties of Natural Rubber/Carbon Black Compounds During Vulcaniation," Revue Generale du Caoutchouc, Dec. 1957, vol. 34(12), pp. 631-649.
"Dielectric Cure Testing on Polyester Bulk Molding Compound," Holometrix Micromet, 2001, 3 pages, available at http://www.holometrix.com/holometrix/m_materialtest.asp.
"Dielectric Sensors," NETZSCH, Feb. 21, 2002, 2 pages.
"Eumetric System III Microdielectrometer", Holometrix Micromet, 2001, 5 pages.
"ICAM-1000—In-mold Monitoring for SPC, SQC, and CPC (Critical Point Control) of Thermoset Molding Operations," Micromet Instruments, Inc., Mar. 1990, 4 pages.
"ICAM-1000 Industrial Cure Analysis & Monitoring System," Micromet Instruments, Inc., Aug. 1, 1991, 1 page.
"ICAM-2000 Multi-Channel Cure Analyzer," Micromet Instruments, 1993, 2 pages.
James, "Dielectric Properties of Lumber Loads in a Dry Kiln," United States Department of Agriculture, Research Paper FPL 436, 1983, 19 pages.
James et al., "In-Kiln Moisture Monitoring Systems," Computer automation for sawmill profit: Proceedings 7333, Forest Product Research Society, Oct. 1982, pp. 91-94.
Johnson et al., "Production Implementation of Fully Automated, Closed Loop cure Control for Advanced Composite Strucutres," 34th International SAMPE Symposium, May 8-11, 1989, pp. 373-384.

Keller et al., "Computer Controlled Processing of Composites Utilizing Dielectric Signature Curves," SAMPE Journal, 1992, vol. 28(5), pp. 25-33.
Keller et al., "Real Time, In-Situ Dielectric Monitoring of Advanced Composites Curing Processes," Programmed Composites, Inc., Aug. 1, 1987, 63 pages.
Khastgir, "A Comparative Study of Step Curing and Continuous Curing Methods," Rubber World, Jan. 1994, pp. 28-31.
"Lockheed Signature Process Control for Composites Proposal," Ketema Programmed Composites, Inc., Jul. 1, 1993, pp. 1-12.
"MDE Series 10 Cure Monitor," Holometrix Micromet, Mar. 15, 2000, 2 pages.
"Mono-Probe," TYT-NAM-MON, printed Oct. 27, 2000, 1 page.
"Northrop Aircraft Division RTM System Proposal," Ketema Programmed Composites, Inc., Apr. 1, 1993, 13 pages.
O'Conor et al., "Update to the Jun. 1990 Confidential Descriptive Memorandum," Micromet Instrument, Inc., Dec. 1, 1990, 17 pages.
Persson, "A Novel Method of Measuring Cure- Dielectric Vulcametry," Plastics and Rubber Processing and Applications, 1987, vol. 7(2), pp. 111-125.
Prepreg Cure Characterization Using Simultaneous Dynamic Mechanical Analysis-Dielectric Analysis (DMA-DEA), Perkin Elmer Thermal Analysis Newsletter, date unknown, 4 pages.
"Product Selection Grid," Holometrix Micromet, 2001, 1 page, available at http://www.holometrix.com/holometrix/m_prgrid.asp.
Rajeshwar et al., "AC Impedance Spectroscopy of Carbon Black-Rubber Composites," Presentation from the Rubber Division, American Chemical Society, Orlando, FL., Sep. 21-24, 1999, 9 pages.
"Rapid RH Fast, Accurate Moisture Test for Concrete Floors," Wagner Electronics, Inc. Press Release, Jan. 1, 2005, 5 pages.
"SmartTrac," Innovative Aftermarket Systems, Inc., 2001, 2 pages, available at http://www.ias-inc.net/pages/products/smart.html.
SmartTrac Advertisement, Automotive News, May 21, 2001, 1 page.
"Textron Aerostructures Autoclave Process Control Proposal," Ketema Programmed Composites, Inc., Feb. 12, 1993, 16 pages.
"The Eumetric System III Microdielectrometer," Micromet Instruments, Inc., Sep. 1991, 4 pages.
"Thermokinetics," NETZSCH, Nov. 8, 2001, 2 pages.
"Tool Mount Sensors," Micromet Instruments, Aug. 20, 1999, 2 pages, available at http://www.micromet.com/home/rds.htm.
"Tool Mount Sensors," NETZSCH, Feb. 21, 2002, 2 pages.
"Vulcanization of Natural Rubber," NETZSCH, Nov. 8, 2001, 2 pages.
"Wellons True Capacitance Moisture Meter System," Wellons, Inc., 2005, printed on Feb. 21, 2007, 1 page.
International Search Report for International (PCT) Patent Application No. PCT/US07/67694, mailed Nov. 29, 2007.
Written Opinion for International (PCT) Patent Application No. PCT/US07/67694, mailed Nov. 29, 2007.
International Preliminary Report on Patentability for International (PCT) Patent Application No. PCT/US07/67694, mailed Jul. 9, 2009.
Official Action for Canadian Patent Application No. 2,673,820, dated Nov. 8, 2010.
Official Action for U.S. Appl. No. 11/617,910, mailed Sep. 23, 2008.
Notice of Allowance for U.S. Appl. No. 11/617,910, mailed Aug. 7, 2009.
Supplemental Notice of Allowance for U.S. Appl. No. 11/617,910, mailed Jan. 27, 2010.

* cited by examiner

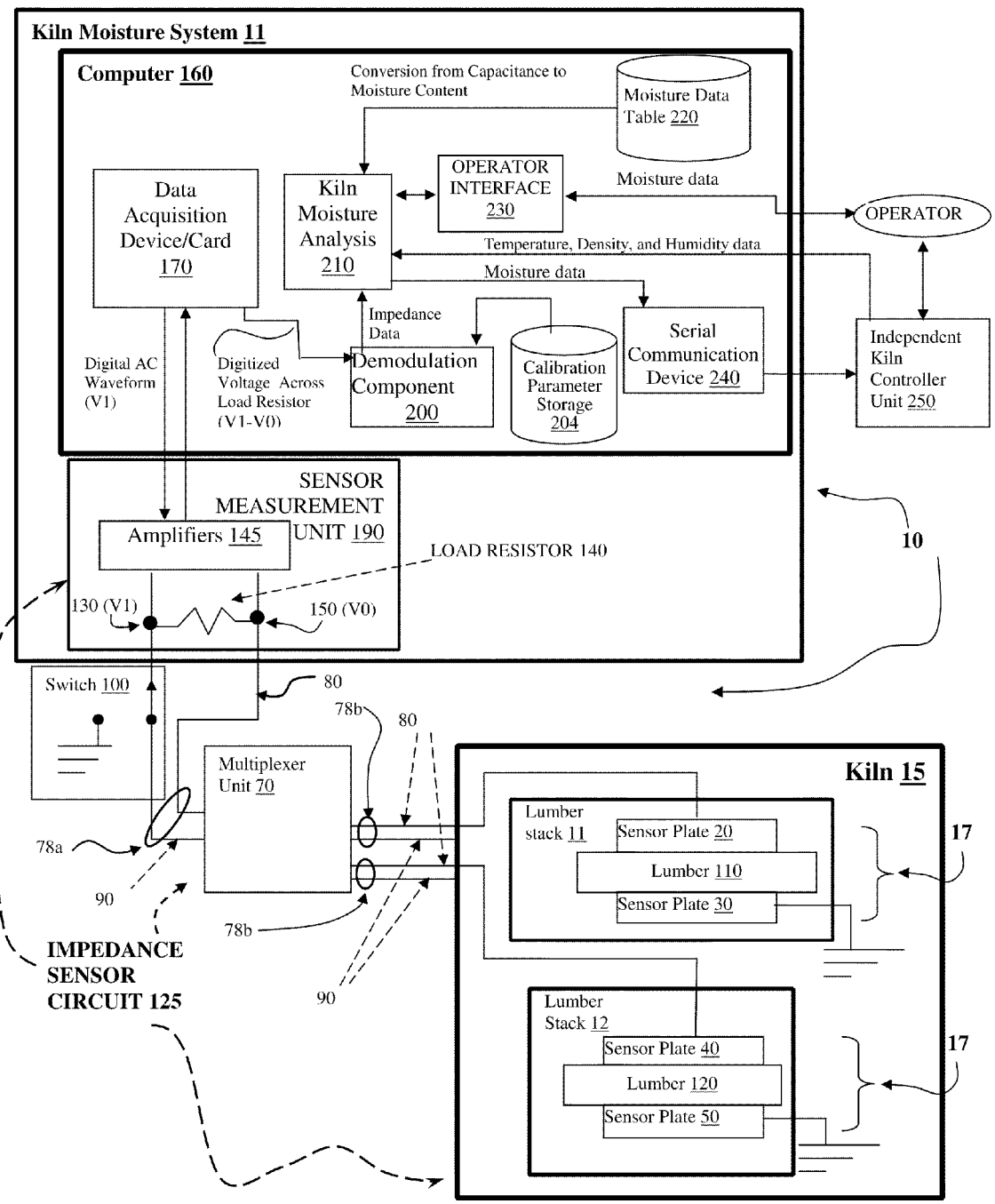
Figure 1A (voltage divider circuit)

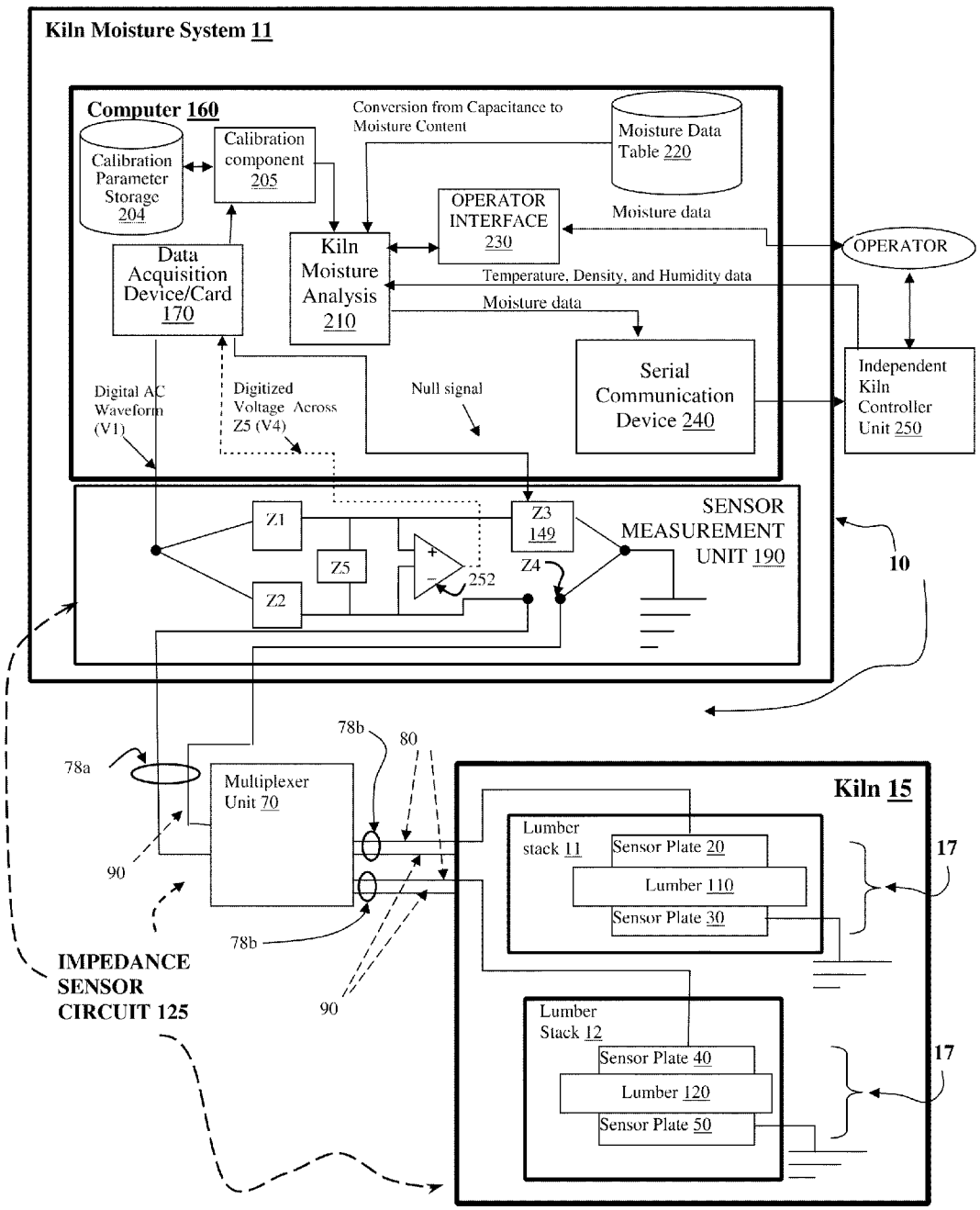
Figure 1B (bridge circuit)

Figure 1C (LCR data acquisition circuit)
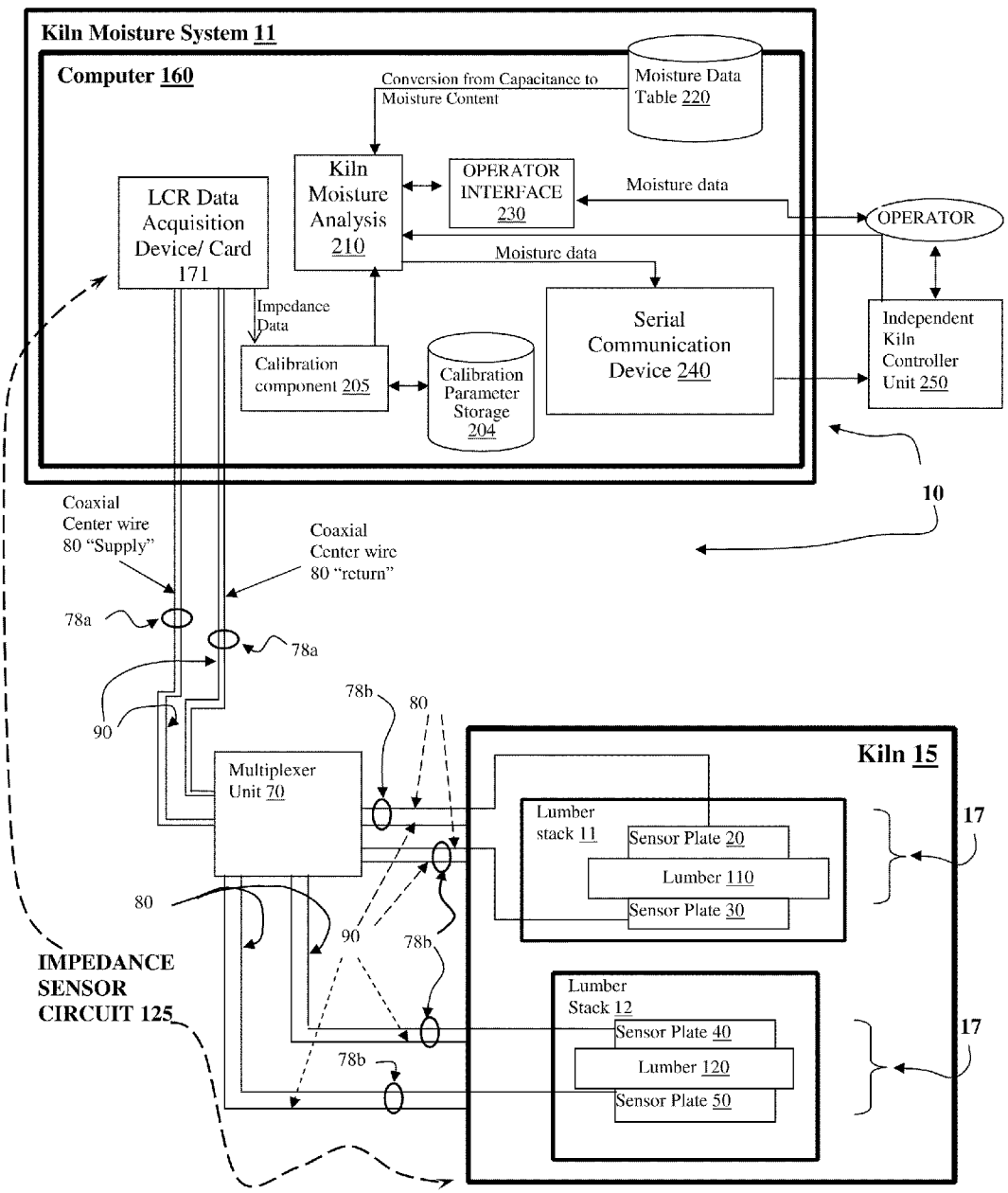

Fig 2. Plate Inserted in Kiln Stack, with Cable Attached to Plate
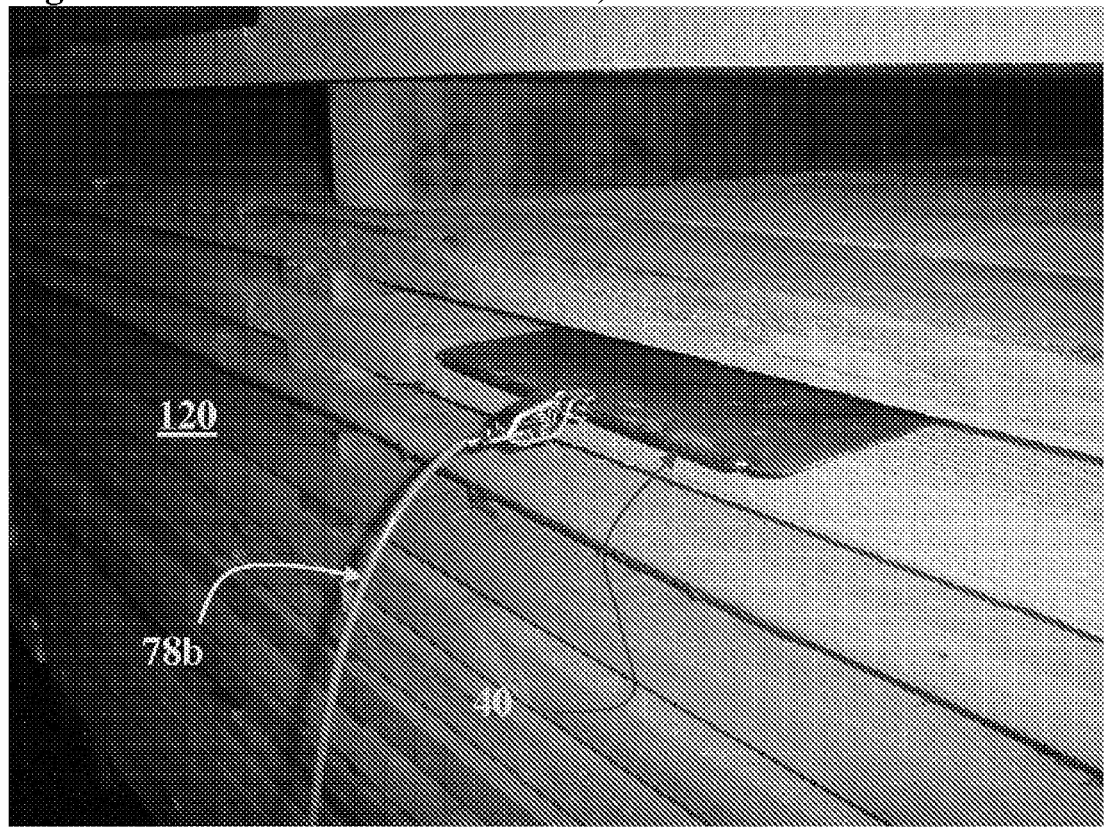

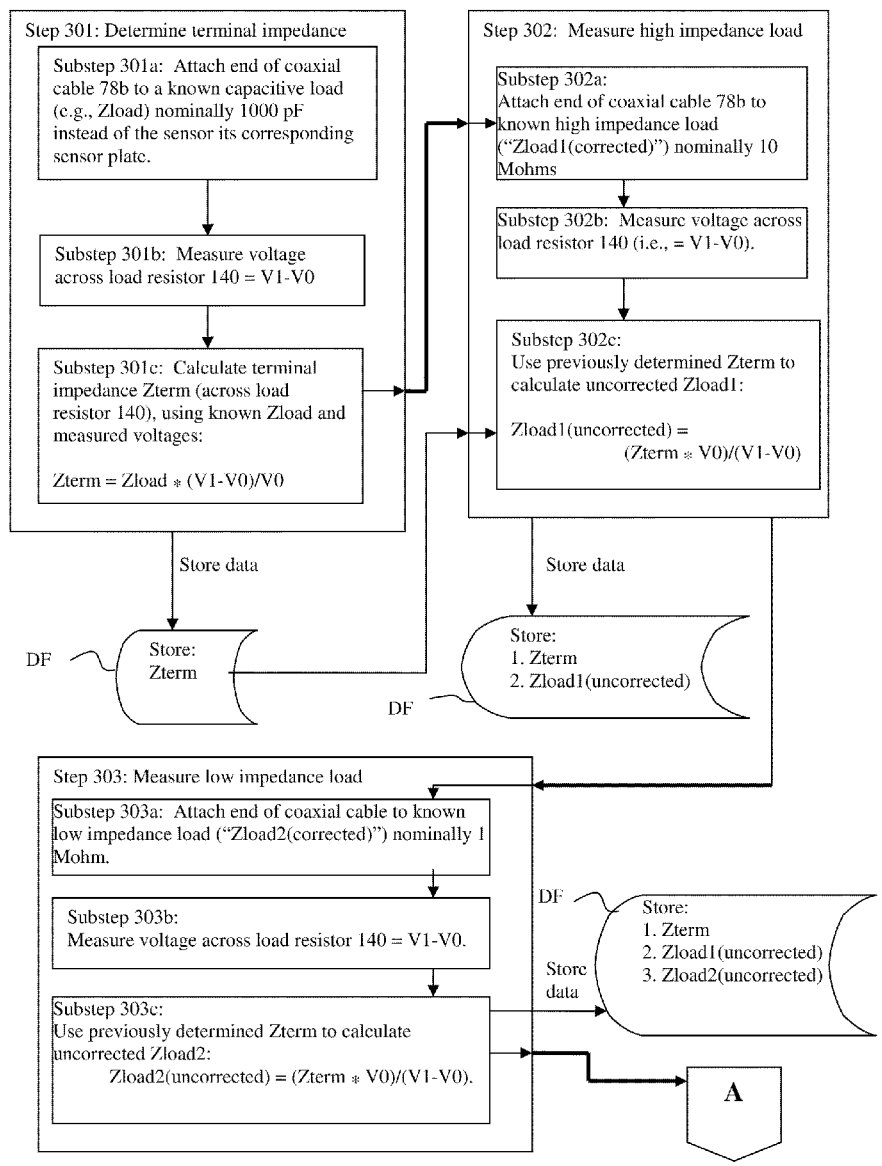
Figure 4A: Calibration flowchart, Resistor-Capacitor Network Method

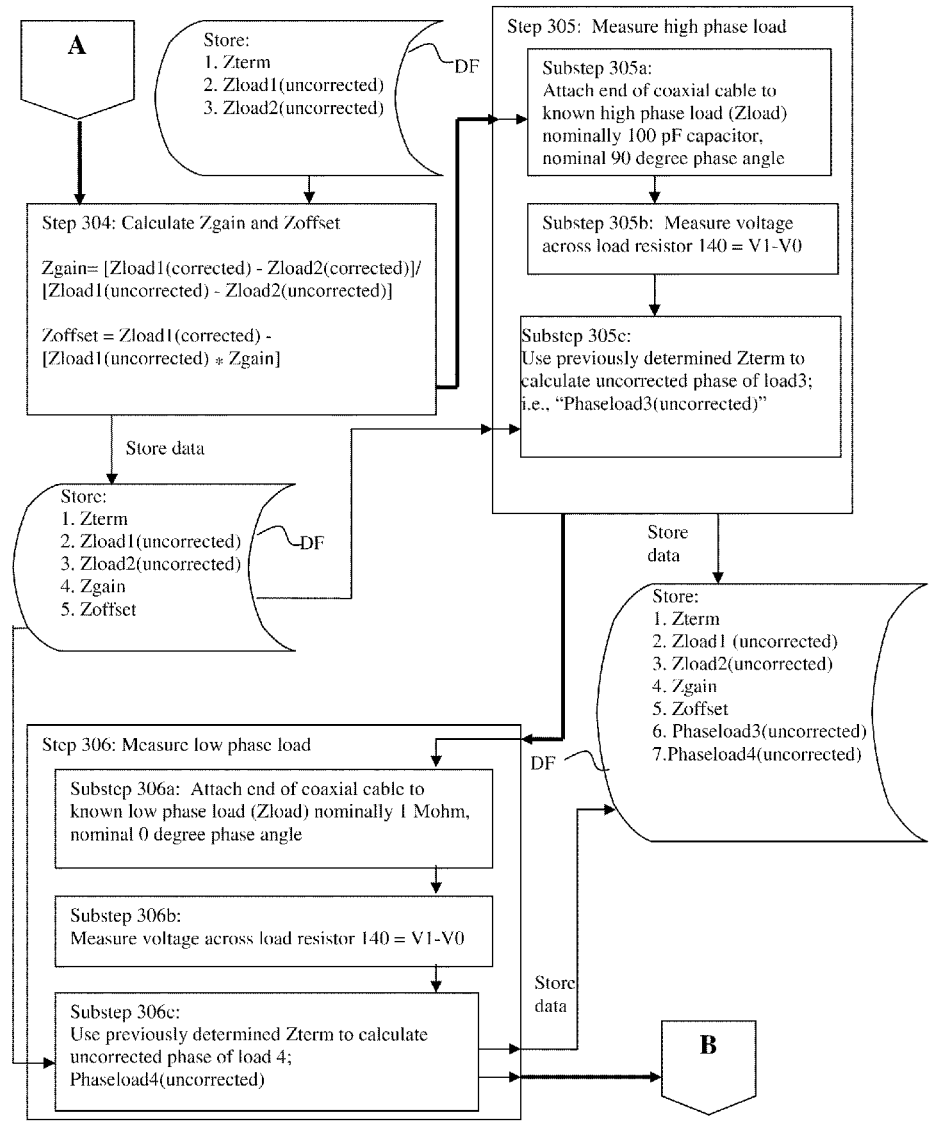
Figure 4B : Calibration flowchart, Resistor-Capacitor Network Method

Figure 4C: Calibration flowchart, Resistor-Capacitor Network Method
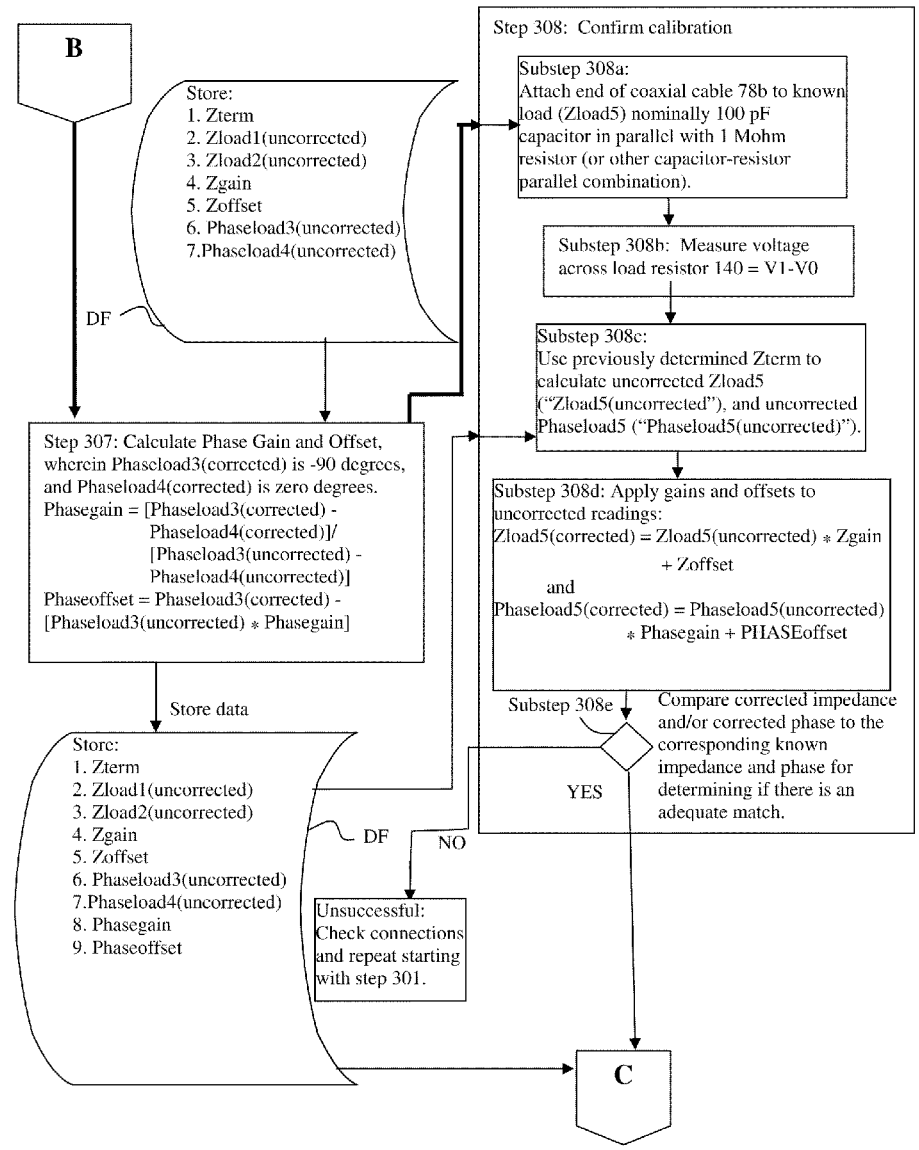

Figure 4D: Calibration flowchart, Resistor-Capacitor Network Method
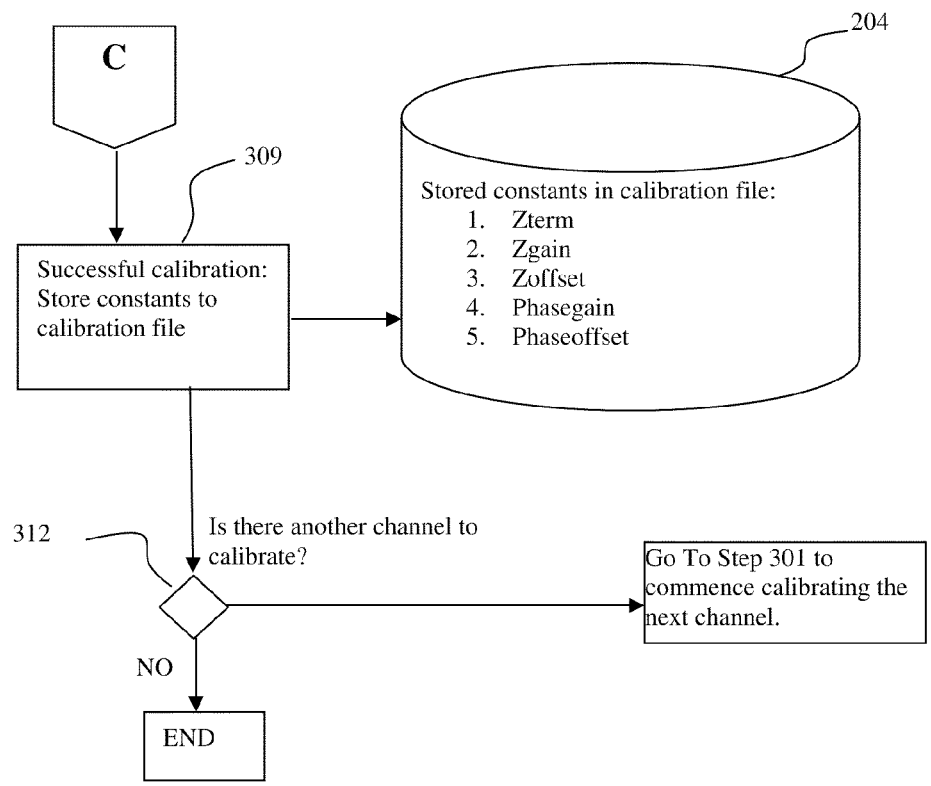

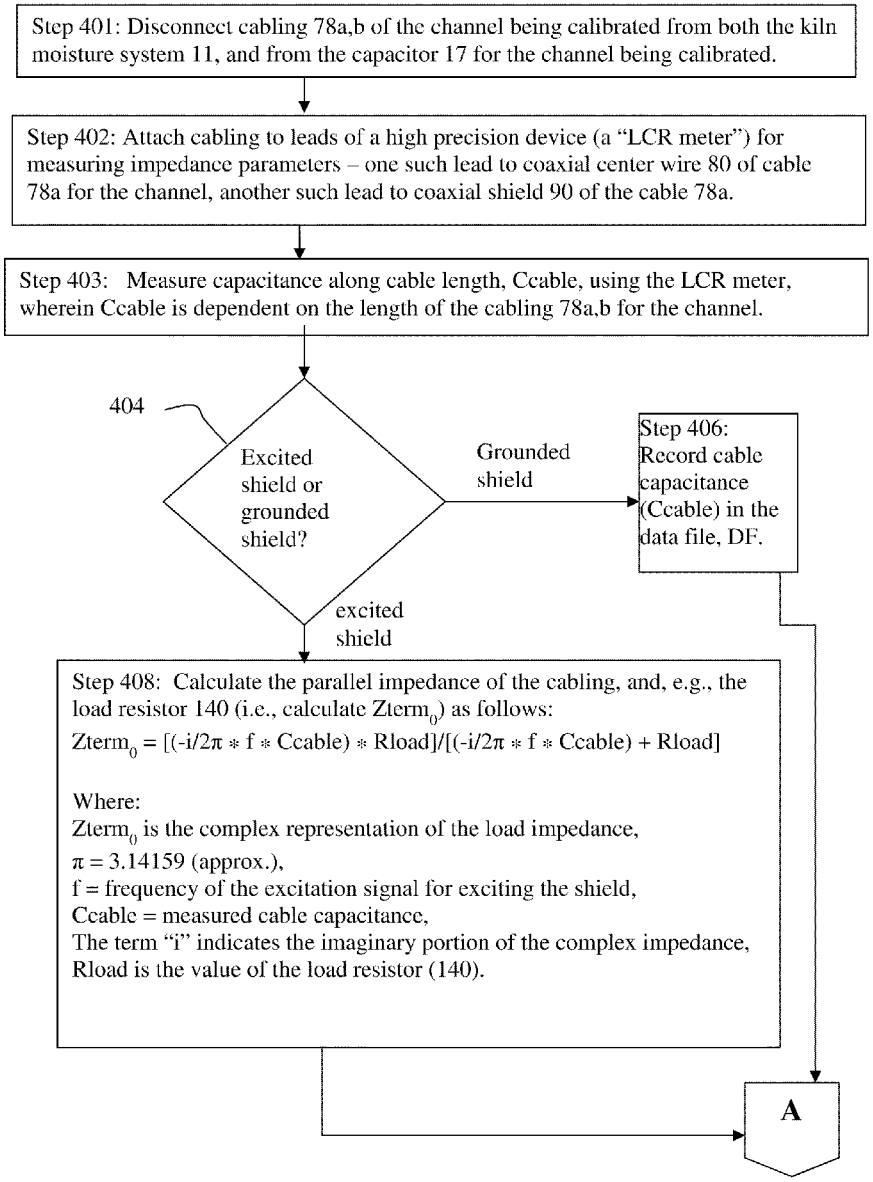
Fig. 5A: Calibration flowchart for the Impedance measurement method

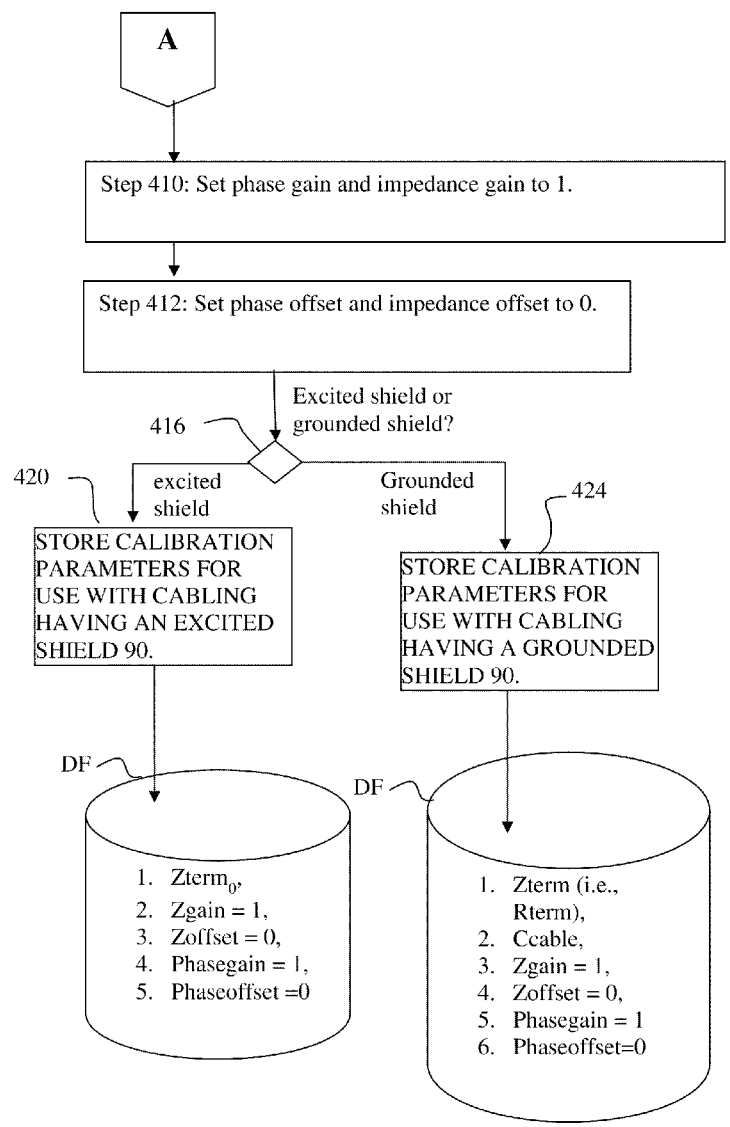
Fig. 5B (Impedance measurement meter method)

Fig. 7A (Calibration flowchart, "short-open" calibration method)
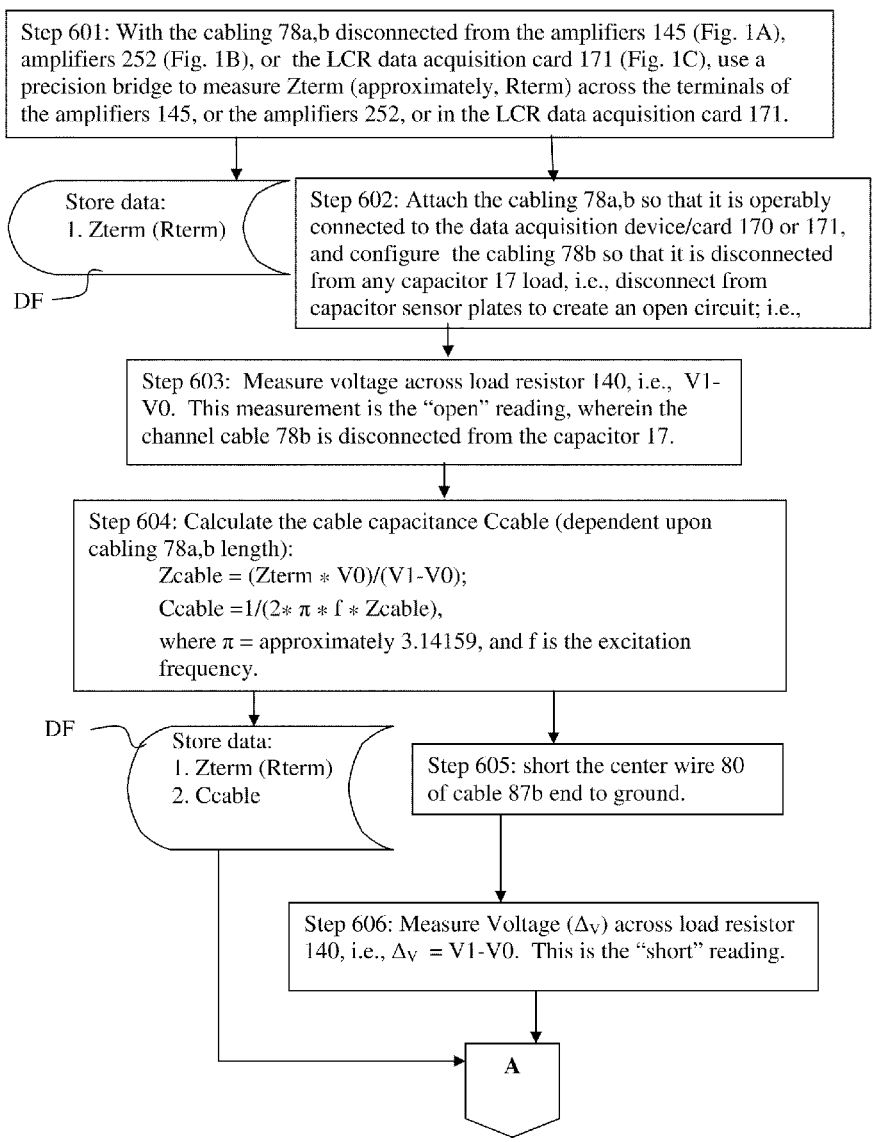

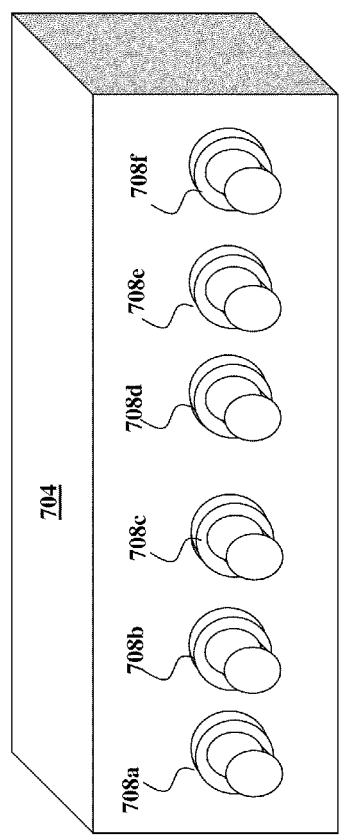

WOOD KILN MOISTURE MEASUREMENT CALIBRATION AND METERING METHODS

CROSS REFERENCE TO RELATED APPLICATIONS

The present application claims the benefit of U.S. patent application Ser. No. 11/617,910 filed on Dec. 29, 2006; the entire disclosure of which is hereby fully incorporated by reference as part of the present application.

RELATED FIELD OF THE INVENTION

The present invention is directed to calibrating measurements of signals received from sensors for measuring the moisture content of drying lumber, and in particular, to determining adjustments of such measurements to compensate for transmission induced variations in the signals, and more particularly, to determining such adjustment due to varying and/or long lengths of cabling used to transmit the signals.

BACKGROUND

Final moisture content of kiln-dried lumber is extremely critical to ensure optimal performance of the lumber in its end-use. Lumber that is too wet (under-dried) is prone to mold growth that can significantly compromise the lumber's strength, durability, and appearance. Under-dried lumber will also experience shrinkage as it dries to equilibrium, resulting in dimensional problems. Lumber that is too dry, or over-dried, will tend to warp and crack, also causing dimensional problems and rendering it less useful in most applications. Over-drying also results in lost productivity, and increased energy costs.

Both under drying and over drying will significantly reduce the desirability and market value of the lumber. For these reasons, in-situ monitoring of kiln dried lumber is highly advantageous.

It is established in prior art that it is possible to position steel plates spaced apart in a lumber stack, so that an electrical signal can be applied while drying of the lumber is in progress. The capacitance response between the plates can then be used as an indicator of moisture content, since the main dipolar constituent between the plates is the water in the lumber. Prior art systems of this type have been commercially available for two decades, from a variety of vendors. Such prior art systems (e.g., by the manufacturers Wagner, Wellons, and Accudry) have been described in significant detail in various public disclosures, including the following U.S. Pat. No.: U.S. 4,389,578 by Wagner; U.S. Pat. No. 4,580,233 by Parker, et. al.; U.S. Pat. No. 6,703,847 by Venter et. al.; and U.S. Pat. No. 6,989,678 by Venter et. al. each of which is fully incorporated herein by reference. Additionally, the following U.S. Patent Nos. are fully incorporated herein by reference: U.S. Pat. No. 3,807,055 by Kraxberger; U.S. Pat. No. 4,107,599 by Preikschat; U.S. Pat. No. 6,124,584 by Blaker et. al.; U.S. Pat. No. 6,281,801 by Cherry et. al.; U.S. Pat. No. 6,784,671 by Steele, et. al.; U.S. Pat. No. 6,784,672 by Steele, et. al.; U.S. Pat. No. 7,068,050 by Steele; U.S. Pat. No. 7,068,051 by Anderson; and U.S. Patent Application Publication No. US 2004/0187341 by Studd, et. al. is also fully incorporated herein by reference.

Such prior art systems use electrical metering devices to measure the moisture content of lumber as it dries in a kiln. In most (if not all) cases, these electrical metering arrangements involve placement of steel plates in the lumber to form a capacitor. The various systems then employ some form of cabling to carry the electrical signal from the plates back to such a metering device. The metering device measures the electrical capacitance of the circuit formed by the steel plates and the lumber. The capacitance is closely related to the moisture content in the lumber, so the metering device output can be appropriately scaled to read out in terms of moisture content. Typically the meter provides the capacitance values from the plates to either a PC (i.e., personal computer) or a PLC-based controller (i.e., programmable logic controller). The transform from capacitance to moisture content is performed either in the meter or in the PLC/PC, and the moisture content values are then used by a kiln controller (a separate control system) to identify when no further drying of the lumber is desired.

Typically, prior art systems include multiple metering devices (each also referred to herein as a capacitive meter, or evaluator) mounted on either the kiln interior or the kiln exterior. In this manner, the electrical signals to and from the steel plates, inserted in the kiln stacks (i.e., lumber stacks within the kiln), travel only a very short distance, e.g., less than 50 linear feet via carefully isolated conductive wires.

The placement of the metering devices close to the kiln stack is primarily due to difficulties with calibration of the signals from the capacitor plates to such a metering device. In particular, the wiring (also referred to as cabling herein) from the capacitor plates to the metering device is a significant design issue in establishing a reliable and accurate metering circuit. For example, numerous issues must be considered in the design of the cabling, including the following:

The cables must be electrically insulated or isolated from all potential electrical grounds.

The cabling must be corrosion resistant.

The cabling must be capable of dealing with extremes in temperature, typically from as low as −60 F. up to 250 F.

The cabling must be mechanically robust and able to survive rough handling.

The cabling must be resistant to electrical noise.

The metering equipment must be calibrated to effectively remove signal losses inherent to the cabling from the capacitance measurements output by the metering equipment. In other words, all cabling will have losses of some sort that will appear to the metering equipment as an electrical load. However, it is desirable to have a calibration method that is able to compensate for the cabling losses such that the meter only outputs data indicative of the capacitance of the plates (corresponding to lumber moisture content), and not losses from the cables themselves.

Most prior art kiln moisture measurement systems attempt to address the calibration issue by minimizing the length of the cable length to the metering device. As indicated above, the metering devices are typically mounted on the exterior of the kiln, and as close as possible to the points where the moisture measurements are taken. Thus, by keeping the length of the cable short, the signal losses in the cable are reduced, and most of the cable signal can be attributed to the capacitance of the plates. Additionally, the relatively small losses incurred can be adjusted out with empirical tuning and zeroing of the circuits to normalize their response, as one skilled in the art will understand.

However, locating the meters on the kiln exterior makes them susceptible to weather conditions, which can be extraordinarily harsh. Many North American kilns are located in the Northern U.S. and Canada where temperatures are extremely low in the winter. Kilns vent a high amount of moisture, which turns to ice on the kiln exterior. In some cases, the high weight of ice on the meter is enough to cause structural damage to the meter. Meters are sealed, but the sealant is not foolproof and in some cases the ever-present moisture in the kiln-environment can get inside the meter, shorting it out. Thus, the reduced lifetime and reliability of the meters is a serious shortcoming in the prior art systems.

Ancillary problems also result from prior art cabling approaches. In particular, prior art calibration methods are only well suited to very simple wiring methods, such as a bare stranded wire or an insulated stranded wire, and with very short cable lengths. Moreover, when non-insulated cables are used in a kiln, the cables are kept electrically isolated via insulating standoffs. That is, for each cable, there is an electrically isolated swing-arm for supporting the cable in a tensioned state between a capacitor plate and a meter. However, electrically isolated standoffs and their cables can be awkward to kiln workers to manipulate, and falling lumber in the kiln can cause the non-insulated cables to short circuit.

Moreover, both non-insulated stranded wire and insulated stranded wire are susceptible to electrical noise which can further compromise the validity of the capacitance signal. Additionally, although coaxial cable is far more resistant to electrical noise than non-insulated stranded wire and stranded wire and communicates a superior signal (e.g., a higher signal to noise ratio), the use of coaxial cable can be difficult for prior art kiln moisture monitoring systems in that there are high capacitance levels generated in coaxial cable that can not be easily removed by the simple prior art calibration methods.

In summary, the above described prior art systems for drying lumber results in a variety of problems:
1. Short circuiting of the wiring is difficult to prevent. Since the wires are non-insulated, the wires must be kept electrically isolated via a series of insulated standoffs installed in the kiln interior.
2. Installation of a meter or evaluator can be problematic. Since the meter must be installed on the kiln exterior, and since kilns are often stacked together with limited external wall space, it may be necessary in some cases to install the meters on the kiln roof This is potentially hazardous for electricians and makes servicing the meters very difficult. Moreover, the difficulty of installation results in high installation labor cost as well as excessive kiln down-time when such a prior art kiln moisture monitoring system is installed.
3. The location of the meters on the kiln exterior makes them susceptible to weather conditions, which can be extraordinarily harsh. Moreover, kilns vent a high amount of moisture, which can turn to ice on the kiln exterior. In some cases, the high weight of ice on the meter is enough to cause structural damage to a meter. Meters are sealed, but the sealant is not foolproof and in some cases the ever-present moisture in the kiln-environment can get inside the meter, shorting it out.
4. In order to prevent the non-insulated wires from coming into contact with each other, a tensioning system on a swing arm is required. This swing arm can become problematic in the kiln, and can be broken off by falling boards or equipment. It can also be electrically shorted by a variety of sources, including chain falls, cables, other wiring, etc.
5. The use of standard wiring makes the system susceptible to electrical noise, which is generated by the large equipment motors in use, as well as more typical sources such as fluorescent lighting.
6. Accurate and reliable calibration in the prior art monitoring/controlling systems can be difficult. In particular, such prior art calibration requires careful correction of the capacitance reading at the end of the wire leading from the meter to the plates.

For all the aforementioned reasons, it is more advantageous to install the metering equipment in a centralized, environmentally-controlled equipment space, such as a control room, wherein humidity, moisture, and ice is prevented from damaging the electronics in the metering equipment. Further, it is advantageous to run the wiring with insulated coaxial cable rather than with standard stranded wire since coaxial cable offers superior noise rejection and a high degree of resistance to electrical faults, such as an inadvertently grounded cable. Moreover, use of these insulated coaxial cables makes it unnecessary to mount the cabling on complicated swing arms that are susceptible to breakage and electrical faults. These advantages are provided by the kiln moisture monitoring system disclosed hereinbelow.

Description of Terms

Meter: A set of electronics (and associated software and/or firmware) used to measure the capacitance (or other electrical properties, e.g., resistance, admittance, reactance, impedance, etc.) in a kiln lumber stack, and from such measurements, determine the moisture content of the lumber stack being dried in the kiln. The set of electronics typically includes a signal generator that excites a pair of capacitor plates, a set of amplifiers that measure the excitation and the response voltages from the capacitor plates, a comparator that evaluates the phase and amplitude of the voltage responses from the capacitor plates, a demodulation component that converts the electrical data to capacitance (more generally, impedance) and finally to moisture content in the lumber being dried, and a power supply circuit that supplies power to the aforementioned circuit components. In the case of prior art systems, such electronics typically includes an electronics device (for receiving lumber capacitance measurements) installed on the kiln exterior or kiln interior, near the portions of the lumber from which the capacitance measurements are taken. In at least one preferred embodiment of the present disclosure, the meter is located in a centralized location in an environmentally controlled room.

Metering Point: The lumber between a pair of capacitor plates from which capacitance measurements are obtained.

Channel: A channel refers to the a pair of plates forming a capacitor within a kiln lumber stack, and the cabling for communicating, to a meter, capacitance readings generated by the pair of plates. Typically, most kilns for drying lumber employ 8 channels (i.e., 8 pairs of capacitor plates) per lumber stack in a kiln, wherein each pair measures the capacitance of the drying lumber at a different localized area within the lumber stack. In the case of prior art systems, a meter located on the exterior of the kiln normally serves 1 or 2 channels. Therefore with a prior art system, 4 to 8 meters are required to serve a single kiln with 8 metering points. In the case of the present novel disclosure, the meter, located in a control room, may be coupled with a multiplexer thereby allowing the meter to serve up to 40 such channels. Therefore in the present novel disclosure, a single meter can serve up to 5 kilns, each with 8 metering points (i.e., eight capacitor plate pairs).

Terminal Impedance: The ratio of complex voltage to complex current at the input terminals of an amplifier.

SUMMARY

The present disclosure describes a lumber moisture measurement system (also referred to herein as a "moisture measurement system", and a "meter" that includes highly accurate calibration methods to standardize the signal response in each of one or more channels (i.e., a channel as described hereinabove) so that the output (i.e., capacitance measurements and/or lumber moisture content values) from the meter is substantially independent of signal transmission peculiarities or differences that occur on one channel and not another channel. More specifically, for each channel, capacitances generated in cables, such as coaxial cables, can be effectively cancelled. In particular, calibration methods disclosed herein allow for long lengths of coaxial cable (e.g., up to 1000 linear feet) to be effectively used in the circuitry for monitoring lumber drying in a kiln without the cable length adversely affecting the lumber moisture content measurements determined by the meter. Moreover, the long cable lengths facilitate the centralizing of kiln monitoring electronics, e.g., such as metering devices, in an enclosure satisfying NEMA (National Electrical Manufacturers Association) standards, and in particular, such an enclosure may be in a wood drying monitoring control room, wherein such electronics are not subject to weather variations and are easily accessible for maintenance.

The moisture measurement system disclosed herein also includes shielded coaxial cabling, encased in conduit, for making the connection to the capacitor plates in the kiln. This offers a high degree of electrical noise resistance, and the insulation precludes the possibility of electrical shorts. Since the cabling is now insulated, a tensioned swing-arm device is no longer required, removing the mechanical complications associated with this device. Installation of insulated electrical stand-offs is also no longer required.

In one embodiment, coaxial cabling, encased in conduit, is used to transport signals between a wood drying monitoring meter, and a connection to a pair of capacitor plates in a kiln.

The present disclosure describes three embodiments by which metering (i.e., monitoring) of moisture in the lumber within a kiln can be performed, wherein each one of the three embodiments is suitable for one or more of the calibration methods being described. The methods described in the three embodiments can include changes in the metering electronics and cabling, primarily including changes to the sensor measurement portion of the moisture measurement system. However, to a user, whichever embodiment is employed is substantially transparent in that each embodiment provides substantially identical functionality and user interaction appearance. Briefly, the three metering embodiments are:
 (a) A voltage divider embodiment which, at a high level, includes a voltage divider circuit, and wherein the coaxial cabling can be:
  a. with excited coaxial shield, or
  b. with grounded coaxial shield
 (b) A bridge circuit embodiment which, at a high level, is similar to the voltage divider embodiment. The bridge circuit embodiment includes a substantially different lumber moisture capacitor measurement unit. In particular, such a bridge circuit may be configured as a balanced bridge as is described further hereinbelow.
 (c) A LCR data acquisition circuit embodiment which, at a high level, is similar to the voltage divider embodiment. The LCR data acquisition embodiment includes a substantially different lumber moisture capacitor measurement unit. This embodiment includes a LCR data acquisition device or card (such as the PXI-4072 Flex DMM by National Instruments), wherein data acquisition card is specifically designed to output one or more of: inductance, capacitance, and resistance (i.e., LCR), and of a circuit (i.e., a channel) when the card is attached to an impedance load.

The present disclosure further describes three alternate/optional calibration methods by which the cabling (e.g., the length thereof) for a channel can be calibrated so that the electrical properties of the cabling (and cabling variations between channels) do not detrimentally affect a determination of the moisture in the lumber being dried in a kiln. These three calibration methods can be described as follows:
 1. Resistor-Capacitor network method: This method uses a high precision resistor-capacitor network as an impedance standard for normalizing the signal response from each channel so that cable induced signal characteristics are substantially removed or factored out of signal responses from each channel.
 2. Impedance measurement method: This method uses a high precision meter (LCR meter or high precision bridge) to precisely measure, for each channel, all non-trivial, non-lumber related impedances within the channel. The resulting measurements are used in normalizing the signal response from each channel so that such non-trivial, non-lumber related impedances do not substantially affect resulting estimates of moisture in the drying lumber.
 3. Short-open method: For each channel, this method takes calibration measurements with the channel in: an open-circuit configuration, and a short-circuit configuration, which then allows for measurement of all impedances within the channel. Such measurement of all impedances then facilitates normalizing the response from each channel.

Each of the above calibration methods avoids the problems described in the Background section above which plague prior art systems. Furthermore, each of the calibration methods determines, for each channel, a plurality of calibration parameter values that are used to adjust or correct electrical characteristics of signals received from the channel's cabling so that the corrected signals are more indicative of the moisture content of the lumber being dried. That is, the corrected signals are more nearly like the signals generated by the moisture sensitive sensors which are placed in or near the drying lumber being monitored. Accordingly, once such a plurality of calibration parameter values are determined, for a channel of a given metering circuit embodiment, these values may be accessed for correcting signals over an extended period of time (e.g., days, weeks, or months), and thus a potentially lengthy time series of signals can be adjusted or corrected without recomputing the plurality of calibration parameter values.

Moreover, the novel moisture measurement system disclosed herein includes centralized metering electronics (e.g., in a NEMA enclosure of a control room) instead of distributing the meters adjacent their corresponding kilns as provided by prior art systems. Accordingly, external installation and servicing of meters is no longer required. Any service required to the metering equipment can be done within the control room. Thus, since the electronics are now enclosed in a controlled environment, substantially all weather-related meter failures caused by ice, water, wind, etc. are prevented. Moreover, moisture measurement system installation and maintenance access becomes far safer and much easier. Additionally, a reduced amount of moisture monitoring electronics is required because most (if not all) of the weather sensitive electronics can be centralized.

The moisture measurement system disclosed herein additionally includes conduit and cabling that can be installed external to the kiln while the kiln is still operating, thus making kiln down time very short for the installation. All the conduit, cabling, and connectors may be standard electrical equipment that can be installed by any electrician, so highly specialized knowledge and equipment (such as electrical insulating stand offs and swing arms) are not needed.

Additional benefits and features of the moisture measurement system and methods for calibrating such a system will become evident from the accompanying figures, and the description herein below.

BRIEF DESCRIPTION OF THE DRAWINGS

FIG. 1A is a block diagram showing the components of the moisture measurement system, configured as a voltage divider circuit.

FIG. 1B is a block diagram showing the components of the moisture measurement system, configured as a bridge circuit.

FIG. 1C is a block diagram showing the components of the moisture measurement system, configured as a LCR data acquisition circuit.

FIG. 2 shows a sensor plate inserted in a kiln stack of lumber, with the cable attached via a spring-clip connector.

FIGS. 4A through 4D disclose a flowchart describing the calibration of the voltage divider metering embodiment (FIG. 1A), using a resistor-capacitor network, wherein the coaxial cabling is electrically excited.

FIGS. 5A and 5B is a flowchart describing the calibration using the impedance measurement method.

FIGS. 7A and 7B is a flowchart describing the calibration using the "short-open" method, wherein the coaxial cabling has a grounded shield 90.

FIG. 8 shows an exterior view of the calibration box 704.

DETAILED DESCRIPTION OF INVENTION

Figure 3A:
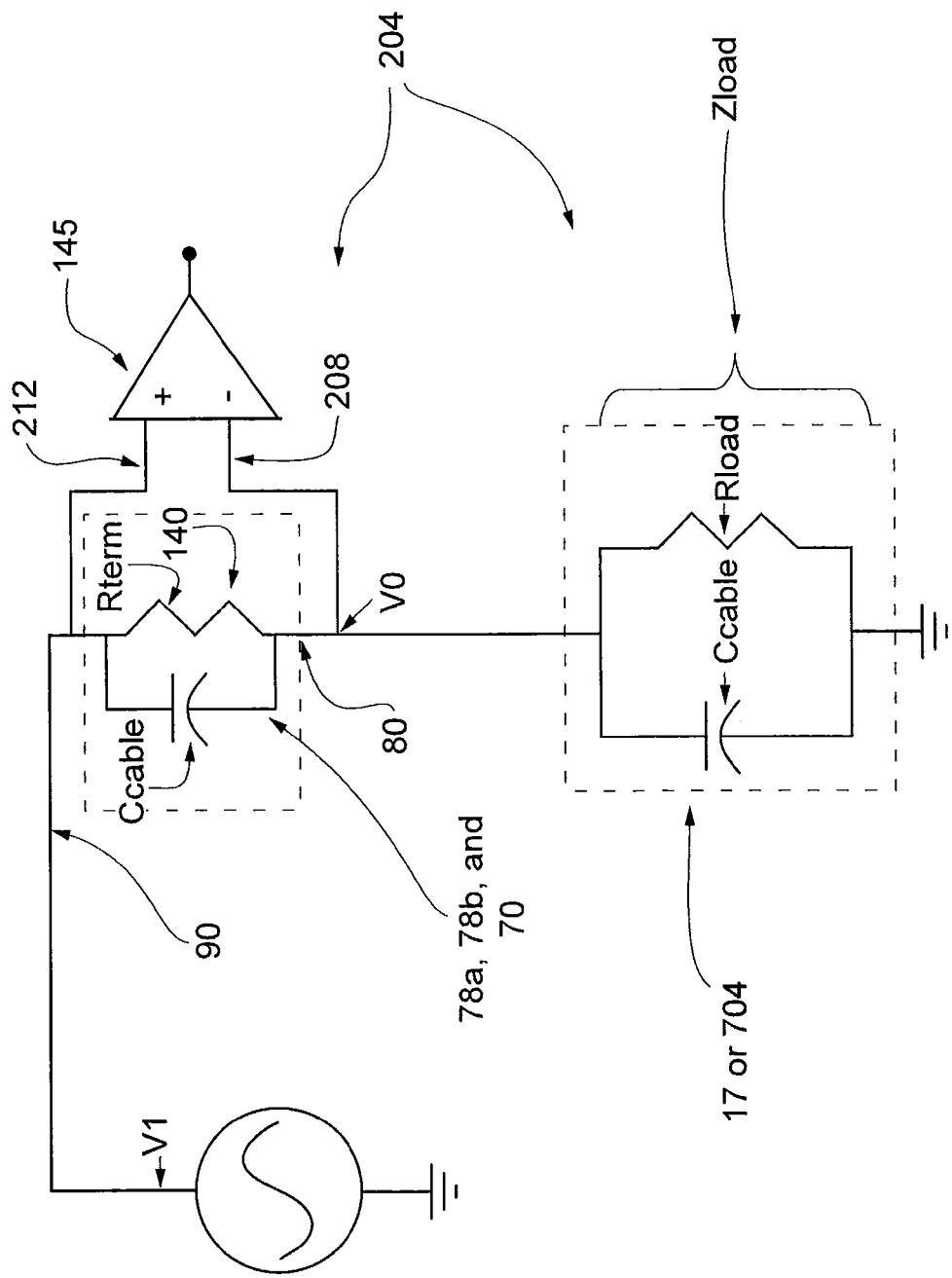
FIG. 3A is a schematic showing the circuit model for the voltage divider metering method with an excited coaxial shield.

Each of the FIGS. 1A, 1B and 1C show a different embodiment of a moisture measurement system 10. FIG. 1A shows an embodiment of the moisture measurement system 10 configured as a voltage divider. The moisture measurement system 10 includes a kiln moisture system 11 that performs key services including: moisture metering (i.e., receiving moisture readings from moisture sensors 20, 40 within the drying lumber 110, 120, cf. FIGS. 1 and 2), data collection, data storage, interfacing with an operator, and communicating between the various components of the moisture measurement system. For each of one or more kilns 15, the kiln moisture system 11 signally communicates with kiln capacitors 17 (e.g., sensor plates 20, 40), wherein each capacitor 17 includes a pair of the sensor plates (e.g., the pair 20 and 30, or the pair 40 and 50) spaced apart by a predetermined amount of lumber (e.g., 110 or 120). In particular, the sensor plates of such a pair may be spaced apart by, e.g., a stack of lumber in a range of 30 to 60 inches thick, and more preferably about 35 to 50 inches thick, and most preferably approximately 40 inches thick. For each kiln capacitor 17, the signal communication between the capacitor 17 and the kiln moisture system 11 may be via a multiplexer unit 70 that serves as a switching device to allow the kiln moisture system 11 to interface with multiple communication channels provided on the communication cabling 78a and 78b, wherein for each of the sensor plates 20 and 40 (i.e., for each one of the capacitors 17), there is a corresponding unique one of the channels identified by the multiplexer unit 70. To be clear, a channel in the present disclosure is an electrical path for a series of electrical signals from a single predetermined signal source, wherein such signals are able to be identified as originating from the predetermined source rather than from another source. In the present disclosure, there typically is a plurality of such channels, a unique such channel communicating between the moisture system 11 and a unique one of the sensor plates (i.e., 20 or 40 in FIG. 1A; however, in other embodiments hereinbelow sensor plates 30 or 50 as well). Thus, each such channel corresponds to: (a) a first length of a signal conducting medium (e.g., coaxial cabling) between the multiplexer unit 70 and one of the sensor plates 20, 30, 40 or 50, and (b) a second length of a signal conducting medium between the multiplexer unit 70 and the moisture system 11. However, as one of ordinary skill in the art will understand, the multiplexer unit 70 is not necessary, and accordingly, only a single length of cable 78 may be needed. However, an embodiment without the multiplexer unit 70 is likely to require duplication of various electrical components. Accordingly, for a given channel, the phrase "at least one length of cabling" is used herein to refer to both: (i) a single length of cabling 78 between a sensor (e.g., 20 or 40), and a data acquisition device (e.g., 170 of FIGS. 1A, 1B, or 171 of FIG. 1C, as will be further described hereinbelow), and (ii) multiple lengths of cabling 78 between a sensor (e.g., 20 or 40), and a data acquisition device. Moreover, it is to be understood that the term "cabling" for a channel refers to one or more cables such as the two cables 78a,b.

Note that the multiplexer unit 70 typically serves as the switching device between the kiln moisture system 11 and sensor plates (of capacitors 17) in a plurality of kilns 15. That is, the multiplexer unit 70 performs standard multiplexing functions for switching the signal communications between the channels, and in particular, the multiplexer unit rapidly switches signal communications between the kiln moisture system 11 and each of a plurality of the capacitors 17.

The cabling from the kiln moisture system 11 to the multiplexer unit 70 and then on to each of the sensor plates (e.g., 20, 40) includes: (a) a single shielded coaxial cable 78a between the moisture system 11 and multiplexer unit 70, and (b) at least one coaxial cable 78b between the multiplexer unit 70 and each one of capacitors 17. In particular, for each coaxial cable 78b contacting a corresponding one of the sensor plates 20 or 40, the cable's coaxial cable center conductor 80 is attached to this sensor plate (e.g., 20 or 40), and the coaxial cable shield 90 (of this cable 78b) is either excited or grounded depending on the position of a switch 100 (FIG. 1A) which is described hereinbelow. The purpose of the coaxial shield 90 (in both cable 78a and cables 78b) is to reduce the electrical noise transmission to the center conductor 80 which the shield surrounds, and thereby reduce the signal noise communicated between the sensor plates (20 and 40) and the kiln moisture system 11. Note that in all embodiments disclosed herein the center conductor 80 is electrically excited during both the calibration process and during the process of actively monitoring the drying of a lumber stack within a kiln 15.

The grounding switch 100 allows for two different configurations of the coaxial cables 78a and 78b. In the "excited" configuration (i.e., in-line), the switch 100 excites all coaxial shields 90 with an excitation voltage. When the switch 100 is in an "excited" configuration for exciting the all coaxial cable shields 90, the capacitance between the center wire 80 and the surrounding coaxial shield 90 adds impedance in parallel with the load resistor 140. Note that when modeling a circuit including: (a) the kiln moisture system 11, (b) the multiplexer unit 70, (c) the switch 100, (d) the coaxial cabling 78a and 78b, (e) one of the pairs of sensor plates (e.g., the pair 20, 30, or the pair 40, 50) for one of the capacitors 17, and (f) the corresponding lumber stack between the pair of sensors (e.g., lumber stacks 110, or 120), this impedance in parallel with the load resistor 140 must be factored into the circuit model if calibration of capacitance signals obtained from the capacitor 17 is to be highly accurate.

Alternatively, when the switch 100 is in a "grounded" configuration, the switch 100 grounds all the coaxial shields 90. In the grounded configuration, the switch 100 adds capacitance from each center wire 80 to ground into the circuit, e.g., the circuit of the kiln moisture system 11, the multiplexer unit 70, the switch 100, the coaxial cabling 78a and 78b, one of the pairs of sensor plates (e.g., the pair 20, 30, or the pair 40, 50) for one of the capacitors 17, and the corresponding lumber stack between the pair of sensors (e.g., lumber stacks 110, or 120). Thus, the capacitance from each center wire 80 to ground must be factored into a model of the circuit for accurately calibrating the capacitance signals obtained from the capacitor 17.

In each of the FIGS. 1A, 1B and 1C, the combination of: the kiln moisture system 11 (more particularly, in FIGS. 1A and 1B the sensor measurement unit 190, and in FIG. 1C the LCR data acquisition device or card 171), the multiplexer unit 70, one of the pairs of sensor plates (e.g., the pair 20, 30, or the pair 40, 50) for one of the capacitors 17, and the corresponding lumber stack between the pair of sensors (e.g., lumber stacks 110, or 120), and the coaxial cabling 78a and 78b electrically connecting these other components is identified as electrical circuit 125.

Each of the three embodiments of the kiln moisture system is further described in the three sections immediately following.

First Embodiment (FIG. 1A): Kiln Moisture System 11 Using A Voltage Divider Circuit 125

In FIG. 1A, the type of circuit formed by circuit 125 is a simple voltage divider circuit, as one of ordinary skill in the art will understand. The circuit 125 of FIG. 1A can be excited with an AC signal at point V1 130 (V1 also used to identify the voltage at this point). The voltage across the load resistor 140 can then be measured with high precision amplifiers 145, and the current flow (I*) through the circuit 125 can then be determined. By also ascertaining the voltage on the load resistor 140 at point V0 150 (V0 also used to identify the voltage at this point), the complex impedance (Z*) of the drying lumber stack (e.g., 110 or 120) between a corresponding pair of sensor plates for the circuit 125 can then be readily determined with the equation $Z^* = V0/I^*$.

The computer 160 of the moisture measurement system 10 includes a data acquisition device or card 170 to generate an excitation signal waveform for transmitting to each of the various capacitors 17. Subsequently, for measuring a response from any one of the capacitors 17, the computer 160 utilizes the data acquisition card 170 for digitizing the voltage waveform across the load resistor 140, via the amplifiers 145 in the sensor measurement unit 190, as one of ordinary skill in the art will understand. Subsequently, values corresponding to attenuation measurement, phase measurement, demodulation, etc. can be computed digitally in a demodulation software component 200, and from such values, this component 200 then computes corresponding impedance data (specifically, the parallel capacitance of the lumber). In particular, the demodulation component 200 uses values (denoted "calibration parameters" herein) stored in the calibration parameter storage 204 for adjusting "raw" or uncorrected impedance values that include cabling 78a,b impedances. More specifically, such calibration parameters are retrieved or fetched from the calibration parameter storage 204, and used to adjust such uncorrected impedance values so that the resulting adjusted impedances are substantially independent of variations in the cabling 78a,b lengths between channels, and more preferably so that such adjusted impedances have substantially all impedance due to the cabling 78a,b removed.

Depending on the electrical configuration of the impedance sensor circuit 125, the calibration parameter storage 204 may store different sets of calibration parameters, wherein such parameters are computed in a calibration process prior to initiation of a lumber stack moisture monitoring process. Various calibration techniques/methods are disclosed hereinbelow for generating the sets of calibration parameters. For example, for the moisture measurement system 10 of FIG. 1A, two different sets of such calibration parameter sets may be determined depending upon whether the cabling shield 90 is excited or grounded. For cabling 78a,b having excited shields 90, the following calibration parameters may be stored in the calibration parameter storage 204, wherein they can be retrieved for correcting uncorrected impedance values: a terminal impedance, an impedance gain, an offset, a phase gain, and a phase offset. For cabling 78a,b having grounded shields 90, the following calibration parameters may be stored in the calibration parameter storage 204, wherein they can be retrieved for correcting uncorrected impedance values:

(a) a terminal impedance (Zterm herein), (b) a capacitance to ground (Ccable herein) of the cabling 78a,b and intervening components (e.g., the multiplexer unit 70); in particular, the capacitance here includes the capacitance between a grounded shield 90 and the corresponding center wire 80 surrounded by the grounded shield, (c) an impedance gain (Zgain herein) of the cabling 78a,b and intervening components, (d) an impedance offset (Zoffset herein) of the cabling 78a,b and intervening components, (e) a phase gain (Phasegain) of the cabling 78a,b and intervening components, (f) a phase offset (Phaseoffset) of the cabling 78a,b and intervening components, (g) an inductance (Lcable herein) of the cabling 78a,b and intervening components, and (h) a resistance (Rcable herein) of the cabling 78a,b and intervening components.

Moreover, as described hereinbelow, for alternative embodiments of the moisture measurement system 10 such as those shown in FIGS. 1B and 1C, their corresponding calibration parameter storage 204 may include a different set of calibration parameters as described hereinbelow, and a different calibration technique/method may be utilized to determine the different sets of calibration parameters as is also described hereinbelow.

Returning now to the demodulation component 200, the corrected or adjusted impedance data is computed, and this component outputs the corrected or adjusted impedance data to a kiln moisture analysis component 210. Accordingly, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

Second Embodiment (FIG. 1B): Kiln Moisture System 11 Using A Bridge Circuit

An alternative second embodiment of the moisture measurement system 10 is shown in FIG. 1B, wherein the circuit 125 is configured as a bridge circuit (and referred as a "bridge circuit" herein), as one skilled in the art will understand. In particular, in FIG. 1B, the bridge circuit 125 for a particular channel includes the sensor measurement unit 190, the cabling 78a, the multiplexer unit 70 (if any is provided), the cabling 78b for the channel, and a capacitor 17 for the channel wherein the capacitor is connected to the channel's cabling 78b. Although the present embodiment of FIG. 1B is similar to the system described in FIG. 1A, the bridge circuit 125 includes a substantially different sensor measurement unit 190. In particular, the circuit 125 is configured as a balanced bridge where the ratio of impedances Z1 and Z3 is compared to the ratio of impedances Z2 and Z4, and wherein Z4 is the impedance of one of the capacitors 17. When these two ratios are equal, i.e., when the bridge is balanced, there is little or no current flow across a load resistor Z5, and therefore the voltage measured by the amplifier 252 will be at or near zero.

A calibration component 205 is also provided for receiving impedance load data (via the data acquisition device/card 170) output by the impedance sensor circuit 125. The calibration component 205 is, in one embodiment, a software module or subsystem that decomposes the impedance load data into its parallel reactive and resistive components as one of ordinary skill in the art will understand. Further, the calibration component 205 removes impedances and inaccuracies in the impedance readings in the form of impedances from cabling (Ccable, etc). Thus, the main purpose of the calibration component 205 processing is to ensure that the final output impedances (especially the capacitance) accurately represents the moisture content in the drying lumber.

The present embodiment of the moisture measurement system 10 works by continually providing a signal (denoted the "null signal") from the data acquisition card 170 to the variable impedance component 149. The variable impedance component 149 may be an electronically controlled capacitor. One such electronically controlled capacitor is the Intersil X90100 electronically programmed capacitor, produced by the Intersil Corporation, 1001 Murphy Ranch Road, Milipitas, Calif. 95035. However, other similarly controlled capacitors may also be used as one of ordinary in the art will understand. The null signal is used to continually adjust the output (Z3) of the variable impedance component 149 in order to maintain a balanced bridge, i.e., to maintain the voltage across the load resistor Z5 at or near zero volts (e.g., within ±0.1 volts). A parallel electronically programmed resistor (also known as a potentiometer) can also be used as part of the component 149 to further balance the bridge and accurately determine the resistance at the circuit point where impedance Z4 is measured. The present embodiment of the moisture measurement system 10, the data acquisition card 170 determines an accurate (or corrected) capacitance of a capacitor 17 by using feedback signals from the amplifiers 252 for determining what capacitance level (at component 149) is required to balance the bridge, and then multiplying this capacitance level by the ratio of Z2/Z1. In the circuit configuration of FIG. 1B, each shield 90 of the coaxial cabling can be grounded, and therefore only a single coaxial cable 78b is required for each pair of sensor plates in a particular capacitor 17. Note that in the present embodiment of the moisture measurement system 10, the data acquisition card 170 accesses the calibration parameters in the calibration parameter storage 204 for computing the adjusted or corrected impedance data that is then provided to the kiln moisture analysis component 210.

For the bridge circuit 125 of FIG. 1B, the calibration parameter storage 204 stores calibration parameters, wherein such parameters are computed in a calibration process prior to initiation of a lumber stack moisture monitoring process. In particular, various combinations of the following calibration parameters may be stored in the calibration parameter storage 204, wherein they can be retrieved for correcting uncorrected impedance values:

(a) a capacitance (Ccable herein) to ground of the cabling 78a,b and intervening components (e.g., the multiplexer unit 70); in particular, the capacitance here include the capacitance between a grounded shield 90 and the corresponding center wire 80 surrounded by the grounded shield, (b) an impedance gain (Zgain herein) of the cabling 78a,b and intervening components, (c) an impedance offset (Zoffset herein) of the cabling 78a,b and intervening components, (d) a phase gain (Phasegain herein) of the cabling 78a,b and intervening components, (e) a phase offset (Phaseoffset herein) of the cabling 78a,b and intervening components, (f) an inductance (Lcable herein) of the cabling 78a,b and intervening components, and (g) a resistance (Rcable herein) of the cabling 78a,b and intervening components.

Third Embodiment (FIG. 1C): Kiln Moisture System 11 Using LCR Data Acquisition Device 171

A third alternative embodiment of the moisture measurement system 10 is shown in FIG. 1C. In this third embodiment, a LCR data acquisition device (card) 171 to generate an excitation signal waveform for transmitting to each of the various capacitors 17 is provided, wherein this card is specifically designed to output inductance (L), capacitance (C), and resistance (R) of a circuit when the card is attached to an impedance load. A LCR data acquisition card 171 for use in the present moisture measurement system 10 embodiment may be obtained from National Instruments Corporation, 11500 North Mopac Expressway, Austin, Tex. 78759 as National Instruments PXI-4072 Flex DMM and LCR meter part number 778270-01.

A calibration component 205 is also provided for receiving impedance load data (via the LCR data acquisition device 171) output by the impedance sensor circuit 125. The calibration component 205 is, in one embodiment, a software module or subsystem that decomposes the impedance load data into its parallel reactive and resistive components as one of ordinary skill in the art will understand. Further, the calibration component 205 removes impedances and inaccuracies in the impedance readings in the form of impedances from cabling (Ccable, etc). Thus, the main purpose of the calibration component 205 processing is to ensure that the final output impedances (especially the capacitance) accurately represents the moisture content in the drying lumber.

Note that this third embodiment of the moisture measurement system 10 is similar to the previous embodiments of the moisture measurement system 10 described in FIGS. 1A and 1B. However, the data acquisition card 170 of the previous embodiments is replaced with the LCR data acquisition card 171. Moreover, the sensor measurement unit 190 is removed from the present embodiment of the moisture measurement system 10 due to the fact that the sensor measurement function (and its components, e.g., amplifiers 145 or 252) is integral to the LCR data acquisition card 171. Further, since the output of the card 171 is in the form of impedance (and/or capacitance, resistance, or inductance), demodulation of the signal is not required, and accordingly the demodulation component 200 is also removed from the present moisture measurement system 10 embodiment. Note that in the present embodiment of the moisture measurement system 10, the LCR data acquisition card 171 accesses the calibration parameters in the calibration parameter storage 204 for computing the adjusted or corrected impedance data that is then provided to the kiln moisture analysis component 210. Further note that for each capacitor 17, the present embodiment may require two leads, e.g., two coaxial cable center conductors 80 from a pair of cables 78b, wherein one center conductor from each of the paired cables 78b (shown in FIG. 1C) connects to one of the plates of the capacitor 17. Additionally, there are two cables 78a, the center wire 80 from each of the cables 78a communicating with a corresponding unique one of the cables 78b of each cable pair contacting the sensor plates for each one of the capacitors 17. The additional cabling of the present embodiment is due to fact that neither of the capacitor plates of a sensor 17 is grounded.

As in the previous embodiments of FIGS. 1A and 1B of the moisture measurement system 10, the coaxial shields 90 are grounded in the embodiment of FIG. 1C.

For the embodiment of FIG. 1C, the calibration parameter storage 204 stores calibration parameters, wherein such parameters are computed in a calibration process prior to initiation of a lumber stack moisture monitoring process. In particular, various combinations of the following calibration parameters may be stored in the calibration parameter storage 204, wherein they can be retrieved for correcting uncorrected impedance values:

(a) a capacitance to ground of the cabling (Ccable) 78a,b and intervening components (e.g., the multiplexer unit 70); in particular, the capacitance here include the capacitance between a grounded shield 90 and the corresponding center wire 80 surrounded by the grounded shield, (b) an impedance gain (Zgain) of the cabling 78a,b and intervening components, (c) an impedance offset (Zoffset) of the cabling 78a,b and intervening components, (d) a phase gain (Phasegain) of the cabling 78a,b and intervening components, (e) a phase offset (Phaseoffset) of the cabling 78a,b and intervening components, (f) an inductance of the cabling (Lcable) 78a,b and intervening components, and (g) a resistance of the cabling (Rcable) 78a,b and intervening components.

The three embodiments of the moisture measurement system 10 described in FIGS. 1A, 1B, and 1C are only illustrative, and additional embodiments for determining the moisture of lumber with a kiln 15 are also considered to be within the scope of the present disclosure. In particular, corresponding analog moisture measurement systems may be considered within the scope of the present disclosure.

A key technical challenge in effectively operating an embodiment of the moisture measurement system 10 is to appropriately compensate for signal anomalies that can be generated within potentially long lengths of the coaxial cables 78a and/or 78b (e.g., lengths greater than 50 linear feet, more particularly from 51 linear feet to 1,000 linear feet or more). In particular, calibration techniques/methods are herein disclosed for compensating or factoring out such signal anomalies. The calibration methods described hereinbelow are suitable for use with one or more of the above described embodiments of the moisture measurement system 10. Note that each calibration method provided below is directed to calibrating based on a particular circuit model. Accordingly, such circuit models are also described so that the parameters for their corresponding calibration methods can be identified.

(1) Resistor-Capacitor Network (RCN) Calibration Method

The first calibration method is for calibrating the moisture measurement system 10 response (from each of the capacitors 17) as a response from a high precision resistor-capacitor network circuit. This first calibration method is most readily applicable to the voltage divider configuration of FIG. 1A, and is based on the circuit models of FIGS. 3A and 3B. Note, however, the present calibration method may be applied to other circuit models as well such as the bridge circuit or LCR metering method, as one of ordinary skill in the art will appreciate from the description hereinbelow. For each of the capacitors 17, the following additional components are modeled in FIGS. 3A and 3B: the sensor measurement unit 190 (more particularly, the amplifiers 145), the switch 100, the cable 78a, the multiplexer unit 70, and the cable 78b to the capacitor 17. By using the circuit models of FIGS. 3A or 3B, adjustments to the capacitance readings from the capacitor 17 can be determined for more accurately measuring the actual capacitance of the capacitor 17. The adjustments are made via a set of impedance gains and offsets that are applied to the uncorrected impedance data from the circuit of FIG. 1A (as modeled in circuit models 3A or 3B), wherein there are distinct adjustments corresponding to each capacitor 17. In particular, for each capacitor 17, the gains and offsets are presumed to counter act or cancel signal anomalies generated by the following components: the cable 78a, the switch 100, the multiplexer unit 70, and the cable 78b connecting to the capacitor 17.

(1.1) RCN Calibration Method for Voltage Divider Circuit with Excited Shield (FIGS. 1A and 3A)

Referring to the circuit model 204 shown in FIG. 3A (annotated with the corresponding component labels from FIG. 1A), the coaxial shield 90 for each of the cables 78a and 78b is excited rather than grounded, meaning that an AC voltage is applied to the coaxial shield 90; e.g., a voltage such as 1 Vac pk-pk. In particular, each coaxial cable 78a and 78b in the circuit model 204 (and in the corresponding cabling of FIG. 1A) has its shield 90 signally connected to one side of the load resistor 140, and each cable's coaxial center wire 80 is signally connected to the other side of this load resistor. Each of the coaxial cables 78a and 78b has a corresponding capacitance between the cable's center wire 80 and shield 90 of, e.g., typically 10-25 picoFarads per linear foot (pF/ft) for at least some types of coaxial cable. Accordingly, the connection of the shields 90 and the center wires 80 to the load resistor 140 adds a capacitance (identified as "Ccable" in FIG. 3A) in parallel with the resistance of the load resistor 140 (also identified as "Rterm" in FIG. 3A), and this capacitance is dependent on the length of the cabling 78a,b, and is both determined and accounted for by the present calibration method. For example, if the coaxial cables 78a and 78b typically generate 20 pF/ft, and the total cable run of 78a and 78b is 200 ft long, an excited coaxial shield 90 for such cabling will add 4000 pF in parallel with the resistance of the load resistor 140. When this first calibration method is used in calibrating for the coaxial cables 78a and 78b (for a single capacitor 17), and thereby determining an accurate impedance added by this cabling, the impedance across the amplifiers' 145 terminals 208 and 212 (FIG. 3A) (i.e., the parallel combination of the cable capacitance (Ccable) and the resistance of the load resistor 140) is therefore defined. This impedance across the amplifiers' 145 terminals (208 and 212 in FIG. 3A) is referred to herein as "terminal impedance", and also identified by the identifier Zterm hereinbelow. That is, terminal impedance is the ratio of voltage to current across the amplifiers' 145 terminals, when an electrical load is applied.

Once Zterm is determined, the impedance load (Zload hereinbelow) corresponding to the impedance of the capacitor 17 (e.g., FIG. 3A) may then be determined at any time by the equation:

$$Zload = (Zterm * V0)/(V1 - V0),$$

wherein V1 and V0 are voltages as described with reference to the description of FIG. 1A (and as also identified in FIGS. 3A and 3B).

Proper determination of the terminal impedance Zterm is the most critical step in the present calibration method. If performed properly, the determination of an accurate terminal impedance will make the Zload value very accurate. Note that the computed Zload value will be effectively linear to the actual impedance/capacitance load placed on the end of the cable 78b connected to the capacitor 17 (or alternatively, a calibration device as described hereinbelow). That is, Zload is proportional to the actual impedance/capacitance, and independent of the length of the cabling for the channel. However, other minor electrical effects in the modeled circuitry can also be further corrected by subsequently performing a two-point calibration. Such two-point calibration applies small gain and offset corrections to further correct the output of the modeled circuitry, as one of ordinary skill in the art will understand. These other minor electrical effects may include a small amount of cable resistance, cable inductance, and/or an apparent phase inaccuracy caused by digital sampling delays, as one of ordinary skill in the art will understand.

A flowchart of the steps performed for the resistor-capacitor network calibration method is provided in FIGS. 4A through 4D. The description provided in FIGS. 4A-4D is specifically applicable to the excited shield embodiment of the voltage divider circuit model shown in FIG. 3A. Referring to FIG. 1A, the present calibration method may be performed via activation of a software (or hardware) calibration routine provided on the computer 160. This calibration routine is in signal communication with an electronic device (a "calibration box" herein,) having high precision resistors and capacitors for generating a plurality of different standardized impedance loads. FIG. 8 shows an embodiment of such a calibration box 704.

During the calibration of the circuit (as in FIG. 3A), the capacitor 17 of the circuit is replaced by the calibration box 704. More specifically, the center wire 80 (of the cable 78b) that would otherwise signally connect to a sensor plate (e.g., 20 or 40 in FIG. 1A) of the capacitor 17, instead, signally connects to a first connection 708a of a pair of connections 712 on the calibration box, and the shield 90 surrounding this center wire 80 is not connected to the calibration box 704. In one embodiment, the calibration box 704 includes circuitry for generating a set of six different impedance/capacitance loads which can be placed in the Zload position of the circuit model 204 (FIG. 3A). Each of these six impedance loads has a different pair of connections (i.e., 708a, 708b, 708c, 708d, 708e, and 708f), e.g., each connection pair may be provided as a Bayonet Neill-Concelman (BNC) connector mounted on the front of the calibration box 704.

When the calibration routine is started for determining or calibrating the capacitance generated by the cables 78a and 78b for a particular capacitor 17 circuit, the routine prompts the user to connect the BNC connector on the end of the cable 78b end (that would otherwise connect to a sensor plate) to a first of the mating BNC connectors (708a) of the calibration box for determining the terminal impedance (Zterm). A description of the steps of the flowchart of FIGS. 4A through 4D follows.

Step 301: The present step determines the terminal impedance, Zterm. In substep 301a, the coaxial cables 78a and 78b to be calibrated are attached (via cable 78b) to the first BNC connector 708a of the calibration box 704. Subsequently, the calibration box 704 (via BNC connector 708a) provides a first capacitive or impedance load of the standardized loads to the cables as a Zload (FIG. 3A). In one embodiment, this first capacitive load may be nominally a 1000 pF capacitive load, although other capacitive or impedance loads may be used, e.g., in the range of 100-5000 pF. In substep 301b, the voltage is measured across the load resistor 140. Thus, the voltage difference V1−V0 can be obtained. Since the voltage V1 is known (it is known and provided via switch 100), it is now straightforward to determine V0. Further, since the capacitive load (Zload) is known (e.g., the 1000 pF capacitive load of the standard impedance loads provided by the calibration box 704), in substep 301c, the terminal impedance (Zterm) is determined by the equation:

$$Zterm = Zload * (V1 - V0)/V0 \quad \text{(Equation A)}.$$

At the conclusion of step 301, an accurate terminal impedance is stored in a data file DF for later use (note, in at least one embodiment, DF may be the calibration parameter storage 204). Note that the value of Zterm is used with subsequently determined values of Zload as described hereinbelow.

Step 302 The present step applies a predetermined high impedance load to the circuit being calibrated, and then computes a load value ("Zload1") for this high impedance load using the Zterm value determined above. In substep 302a, the user is prompted to connect the cable 78b end (for connecting to the to the calibration box) to a second BNC connection 708b of the calibration box 704 for applying a high impedance standard load to the circuit of FIG. 3A (with the capacitor 17 replaced by the calibration box); i.e., the cables 78a, 78b, the switch 100, the multiplexer unit 70, and the load resistor 140.

Accordingly, the cable 78b is attached to the calibration box high impedance load in the range of 5 to 100 Mohms, such as, e.g., a nominal 10 Mohm resistor. In substep 302b, the voltage is then measured across the load resistor 140 in the manner of substep 301b. In substep 302c, the value, "Zload1(uncorrected)", is determined from the equation:

$$Zload1(uncorrected)=(Zterm*V0)/(V1-V0).  \quad \text{(Equation B)}$$

Note that Zload1(uncorrected) is an uncorrected load measurement of the high impedance load; i.e., Zload1(uncorrected) is a measurement of the total impedance of generated by: the calibration box 704, the connected cables 78a,b, and the multiplexer unit 70. Typically, for a value of 10 Mohm load (provided by the calibration box 704), an uncorrected load may be roughly 10.5 Mohms, as one of ordinary skill in the art will understand. At the conclusion of step 302, the uncorrected Zload1 is stored to the data file DF.

Step 303 The present step applies a predetermined low impedance load to the circuit being calibrated, and then computes a value for this impedance load using the Zterm value determined above. In substep 303a, the user is prompted to connect the appropriate cable 78b end to a third BNC cable connection 708c for obtaining a next impedance standard load from the calibration box 704. Such a predetermined low impedance load may be approximately a nominal 1 Mohm resistance (although loads in the range of 0.1 to 2.0 Mohms may be used). Subsequently in substep 303b, when the cable 78b is connected to the predetermined low impedance load of the calibration box 704, the voltage is then determined across the load resistor 140, again, in the manner of substep 301b. In substep 303c, the value "Zload2(uncorrected)" is determined through the equation:

$$Zload2(uncorrected)=(Zterm*V0)/(V1-V0).  \quad \text{(Equation C)}$$

Note that Zload2(uncorrected) is an uncorrected load measurement of the low impedance load; i.e., Zload2(uncorrected) is a measurement of the total impedance generated by the calibration box 704, the connected cables 78a,b, and the multiplexer unit 70. Typically, for a value of a 1 Mohm load (provided by the calibration box), an uncorrected load may be approximately 1.2 Mohms. At the conclusion of step 303, the uncorrected Zload2 is stored to the data file DF.

Step 304 The present step determines a set of at least one signal gain adjustment, and at least one signal offset adjustment to correct the uncorrected impedance values of "Zload1(uncorrected)" and "Zload2(uncorrected)". That is, the equations for these corrections are as follows:

$$Zgain=[Zload1(corrected)-Zload2(corrected)]/[Zload1(uncorrected)-Zload2(uncorrected)]  \quad \text{(Equation D)}$$

$$Zoffset=Zload1(corrected)-[Zload1(uncorrected)*Zgain],  \quad \text{(Equation E)}$$

where: "Zgain" is the impedance gain to be applied to uncorrected impedance measurements, "Zload1(corrected)" is the known predetermined impedance load provided by the calibration box 704 in step 302, "Zload2(corrected)" is the known predetermined impedance load provided by the calibration box in step 303, and "Zoffset" is the offset to be applied to uncorrected impedance measurements.

For example, if the value of Zload1(uncorrected) is 10.5 Mohms, as estimated above, for an actual load of 10 Mohms (i.e., "Zload1(corrected)" here), and if the value of Zload2(uncorrected) is 1.2 Mohms for an actual load of 1 Mohms (i.e., "Zload2(corrected)" here), then typical gains and offsets may be computed as follows:

$$Zgain=(10.0-1.0)/(10.5-1.2)=0.97, \text{ and}$$

$$Zoffset=(10.0)-(10.5*0.97)=-0.19 \text{ Mohms}.$$

At the conclusion of step 304 of FIG. 4B, the Zgain and Zoffset are stored to the data file DF or the calibration parameter storage 204.

Step 305 The present step applies a high phase load (e.g., a nominal 100 pF capacitance with a nominal −90 degree phase angle) to the circuit being calibrated, and then computes a value for this load using the Zterm value determined above. In substep 305a, the user is prompted to connect the cable 78b end (for connecting to the to the calibration box 704) to a fourth BNC cable connection 708d for obtaining a fourth impedance standard load from the calibration box 704. Such a predetermined high phase load may be in the range of 1 to 1000 pF. Subsequently, when the cable 78b is connected to the predetermined high phase load of the calibration box 704, in substep 305b, the voltage is determined across the load resistor 140 as V1−V0, again, in the manner of substep 301b. The uncorrected phase angle of the load (identified as "Phaseload3(uncorrected)" herein) is then computed in substep 305c by measuring how many degrees of phase difference exist between the differential voltage signal V1−V0, and the excitation voltage V1. The uncorrected phase angle determination can be performed through a wide variety of methods, including trigonometric methods, Fourier Transform, zero crossing method, etc., as one of ordinary skill in the art will understand.

Note that since Phaseload3(uncorrected) is an uncorrected measurement of the high phase load, Phaseload3(uncorrected) is a measurement of the total phase angle of generated by the calibration box 704, the connected cables 78a,b, and the multiplexer unit 70. Also note that the corrected phase angle ("Phaseload3(corrected)" herein) is −90 degrees since the load is a capacitance, as is well known in the art. Typically, an uncorrected value of an actual nominal 100 pF capacitance with a nominal −90 degree phase angle may be approximately −88 degrees. At the conclusion of step 305, the value of "Phaseload3(uncorrected)" is stored to the data file DF, or the calibration parameter storage 204.

Step 306 The present step applies a low phase load (e.g., a load of 1 Mohm with a nominal 0 degree phase angle). In substep 306a, the user is prompted connect the appropriate cable 78b end to a fifth BNC cable connection 708e for obtaining a fifth impedance standard load from the calibration box 704. Such a predetermined low phase load may be in the range of 1 to 10 Mohms. Subsequently, when the cable 78b is connected to the predetermined low phase load of the calibration box 704, in substep 306b, the voltage is then measured across the load resistor 140 as V1−V0 in the manner of substep 301b. The phase angle of the load (identified as "Phaseload4(uncorrected)" herein) is then computed in Substep 306c by measuring how many degrees of phase difference exist between the differential voltage signal V1−V0 and the excitation voltage V1.

Note that "Phaseload4(uncorrected)" is an uncorrected measurement of the low phase load; i.e., Phaseload4(uncorrected) is a measurement of the total phase angle of generated by the calibration box 704, the connected cables 78a,b, and the multiplexer unit 70. Also note that the corrected phase load ("Phasesload4(corrected)" herein) is 0 degrees since the load is a resistance. Typically, an uncorrected value of a load of 1 Mohm with a nominal 0 degree phase angle for the low phase load may be roughly −1.5 degrees. At the conclusion of step 306, the value of "Phaseload4(uncorrected)" is stored to the data file DF.

Step 307 The present step determines a set of values, including a phase gain and a phase offset to correct or adjust uncorrected phase loads received via the channel cabling 78a,b, e.g., Phaseload3(uncorrected) and Phaseload4(uncorrected). In particular, the set includes a phase gain (denoted "Phasegain" herein), and a phase offset (denoted "Phaseoffset" herein). Note that, as indicated above, Phaseload3(corrected) is −90 degrees since the load is a capacitance, and Phasesload4(corrected) is 0 degrees since the load is a resistance. Accordingly, the equations for correcting Phaseload3(uncorrected) and Phaseload4(uncorrected) are as follows:

Phasegain=[Phaseload3(corrected)−Phaseload4(corrected)]/[Phaseload3(uncorrected)−Phaseload4(uncorrected)]    (Equation F)

Phaseoffset=Phaseload3(corrected)−[Phaseload3(uncorrected)*Phasegain],    (Equation G)

wherein Phaseload3(corrected) is the known predetermined phase angle provided by the calibration box 704 in step 305, and Phaseload4(corrected) is the known predetermined capacitance load phase angle provided by the calibration box in step 306.

For example, if the value of Phaseload3(uncorrected) is −88 degrees, as indicated above, for an actual value of a nominal 100 pF capacitance with a nominal −90 degree phase angle (i.e., "Phaseload3(corrected)" here), and if the value of Phaseload4(uncorrected) is −1.5 degrees, as estimated above, for an actual load of 1 Mohm with a nominal 0 degree phase angle (i.e., "Phaseload4(corrected)" here), then typical gains and offsets may be computed as follows:

Phasegain=(−90−(0)/(−88−(−1.5))=1.04,

Phaseoffset=(−90)−(−88)*1.04=1:5 degrees

At the conclusion of step 307, the computed values for Phasegain and Phaseoffset are stored to the data file DF.

Figure 9:
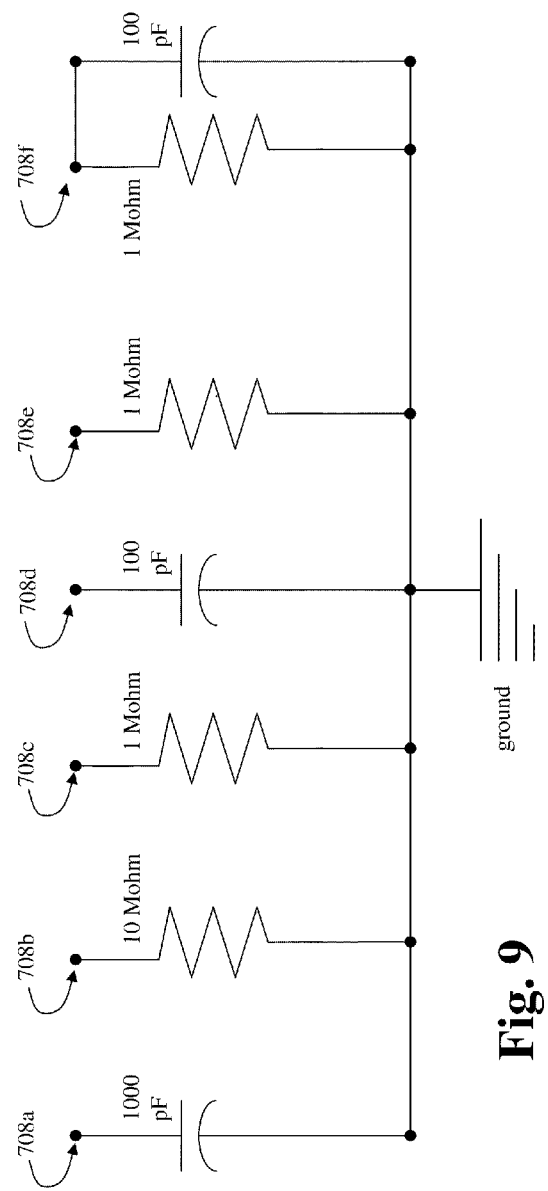
FIG. 9 shows a high level circuit diagram of the calibration box 704.

Step 308 In the present step, the calibration parameters Zterm, Zgain, Zoffset, Phasegain, and Phaseoffset are tested to determine if they can be used to appropriately calibrate signals arriving at the amplifiers 145 so that signal characteristics generated by the cables 78a and 78b (and other electrical components) can be effectively removed, thereby leaving substantially only signal characteristics obtained from the calibration box 704. In particular, one or more tests are conducted using the calibration box 704, wherein for each known impedance load (Zload, FIG. 3A) provided by the calibration box, a measurement for this impedance load is compared with a corresponding impedance load value computed using the values V0, V1, and the stored calibration parameters (in DF) obtained from steps 301 through 307 (i.e., Zterm, Zgain, Zoffset, Phasegain, and Phaseoffset). If the difference between these impedance load values is within a predetermined tolerance for all tests, then the calibration parameters are presumed to be sufficiently reliable to be used in lumber drying operations for substantially cancelling out electrical signal characteristics that are generated during signal transmission, and for retaining electrical signal characteristics generated by one of the capacitors 17 replacing the calibration box 704. The substeps 308a through 308e provide further details of the substeps that may be iteratively performed. In substep 308a, the user is prompted to attach the sensor connection end of the cable 78b to a sixth BNC connection 708f on the calibration box 704 for applying a sixth predetermined load (denoted Zload5 herein) to the cables 78a and 78b, and the load resistor 140. The sixth BNC connection 708f may provide a load from a parallel combination of, e.g., a nominal 100 pF capacitor and a nominal 1 Mohm resistor (FIG. 9), although an alternative capacitance in the range of 10 to 1000 pF and a corresponding resistance in the range of 0.1 to 100 Mohm may be used. In substep 308b, the voltages V1 and V0 are read across the load resistor 140 in the manner of substep 301b. In substep 308c, the value of Zterm (stored in DF) is then used with the measured values V0, and V1 to obtain:

(a) an uncorrected impedance load value ("Zload5(uncorrected)" herein) for the circuit of FIG. 3A as described by Equation B above, and (b) an uncorrected phase value ("Phaseload5(uncorrected)" herein) calculated by comparing the phase angle between V0 and V1, as one of ordinary skill in the art will understand.

In substep 308d, the gains and offsets (Zgain, Zoffset, Phasegain, and Phaseoffset in DF) are applied to Zload5(uncorrected) and Phaseload5(uncorrected) for obtaining the corrected impedance and phase values, respectively, Zload5(corrected) and Phaseload5(corrected), according to the following equations:

Zload5(corrected)=Zload5(uncorrected)*Zgain+Zoffset,    (a)

and

Phaseload5(corrected)=Phaseload5(uncorrected)*Phasegain+Phaseoffset.    (b)

In substep 308e, a determination is made as to whether the readings of the known impedance load provided by the calibration box 704, and the impedance load values computed in substeps 308b through 308d (using the calibration parameters Zterm, Zgain, Zoffset, Phasegain, and Phaseoffset) are sufficiently close to one another. In particular, based on a tolerance specified by, e.g., the user (such as within 7% of one another, and more preferably within a range of approximately 5%), a determination is made as to whether or not the calibration of the circuit of FIG. 3A was successful for the current test. For example if a 5% tolerance is specified as a pass/fail criteria, the computed value of the sixth predetermined capacitance must be within 95 to 105 pF for the sixth predetermined capacitance load being 100 pF. Similarly, a parallel resistance of 1 Mohm should read within 5% tolerance as well, reading from 0.95 Mohm to 1.05 Mohm. With lumber drying applications, capacitance is typically of more interest since it is more related to moisture content. It is believed that for most kiln lumber drying processes, the variance between the actual and computed capacitance loads should be less than 15%, and more preferably less than 10%, and most preferably 5% or less.

If substep 308e does not determine capacitance load values within a specified tolerance of the actual predetermined capacitive load provided by the calibration box 704, then the calibration parameters determined in steps 301 through 307 are not sufficiently effective, and accordingly the steps 301 through 308 are repeated. Note that the connections of the cables 78a,b to their various electrical components should be checked to assure that appropriate electrical connections are provided prior to repeating the steps 301 through 308. If the computed capacitance load value is within the specified tolerance, then the calibration may be determined to be successful.

Step 309: In the present step, the following values are stored in the calibration parameter storage 204 (e.g., a file or database) (FIG. 4D) for the particular channel being calibrated:
(309.1a) Zterm,
(309.2a) Zgain,
(309.3a) Zoffset,
(309.4a) Phasegain, and
(309.5a) Phaseoffset.

Step 312: In the present step, a determination is made as to whether there is another channel to calibrate. If so, then the steps commencing with step 301 are again performed. If not, then the calibration process terminates.

Thus, since steps of FIGS. 4A through 4D are performed for each channel whose cable(s) 78a,b transport signals for the channel, once sufficiently accurate calibration parameters (Zterm, Zgain, Zoffset, Phasegain, and Phaseoffset) are determined and stored for each channel, the calibration box 704 is removed from all channels, and a capacitor 17 is connected to each channel for monitoring the kiln lumber drying process.

Accordingly, during operation of the moisture measurement system 10 configured as a voltage divider with an excited shield 90, for each channel, the following steps are performed:

(Step A-1) The data acquisition card 170 determines a voltage difference (V1−V0), e.g., across the load resistor 140 for the channel being monitored.

(Step A-2) The demodulation component 200 determines an (uncorrected) impedance load for the channel, through application of the equation:

$$Zload(uncorrected) = (Zterm * V0)/(V1 - V0).$$

(Step A-3) The demodulation component 200 determines an (uncorrected) phase of the load across the load resistor 140 by comparing the phase angle of V0 and V1, using trigonometric methods, Fourier transform, or zero crossing methods, as one of ordinary skill in the art will understand.

(Step A-4) The demodulation component 200 uses the calibration parameters (gains and offsets) stored in the calibration parameter storage 204 (i.e., in step 309) to remove errors generated by electrical components other than the capacitor 17 by performing corrections to the total impedance and phase. Equations to perform these corrections are:

$$Zload(corrected) = Zload(uncorrected) * Zgain + Zoffset, \quad (a)$$

and $$Phaseload(corrected) = Phaseload(uncorrected) * Phasegain + Phaseoffset. \quad (b)$$

(Step A-5) With accurate determination of the phase angle and total impedance of the load from step A-4, the demodulation component 200 resolves this corrected impedance into its rectangular components, i.e., the parallel impedances Cload (a capacitance load) and Rload (a resistance load), as one of ordinary skill in the art will understand.

(Step A-6) Since Cload and Rload are substantially independent of the length of the cabling 78a,b, the moisture content of the lumber being monitored (e.g., lumber stack 110 or 120) can be more accurately, determined. Accordingly, the impedances Cload and Rload are provided to the kiln moisture analysis 210 (FIG. 1A) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

Figure 3B:
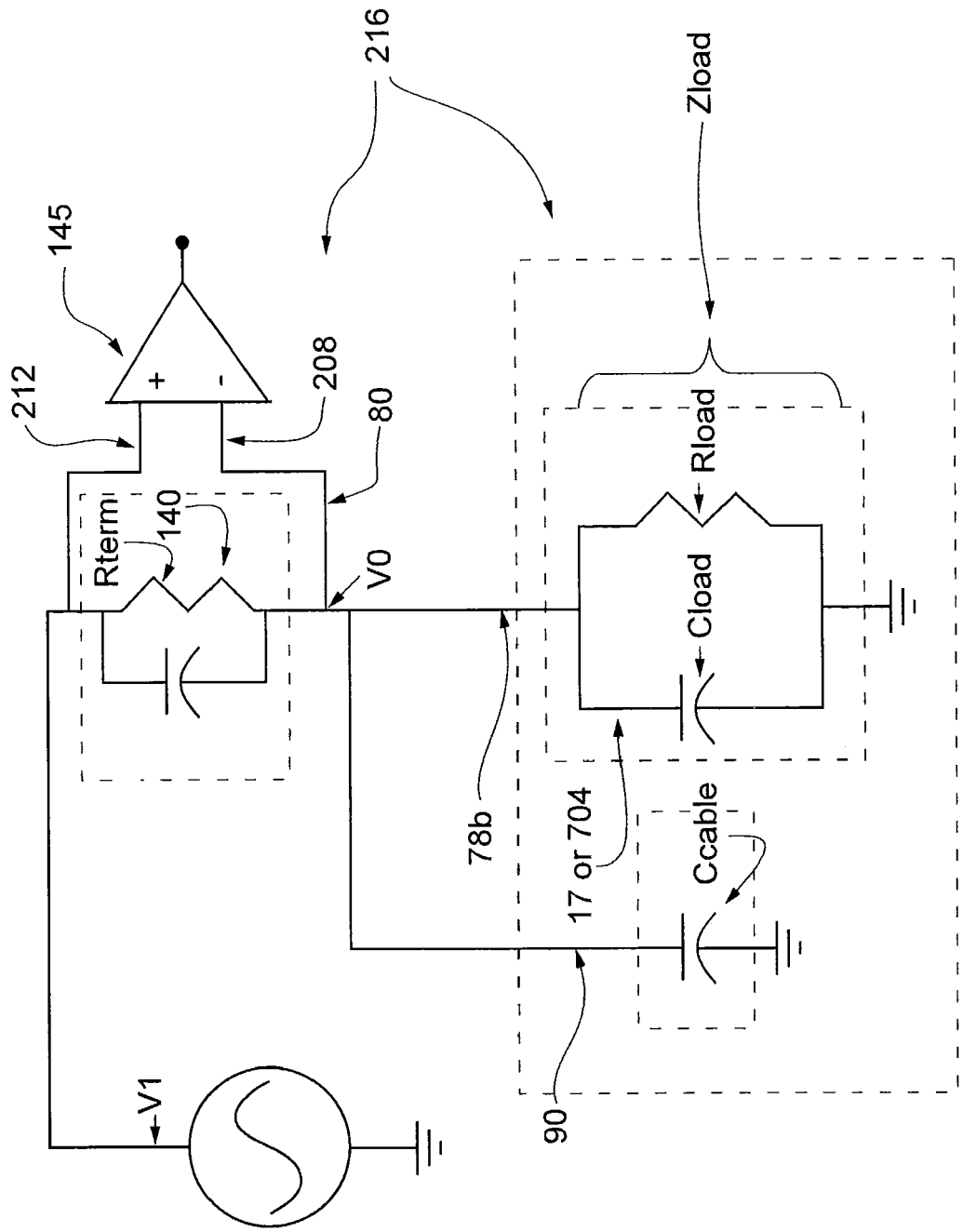
FIG. 3B is a schematic showing the circuit model for the voltage divider metering method with a grounded coaxial shield.

(1.2) RCN Calibration Method for Voltage Divider (VD) Circuit with Grounded Shield (FIGS. 1A and 3B)

Note that for an embodiment of the voltage divider metering of FIG. 1A where the shield(s) 90 is grounded, for each of the channels (between a corresponding one of the capacitors 17 and the computer 160), the calibration of the channel using the resistor-capacitor network calibration method for the grounded shield(s) is modeled by the circuit model 216 in FIG. 3B. Since the present voltage divider metering embodiment has a grounded shield 90, the terminal impedance (Zterm) is known, since it is only the resistance of the load resistor 140. Thus, Zterm does not need to be computed as in step 301, FIG. 4A since it is known. Additionally, note that the variations to steps 301 through 312 for the circuit model 216 includes determining Ccable which is dependent on the length of the cabling 78a,b, and can be computed in step 301 as follows. The first load in the calibration box 704 (e.g., from connector 708a) is a known capacitance, for example a capacitor in the range of 100-5000 pF. When the cable 78b is connected to, e.g., the connector 708a as indicated in Substep 301a, Ccable in this configuration is additive with the capacitance supplied to the cabling by the calibration box 704. Accordingly, Ccable can be calculated by measuring an apparent capacitance at the first BNC connector 708a and then by subtracting the known capacitance, Ccable is determined as follows:

$$Ccable = (Apparent\ Capacitance\ at\ BNC\ connector\ 708a) - (known\ Capacitance\ at\ BNC\ connector\ 708a).$$

The remainder of the calibration parameters (gains and offsets) are then determined in the same fashion and steps as described previously in steps 301-312 using the known value of Zterm. In particular, various impedance loads (e.g., Zload1, Zload2, Zload5) according to the equation impedance load equation: (Zterm*V0)/(V1−V0) for voltages V0 and V1 as shown in FIGS. 1A and 3B.

Accordingly, for the grounded shield 90 embodiment, the calibration parameter storage 204 is provided with the calibration parameter values (309.1b) through (309.6b) below at successful completion of the steps corresponding to the steps 301 through 312.

(309.1b) Zterm, which is approximately equal to the impedance of the load resistor 140.

(309.2b) Cabling capacitance to ground, Ccable (i.e., the capacitance between grounded shield 90 and the corresponding center wire 80 surrounded by the shield),
(309.3b) Zgain,
(309.4b) Zoffset,
(309.5b) Phasegain, and
(309.6b) Phaseoffset,
wherein each term identified here has the same meaning as the (any) corresponding identical term used in describing FIGS. 4A through 4D hereinabove.

Accordingly, during operation of the moisture measurement system 10 configured as a voltage divider with a grounded shield 90, for each channel, the following steps are performed:

(Step B-1) The data acquisition card 170 determines a voltage difference (V1−V0), e.g., across the load resistor 140 for the channel being monitored.

(Step B-2) The demodulation component 200 fetches the calibration parameter Zterm from the calibration parameter storage 204, and determines an (uncorrected) impedance load, Zload(uncorrected) for the channel, through application of the equation:

Zload(uncorrected)=(Zterm\**V*0)/(*V*1−*V*0).

(Step B-3) The demodulation component 200 decomposes Zload(uncorrected) into its parallel reactive and resistive components, Cload(uncorrected) and Rload(uncorrected).

(Step B-4) The demodulation component 200 fetches the cable capacitance (Ccable) from the calibration parameter storage 204, and subtracts this value from the Cload (uncorrected), thereby obtaining a value denoted Cload (uncorrected)$_1$.

(Step B-5) The demodulation component 200 combines the values Cload(uncorrected)$_1$ and Rload(uncorrected) (by transformation to polar coordinates) to obtain a new impedance value denoted Zload(uncorrected)$_1$ that has the cable capacitance removed from it.

(Step B-6) The demodulation component 200 determines an (uncorrected) phase of the load across the load resistor 140 by comparing the phase angle of V0 and V1, using trigonometric methods, Fourier transform, or zero crossing methods, as one of ordinary skill in the art will understand.

(Step B-7) The demodulation component 200 fetches the calibration parameters (e.g., gains and offsets) in the calibration parameter storage 204 (e.g., those identified in (309.1b) through (309.6b) above), and uses these values to remove errors generated by electrical components other than the capacitor 17 by performing corrections to the total impedance and phase. Equations to perform these corrections are:

Zload(corrected)=Zload(uncorrected)$_1$\*Zgain+Zoffset,  (a)

and

Phaseload(corrected)=Phaseload(uncorrected)\*Phasegain+Phaseoffset.  (b)

(Step B-8) With accurate determination of the phase angle and total impedance of the load across the load resistor 140 from step B-7, the demodulation component 200 resolves the impedance into its rectangular components, i.e., the parallel impedances Cload and Rload, as one of ordinary skill in the art will understand.

(Step B-9) Since Cload and Rload are substantially independent of the length of the cabling 78*a,b*, the moisture content of the lumber being monitored (e.g., lumber stack 110 or 120) can be more accurately determined.

Accordingly, the impedances Cload and Rload are provided to the kiln moisture analysis 210 (FIG. 1A) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

Figure 3C:
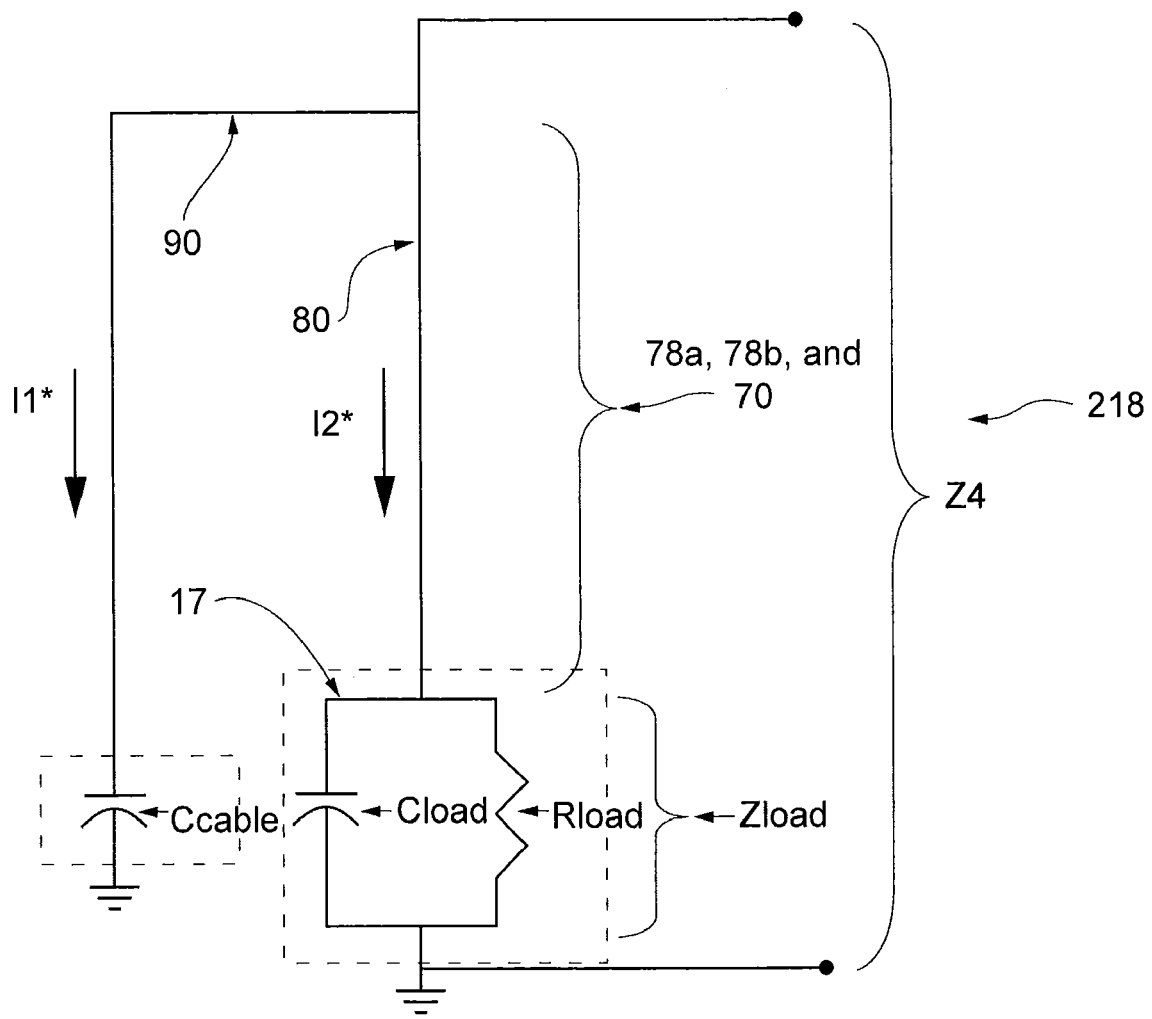
FIG. 3C is a schematic showing the circuit model for the bridge or LCR metering method with a grounded coaxial shield.

(1.3) RCN Calibration Method for Bridge Circuit with Grounded Shield (FIGS. 1B and 3C)

Regarding an embodiment of the bridge metering of FIG. 1B where the shield(s) 90 is grounded, for each of the channels (between a corresponding one of the capacitors 17 and the computer 160), the calibration of the channel using the resistor-capacitor network calibration method is modeled by the circuit model 218 in FIG. 3C. In the present bridge metering embodiment, the terminal impedance (Zterm) is not of critical interest, since the impedances and phases (i.e., Zload1 (uncorrected), Zload2(uncorrected), Phaseload3(uncorrected), Phaseload4(uncorrected), Zload5(uncorrected), Phaseload5(uncorrected)) are determined by balancing the bridge circuit 125 (FIG. 1B), and do not rely on the value of terminal impedance.

However, the cabling 78*a,b* capacitance, Ccable, is needed, wherein Ccable is related to the length of the cabling 78*a,b*. Note that variations to steps 301 through 312 of FIGS. 4A-4D for determining Ccable include enhancing step 301 as follows.

Since the first load of the calibration box 704 (e.g., from BNC connector 708*a*) is a known capacitance, for example a capacitor in the range of 100 to 5000 pF, the Ccable value in the circuit model of FIG. 3C is additive with the capacitance in the calibration box 704. Therefore, the Ccable value can be calculated by measuring an apparent capacitance at the first BNC connector 708*a* (via balancing the bridge circuit 125 of FIG. 1B), and then by subtracting the known capacitance to determine Ccable, as follows:

Ccable=(Apparent Capacitance at *BNC* connector 708*a*)−(known Capacitance at *BNC* connector 708*a*).

The remainder of the calibration parameters (gains and offsets) are then determined in the same fashion and steps as described in FIGS. 4A-4D with the exception that, as mentioned above, (Zload1uncorrected), Zload2(uncorrected), Phaseload3(uncorrected), Phaseload4(uncorrected), Zload5 (uncorrected), and Phaseload5(uncorrected) are computed by balancing the bridge circuit 125.

Accordingly, for the bridge metering embodiment with a grounded shield 90, the calibration parameter storage 204 is provided with the following calibration parameter values at successful completion of the steps corresponding to the steps 301 through 312.

(309.1c) Cabling capacitance to ground, Ccable (i.e., the capacitance between grounded shield 90 and the corresponding center wire 80 surrounded by the shield), wherein Ccable is dependent on the length of the cabling 78*a,b* for the channel being calibrated,
(309.2c) Zgain,
(309.3c) Zoffset, (309.4c) Phasegain, and (309.5c) Phaseoffset, wherein each term identified here has the same meaning as the (any) corresponding identical term used in describing FIGS. 4A through 4D hereinabove. Note, however, that the steps referring to the voltages across the load resistor 140 will in the present embodiment (FIG. 1B) be somewhat different in that the uncorrected voltage and phases will be determined directly by balancing the impedance bridge circuit 125 (FIG. 1B).

Accordingly, during operation of the moisture measurement system 10 configured as a bridge circuit with a grounded shield 90, for each channel, the following steps are performed by the data acquisition card 170:

(Step C-1) A null signal is transmitted to adjust impedance Z3 (FIG. 1B) such that the bridge circuit 125 is balanced, i.e., such that the voltage across Z5 is maintained near zero volts (e.g., within a range of approximately −0.1 to +0.1 volts).

(Step C-2) The values of the balancing impedance (Z3) as well as the impedance values of Z2 and Z1 are recorded by the data acquisition card 170.

(Step C-3) Z4 is calculated according to the equation:

$$Z4 = Z3 * Z2/Z1.$$

The impedance Z4 is transmitted to the calibration component 205.

(Step C-4) Z4 is decomposed into its parallel reactive and resistive components, Cload(uncorrected) and Rload (uncorrected) by the calibration component 205.

(Step C-5) The cable capacitance (Ccable) is fetched from the calibration parameter storage 204, and is subtracted from Cload(uncorrected) by the calibration component 205. This provides a new value denoted Cload(uncorrected)$_1$ herein.

(Step C-6) Cload(uncorrected)$_1$ and the Rload(uncorrected) are combined by the calibration component 205 to yield a new impedance value denoted Zload(uncorrected)$_1$ that has the cabling 78a,b capacitance removed from it.

(Step C-7) The calibration component 205 determines an uncorrected phase ("Phaseload(uncorrected)") of the impedance load (e.g., for the lumber 110 or 120) by evaluation of the real and imaginary portions of the complex impedance Z4, i.e., by converting the rectangular components of Z4's resistance and reactance into polar coordinates, the phase of which can be readily determined.

(Step C-8) The calibration parameters (gains and offsets) in the calibration parameter storage 204 (i.e., identified in (309.7b) through (309.11b) above) are used, by the calibration component 205, to remove errors generated by electrical components other than the capacitor 17 by performing corrections to the total impedance and phase. Equations to perform these corrections are:

$$Zload(corrected) = Zload(uncorrected)_1 * Zgain + Zoffset, \quad (a)$$

and $$Phaseload(corrected) = Phaseload(uncorrected) * Phasegain + Phaseoffset. \quad (b)$$

(Step C-9) With accurate determination of the phase angle and total impedance of the load, the calibration component 205 resolves the impedance into rectangular components, i.e., the parallel impedances Cload and Rload, as one of ordinary skill in the art will understand.

(Step C-10) Since Cload and Rload are substantially independent of the length of the cabling 78a,b, the moisture content of the lumber being monitored (e.g., lumber stack 110 or 120) can be more accurately determined. Accordingly, the impedances Cload and Rload are provided to the kiln moisture analysis 210 (FIG. 1B) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(1.4) RCN Calibration Method for LCR Data Acquisition Circuit, Grounded Shield (FIGS. 1C and 3C)

Note that for an embodiment of the LCR data acquisition circuit 125 of FIG. 1C where the shield(s) 90 is grounded, for each of the channels (between a corresponding one of capacitors 17 and the computer 160), the calibration of the channel using the resistor-capacitor network calibration method is modeled by the circuit model 218 in FIG. 3C. In the LCR data acquisition circuit 125 embodiment of FIG. 1C, the terminal impedance (Zterm) is a value internal to the LCR metering equipment (i.e., the LCR data acquisition device/card 171), and its value has already been factored into the output of the device/card 171. Thus, Zterm does not need to be computed as in step 301, FIG. 4A. Additionally, note that the variations to steps 301 through 312 include determining Ccable which is dependent on the length of the cabling 78a,b, and can be computed in step 301 as follows. Since the first load in the calibration box 704 (e.g., from connector 708a) is a known capacitance, for example a capacitor in the range of 100-5000 pF, Ccable in this configuration is additive with the capacitance in the calibration box 704. Therefore, Ccable can be calculated by measuring an apparent capacitance at the first BNC connector 708a, and then subtracting the known capacitance to determine Ccable, as follows:

$$Ccable = (Apparent\ Capacitance\ at\ BNC\ connector\ 708a) - (known\ Capacitance\ at\ BNC\ connector\ 708a).$$

A key difference between the present calibration method and the previous calibration methods of (1.1) and (1.2) is that in the present calibration method there is no longer any calculation of uncorrected impedances using voltages and the terminal impedance Zterm. The impedance of the circuit 218 (FIG. 3C) is a direct output of the LCR Data Acquisition device 171. Therefore, instead of calculating an uncorrected impedance (for example, "Zload1 uncorrected"), the present calibration method reads the uncorrected impedance or phase value directly off the LCR Data Acquisition device.

The remainder of the calibration parameters (i.e., Zgain, Phasegain, Zoffset, and Phaseoffset) are then determined in the same fashion and steps as described previously in steps 301-312.

Accordingly, for the LCR data acquisition circuit 125 embodiment with a grounded shield 90 (FIG. 1C), the calibration parameter storage 204 is provided with the calibration parameter values (309.1d) through (309.5d) below when a variation of the steps corresponding to the steps 301 through 312 are performed.

(309.1d) Cabling capacitance to ground, Ccable (i.e., the capacitance between grounded shield 90 and the corresponding center wire 80 surrounded by the shield 90), wherein Ccable is dependent on the length of the cabling 78a,b for the channel being calibrated, (309.2d) Zgain, (309.3d) Zoffset, (309.4d) Phasegain, and (309.5d) Phaseoffset, wherein each term identified here has the same meaning as the (any) corresponding identical term used in describing FIGS. 4A through 4D hereinabove.

Accordingly, during operation of the moisture measurement system 10 configured as an LCR data acquisition circuit with a grounded shield 90, for each channel, the following steps are performed:

(Step D-1) The impedance load Z4 (e.g., for the lumber 110 or 120) is measured by the LCR data acquisition card 171. The impedance Z4 is transmitted to the calibration component 205.

(Step D-2) The impedance load is broken into its parallel reactive and resistive components, Cload(uncorrected) and Rload(uncorrected) in the calibration component 205.

(Step D-3) The cable capacitance (Ccable) from the calibration storage 204 is subtracted from Cload(uncorrected) in the calibration component 205. This provides a new value denoted Cload(uncorrected)$_1$ herein which is performed in the calibration component 205.

(Step D-4) The values Cload(uncorrected)$_1$ and Rload(uncorrected) are then combined to specify a new impedance value Zload(uncorrected)$_1$ that has the cable capacitance removed from it.

(Step D-5) An (uncorrected) phase of the load is then calculated by the calibration component 205.

(Step D-6) The calibration parameters (gains and offsets) in the calibration parameter storage 204 (i.e., identified in (309.1d) through (309.5d) above) are used, by the calibration component 205, to remove errors generated by electrical components other than the capacitor 17 by performing corrections to the total impedance and phase. Equations to perform these corrections are: which is performed in the calibration component 205.

$$Zload(corrected) = Zload(uncorrected)_1 * Zgain + Zoffset, \quad (a)$$

and $$Phaseload(corrected) = Phaseload(uncorrected) * Phasegain + Phaseoffset. \quad (b)$$

(Step D-7) With accurate determination of the phase angle and total impedance of the load, the impedance is resolved into rectangular components, i.e., the parallel impedances Cload and Rload, as one of ordinary skill in the art will understand which is performed in the calibration component 205.

(Step D-8) The impedances Cload and Rload are provided to the kiln moisture analysis 210 (FIG. 1C) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(2) Impedance Measurement (IM) Calibration Method

The impedance measurement calibration method uses a high precision LCR meter or impedance bridge (not shown in the figures) together with the steps described in the flowchart of FIGS. 5A and 5B (described hereinbelow) to determine calibration parameters for the moisture measurement system 10 embodiments such as those of FIG. 1A. Impedance bridges and LCR meters (hereafter referred to commonly as an "LCR meter") are used to determine inductance, capacitance, and resistance values in a circuit, as one of ordinary skill in the art will understand. In particular, such LCR meters are generally used to measure the impedance parameters of a circuit. In one embodiment, the high precision LCR meter may be the BK Precision LCR meter, model 879, manufactured by BK Precision, 22820 Savi Ranch Parkway, Yorba Linda, CA 92887. This second calibration method uses the measurements of such a LCR meter to read the various impedances of the coaxial cables 78a,b (and intervening electrical components) for each channel. For each channel, the corresponding impedances are then factored into a circuit model as shown in any one of the FIGS. 3A, 3B, or 3C. Such factoring is used to determine the calibration parameters that can, in turn, be used for "normalizing" the channel so that signal characteristics generated by the cabling 78a,b (and any intervening electronics) between the computer 160 and the channel's capacitor 17 are removed or made substantially uniform regardless of the length of such cabling.

(2.1) IM Calibration Method for Voltage Divider Circuit with Excited Shield (FIGS. 1A and 3A) and Grounded Shield (FIGS. 1A and 3B)

For example, the impedance measurement calibration method may be used in the case of an electrically excited shield 90 and according to the circuit model 204 of FIG. 3A. Upon starting the calibration process, neither Rterm nor Ccable (FIG. 3A) are known. Using the LCR meter, both values can be accurately measured. The parallel combination of Rterm and Ccable then form the terminal impedance, Zterm. Zterm for each channel can then be entered in the same type of calibration file DF, or calibration parameter storage 204 as described earlier, and the gains can be assumed to be 1, while the offsets can be assumed to be 0, since the critical parameter of interest is the terminal impedance, and the gains are typically near unity, and the offsets are typically near zero. In other words, the impedance measurement calibration method is a simplified method that relies primarily on accuracy in determining the terminal impedance, and the gains and offsets are judged to be small enough to be insignificant.

In the case of a grounded shield 90, the circuit model shown in FIG. 3B can be used. Thus, upon starting the calibration process, neither Rterm nor Ccable are known. However, using the LCR meter, both values can be accurately measured. Thus, Rterm is entered as Zterm, and Ccable is recorded so it can be subtracted from each subsequent capacitance measurement. The values Zterm and Ccable can then be entered in the same type of calibration file DF, or calibration parameter storage 204 as described above, and the gains can be assumed to be 1, while the offsets can be assumed to be 0.

As shown above, the impedance measurement calibration method is suitable for a circuit model involving either an electrically excited coaxial shield 90, or a grounded coaxial shield 90. Moreover, the impedance measurement calibration method offers an advantage over the above described resistor-capacitor network calibration methods in that all tasks of the impedance measurement calibration method can be performed by an operator in a control room where the range in temperature is, e.g., 65° to 75° F., and with humidity below, e.g., 20%. In particular, the impedance measurement calibration method does not require an operator to connect a calibration box 704 at the end of the coaxial cable 78b in the kiln 15 which may be a considerable distance from the control room (e.g., up to 1000 linear feet or more).

A description of the steps of FIGS. 5A and 5B follows. In step 401 of FIG. 5A, once a channel is selected, the coaxial cable 78a and corresponding cable 78b for the channel (e.g., FIG. 1A) are detached from the sensor measurement unit 190 and/or the computer 160 in the control room. Additionally, the cables are detached from the capacitor 17 of the channel. In step 402, one input lead on the LCR meter is attached to the coaxial shield 90 of the channel's cable 78a, and the other LCR meter lead is attached to the channel's coaxial center wire 80 of the cable 78a. Using the LCR meter to measure the capacitance, the capacitance (Ccable) between the center wire 80 and shield wire 90 is then measured along the total length (or at least 95% of the length) of the cables 78a and 78b to obtain a total cable capacitance (step 403). For example, if the combined length of cables 78a and 78b is about 200 ft, a typical Ccable measurement for the length of cable would be about 3500 pF, since the capacitance between the shield and the center wire is roughly 17.5 pF/linear ft for at least some types of coaxial cable.

In step 404 of FIG. 5A a determination is made as to whether the cabling shield 90 is electrically excited or grounded. In the case of a grounded shield 90, the capacitance for the cables 78a,b (i.e., the value of "Ccable" determined in step 403) can then be simply entered into the calibration file DF, or the calibration parameter storage 204 as one of the calibration parameters as indicated in step 406.

In the case of an excited shield 90 (i.e., FIG. 1A), step 408 is performed, wherein the terminal impedance ($Zterm_0$) between the leads of the LCR meter must be calculated as follows:

$$Zterm_0 = [-i/(2\pi \ast f \ast Ccable) \ast Rload]/[-i/(2\pi \ast f \ast Ccable) + Rload] \quad \text{(Equation H)}$$

where:
$Zterm_0$ is the complex representation of the load impedance between the leads of the LCR meter,
$\pi = 3.14159$ (approx.),
f=frequency of the excitation signal for exciting the shield,
Ccable=measured cable capacitance for the channel cables 78a and 78b,
"i" identifies the imaginary terms of Equation H, and
Rload is the resistance value of the load resistor 140. Note that Rload may be known from a previous resistance measure of the load resistor 140.

Subsequently, in steps 410 and 412, all the gains (i.e., the impedance gain (Zgain), and the phase gain (Phasegain)) are simply set to 1, and all the offsets (i.e., the impedance offset (Zoffset), and the phase offset (Phaseoffset)) are simply set to 0. Depending on whether the shield 90 is excited or grounded (step 416), a respective one of the steps 420 and 424 is performed, wherein the data file DF, or the calibration parameter storage 204 (or another data container such as a relational database) for the channel is populated as shown in FIG. 5B. That is, at the completion of the steps of FIGS. 5A and 5B, the following calibration parameter values are stored for the excited shield embodiment:
(420.1a) $Zterm_0$,
(420.2a) Zgain=1,
(420.3a) Zoffset=0,
(420.4a) Phasegain=1, and
(420.5a) Phaseoffset=0.

Of course the steps 401 through 424 may be iteratively performed for each channel.

Alternatively, for the case where the shield 90 is grounded (i.e., FIG. 1A), the following calibration parameter values are stored:
(420.1b) Zterm, which, indicated above, is approximated by Rterm since the shield 90 is grounded.
(420.2b) Ccable, wherein Ccable is dependent on the length of the cabling 78a,b for the channel being calibrated,
(420.3b) Zgain=1,
(420.4b) Zoffset=0,
(420.5b) Phasegain =1, and
(420.6b) Phaseoffset =0.

Note that the calibration parameters whose values are determined with the impedance measurement calibration method for the two voltage divider circuit embodiments are the same calibration parameters whose values are also determined with the resistor-capacitor network calibration method. Accordingly, these two calibration methods can be used interchangeably or together within the moisture measurement system 10. For example, the corresponding parameter values from the calibration parameter set for the impedance measurement calibration method, and from the calibration parameter set for the resistor-capacitor network calibration method may be averaged, or combined in other ways to obtain more reliable calibration parameter values.

During operation of the moisture measurement system 10, the calibration parameters immediately above (i.e., (420.1a) through (420.5a), and/or (420.1b) through (420.6b)) are used to calibrate or adjust the signals obtained from their channel and capacitor 17 according to the following steps. Note that these steps are described in terms of $Zterm_0$ for an excited shield 90. However, for the grounded shield embodiment, $Zterm_0$ can be replaced with Zterm (approximated by Rterm) as described above.

(Step E-1) Since $Zterm_0$ defines the impedance across the terminals of the amplifiers 145 (FIG. 1A), a voltage V1 is applied to excite the channel circuit (e.g., FIG. 3A or 3B).

(Step E-2) A differential voltage V1−V0 is measured across these amplifier terminals 208, 212 (FIGS. 3A and 3B).

(Step E-3) Subsequently, a total (uncorrected) value of the channel circuit impedance (denoted "Zload(uncorrected)" herein) is determined by the equation:

$$Zload(uncorrected) = Zterm_0 \ast (V0)/(V1-V0).$$

(Step E-4) Then, a corrected value for circuit impedance (denoted "Zload(corrected)" herein) is calculated, wherein at least the impedance induced by the channel cabling 78a,b is substantially factored out or made independent of the length of the cabling. In particular, Zload (corrected) is determined by applying the Zgain and Zoffset values in the data file DF, or the calibration parameter storage 204. That is, $$Zload(corrected) = [Zload(uncorrected) \ast Zgain] + Zoffset.$$

Note that since the gains and offsets are typically set to 1 and 0, respectively, the Zload(corrected) is equal to the Zload(uncorrected).

(Step E-5) Additionally, a value for the total signal phase (denoted "Phaseload(uncorrected)" herein) for the channel circuit is determined through application of one of the following methods: a trigonometric method, a Fourier transform method, a zero crossing method, etc, as one of ordinary skill in the art will understand.

(Step E-6) Subsequently, a corrected value for the phase of the circuit signals (denoted "Phaseload(corrected)" herein) is calculated by applying the Phasegain and Phaseoffset from the data file DF. That is, Phaseload(corrected)=[Phaseload(uncorrected)*Phasegain]+Phaseoffset.

Note that since the gains and offsets are typically set to 1 and 0, respectively, the Phaseload(corrected) is equal to the Phaseload(uncorrected).

(Step E-7) With accurate determination of the phase angle (i.e., Phaseload(corrected)) and total impedance of the load (i.e., Zload(corrected)), the impedance can be resolved into rectangular components, i.e., the parallel impedances Cload and Rload, as one of ordinary skill in the art will understand. Note that for the grounded shield configuration, Ccable is subtracted from Cload to obtain a new value for Cload which is then used in the following step.

(Step E-8) Since Cload and Rload are substantially independent of the length of the cabling 78a,b, the moisture content of the lumber being monitored (e.g., lumber stack 110 or 120) can be more accurately determined. Accordingly, the impedances Cload and Rload are provided to the kiln moisture analysis 210 (FIG. 1A) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(2.2) IM Calibration Method for Bridge Circuit Embodiment (FIG. 1B) with Grounded Shield Note that for the bridge metering embodiment of FIG. 1B where the shield(s) 90 is grounded, for each of the channels (between a corresponding one of the capacitors 17 and the computer 160), the calibration of the channel using the impedance measurement calibration method for the grounded shield(s) is modeled by the circuit model 218 in FIG. 3C. In the bridge metering embodiment, the terminal impedance (Zterm) is not of critical interest, since the impedance of the lumber is determined by balancing the bridge and does not rely on the value of terminal impedance. However, Ccable remains of critical interest and must be accounted for. Accordingly, for the bridge metering embodiment with a grounded shield 90 (FIG. 1B), the calibration parameter storage 204 is provided with the calibration parameter values (420.1c) through (420.5c) below when a variation of the steps corresponding to the steps 401 through 424 of FIGS. 5A and 5B are performed for a ground shield 90.

(420.1c) Cabling capacitance to ground, Ccable (i.e., the capacitance between grounded shield 90 and the corresponding center wire 80 surrounded by the shield 90), wherein Ccable is dependent on the length of the cabling 78a,b for the channel being calibrated, (420.2c) Zgain, (420.3c) Zoffset, (420.4c) Phasegain, and (420.5c) Phaseoffset, wherein each term identified here has the same meaning as the (any) corresponding identical term used in describing FIGS. 5A through 5B hereinabove.

Accordingly, during operation of the moisture measurement system 10 configured as in FIG. 1B (and modeled according to the circuit model of FIG. 3C) with a grounded shield 90, for each channel, the following steps are performed by the LCR data acquisition card 170:

(Step F-1) A null signal is transmitted to adjust impedance Z3 such that the bridge is balanced, i.e., such that the voltage across Z5 is maintained near zero volts.

(Step F-2) The value of the balancing impedance (Z3) is recorded by the data acquisition card 170.

(Step F-3) Z4 is then calculated according to the equation:

Z4=Z3*Z2/Z1.

The impedance Z4 is transmitted to the calibration component 205.

(Step F-4) Z4 is broken into its parallel reactive and resistive components, Cload(uncorrected) and Rload(uncorrected), respectively, by the calibration component 205.

(Step F-5) The cable capacitance (Ccable) is subtracted from the Cload(uncorrected) by the calibration component 205. This provides a new Cload(uncorrected)$_0$.

(Step F-6) The Cload(uncorrected)$_0$ and the Rload(uncorrected) are then combined by the calibration component 205 to specify a new Zload(uncorrected)$_0$ that has the cable capacitance removed from it.

(Step F-7) The calibration component 205 determines an uncorrected phase of the impedance load (e.g., for the lumber 110 or 120) by evaluation of the real and imaginary portions of the complex impedance Z4, i.e., by converting the rectangular components of Z4's resistance and reactance into polar coordinates, the phase can be readily determined.

(Step F-8) The calibration parameters (gains and offsets) stored above (i.e., in step 424) are used, by the calibration component 205, to remove errors generated by electrical components other than the capacitor 17 by performing corrections to the total impedance and phase. Equations to perform these corrections are:

Zload(corrected)=Zload(uncorrected)$_0$*Zgain+Zoffset,   a.

and

Phaseload(corrected)=Phaseload(uncorrected)*Phasegain+Phaseoffset.   b.

Note that since the gains (i.e., Zgain and Phasegain) and offsets (i.e., Zoffset and Phaseoffset) are typically set to 1 and 0, respectively, the Zload(corrected) is equal to the Zload(uncorrected), and the Phaseload(corrected) is equal to the Phaseload(uncorrected).

(Step F-9) With accurate determination of the phase angle and the total impedance of the load, the calibration component 205 resolves the impedance into rectangular components, e.g., the parallel impedances Cload and Rload, as one of ordinary skill in the art will understand.

(Step F-10) The impedances Cload and Rload are provided to the kiln moisture analysis 210 (FIG. 1B) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(2.3) IM Calibration Method for LCR Data Acquisition Circuit, Grounded Shield

Note that for an embodiment of the LCR data acquisition circuit of FIG. 1C where the shield(s) 90 is grounded, for each of the channels (between a corresponding one of the capacitors 17 and the computer 160), the calibration of the channel using the impedance measurement calibration method for the grounded shield(s) is modeled by the circuit model 218 in FIG. 3C. In the present LCR data acquisition circuit embodiment of FIG. 3C, the terminal impedance (Zterm) is a value internal to the LCR metering equipment, and its value has already been factored into the data acquisition card 171 outputs. Thus, Zterm does not need to be computed.

Accordingly, for the LCR data acquisition circuit embodiment with a grounded shield 90, the calibration parameter storage 204 is provided with the following calibration parameter values (420.1d) through (420.5d) below when a variation of the steps 401 through 424 of FIGS. 5A and 5B are performed.

(420.1d) Cabling capacitance to ground, Ccable (i.e., the capacitance between grounded shield 90 and the corresponding center wire 80 surrounded by the shield), wherein Ccable is dependent on the length of the cabling 78a,b for the channel being calibrated, (420.2d) Zgain, (420.3d) Zoffset, (420.4d) Phasegain, and (420.5d) Phaseoffset, wherein each term identified here has the same meaning as the (any) corresponding identical term used in describing FIGS. 5A through 5B hereinabove.

Accordingly, during operation of the moisture measurement system 10 configured as in FIG. 1C (and modeled according to the circuit model of FIG. 3C) with a grounded shield 90, for each channel, the following steps are performed by the LCR data acquisition card 171:

(Step G-1) Z4, the total impedance of the circuit model of FIG. 3C, is measured by the LCR data acquisition card 171. The impedance Z4 is transmitted to the calibration component 205.

(Step G-2) Z4 is broken into its parallel reactive and resistive components, Cload(uncorrected) and Rload(uncorrected), in the calibration component 205.

(Step G-3) The cable capacitance (Ccable) is subtracted from the Cload(uncorrected) in the calibration component 205. This provides a new Cload(uncorrected)$_0$.

(Step G-4) The Cload(uncorrected)$_0$ and the Rload(uncorrected) are then combined to specify a new Zload(uncorrected)' that has the cable capacitance removed from it.

(Step G-5) An (uncorrected) phase of the load is generated in the calibration component 205.

(Step G-6) The calibration parameters (gains and offsets) stored above (i.e., in step 424) are used, by the calibration component 205, to remove errors generated by electrical components other than the capacitor 17 by performing corrections to the total impedance and phase. Equations to perform these corrections are:

a. $Zload(corrected) = Zload(uncorrected)_0 * Zgain + Zoffset$, and b. $Phaseload(corrected) = Phaseload(uncorrected) * Phasegain + Phaseoffset$.

Note that since the gains (i.e., Zgain and Phasegain) and offsets (i.e., Zoffset and Phaseoffset) are typically set to 1 and 0, respectively, the Zload(corrected) is equal to the Zload(uncorrected), and the Phaseload(corrected) is equal to the Phaseload(uncorrected).

This step is also performed by the calibration component 205.

(Step G-7) With accurate determination of the phase angle and total impedance of the load, the impedance can be resolved into rectangular components, the parallel impedances Cload and Rload, as one of ordinary skill in the art will understand. This step is also performed by the calibration component 205.

(Step G-8) The impedances Cload and Rload are provided to the kiln moisture analysis 210 (FIG. 1C) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(3) "Short-open" (S-O) Calibration Method

Figure 6A:
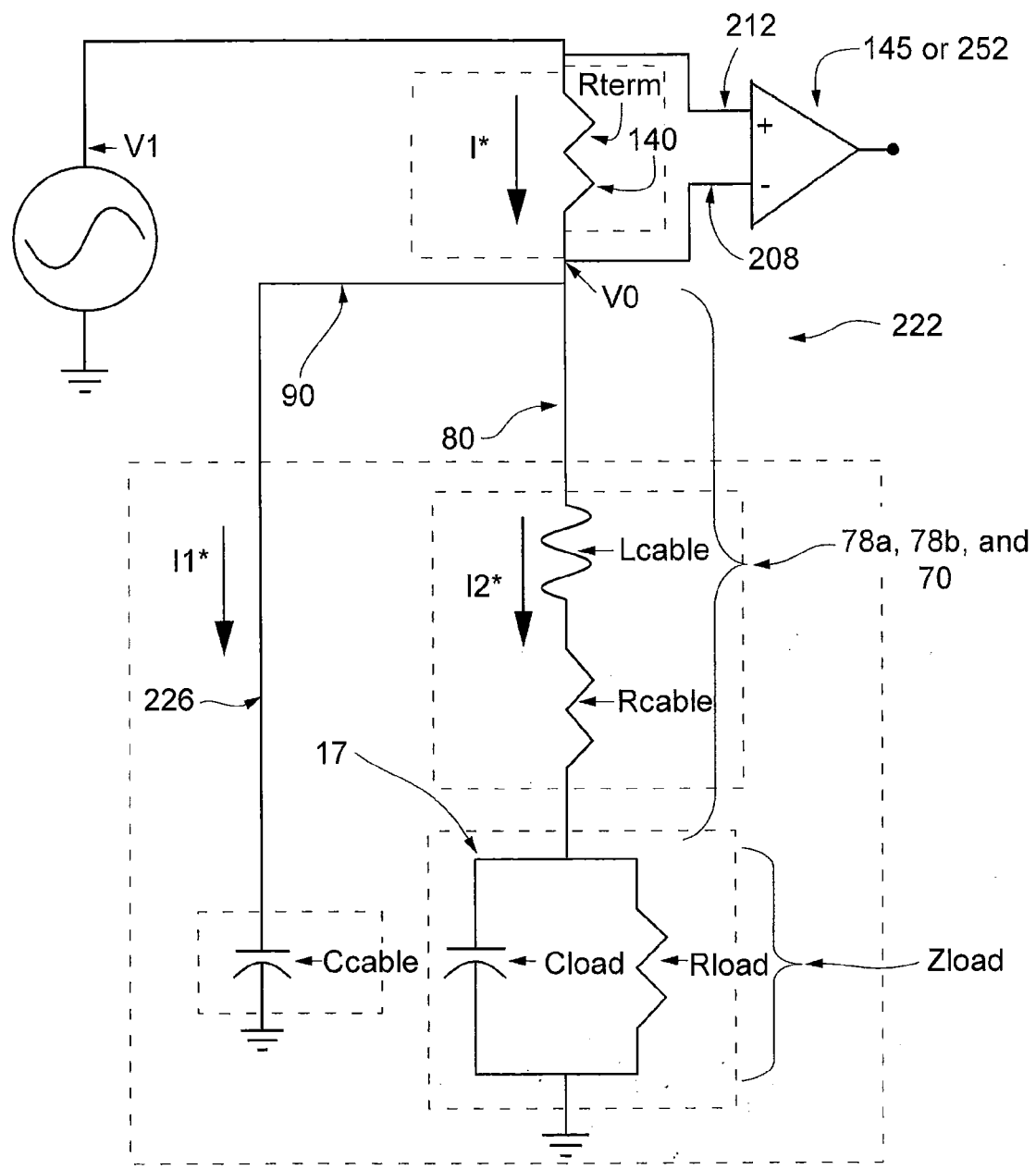
FIG. 6A is a schematic showing the circuit model for the "short-open" calibration method with a grounded coaxial shield.
Figure 6B:
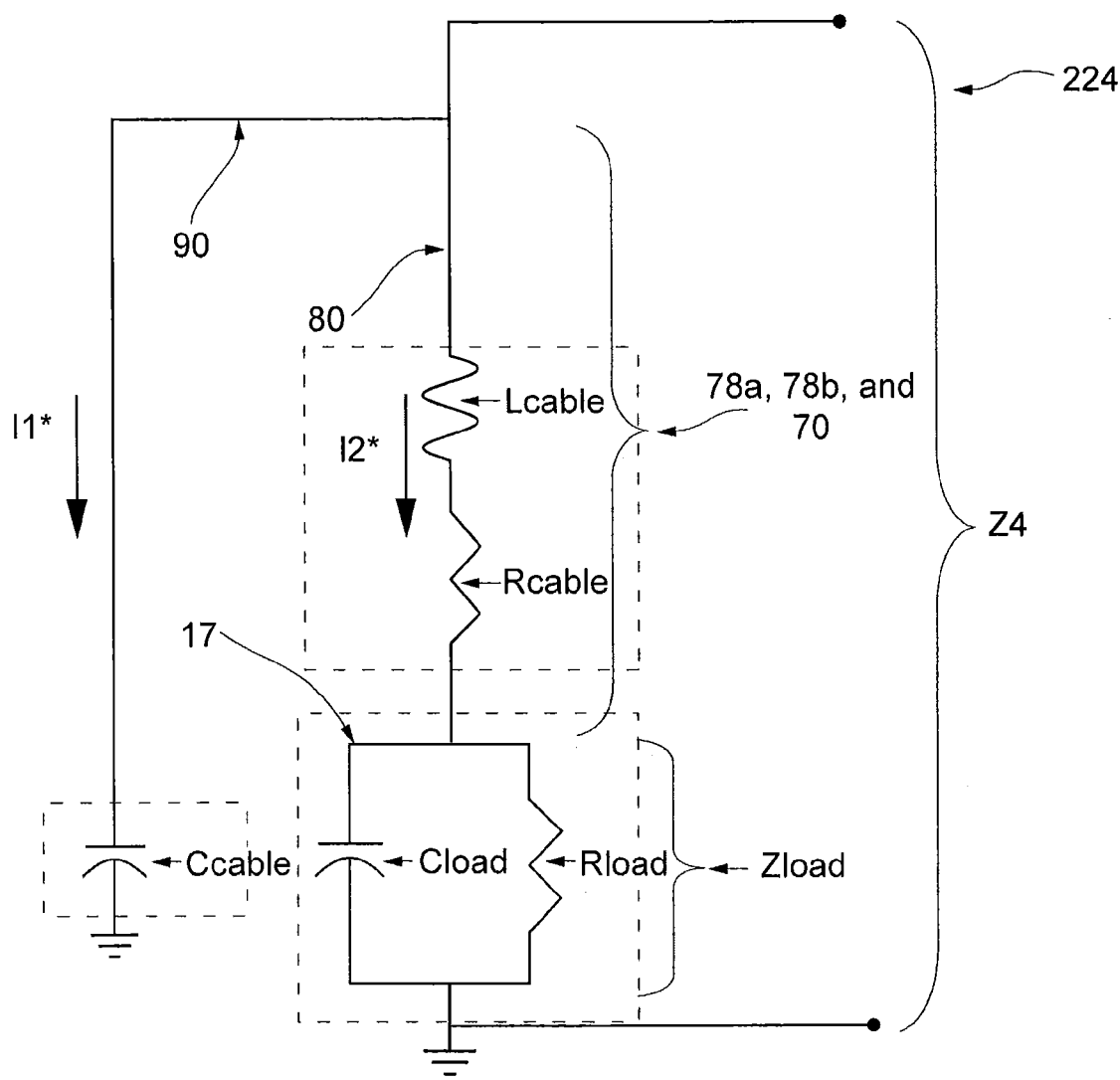
FIG. 6B is a schematic showing the circuit model for the "short-open" calibration method with a grounded coaxial shield, to be used in the LCR metering or bridge metering embodiments.
Figure 7B:
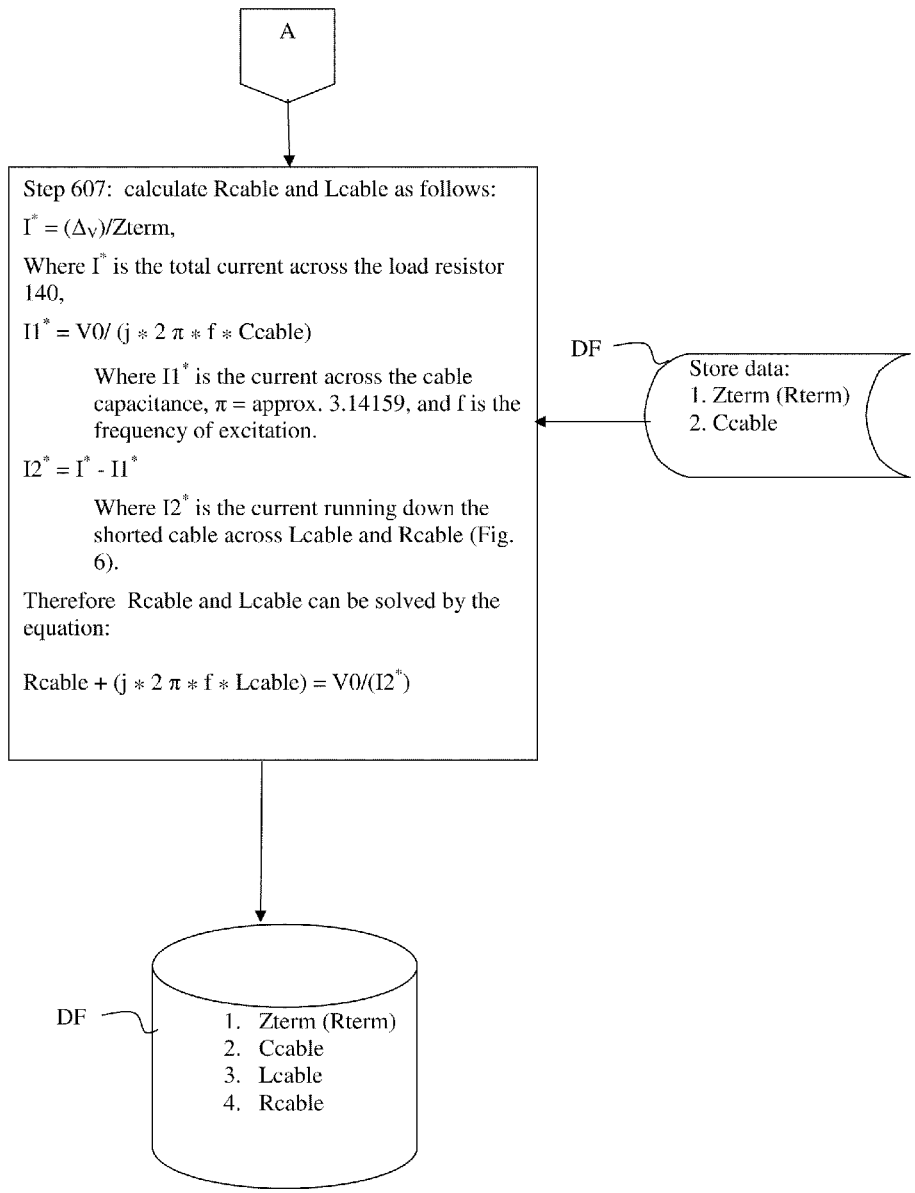

The third calibration method uses a "short-open" procedure as described in the flowchart of FIGS. 7A and 7B in reference to the circuit models of FIGS. 6A, and 6B. In particular, once a particular terminal impedance is measured, the "short-open" calibration method allows the moisture measurement system 10 itself to measure the various impedances of the coaxial cabling 78a,b for each channel. That is, for each channel, the cabling 78a,b for the channel is provided in a first configuration that electrically shorts the cabling, and in a second electrically open configuration. From measurements taken in each of the first and second configurations, the moisture measurement system 10 is capable of determining appropriate calibration parameter values for effectively cancelling, removing and/or ignoring electrical characteristics generated during signal transmission between the channel's capacitor 17, and the metering device (e.g., kiln moisture system 11 as in FIGS. 1A, 1B or 1C). Note that this "short-open" calibration method can only be used with a grounded shield 90, although it can be used in any of the three moisture measurement system 10 embodiments of FIGS. 1A, 1B, and 1C.

(3.1) S-O Calibration Method for Voltage Divider Circuit with Grounded shield (FIGS. 1A and 6A)

Referring now to the flowchart of FIGS. 7A and 7B, the steps are shown for determining the calibration parameters according to this third calibration method when applied to the voltage divider with grounded shield circuit embodiment of FIG. 1A. Accordingly, in step 601, a precision bridge (not provided in circuitry of FIGS. 1A and 6A) is used to accurately measure the terminal impedance (Zterm, as this term is described in the Description of Terms section) across the amplifier terminals (e.g., of amplifiers 145 of FIG. 1A), with no cabling 78a,b attached. The resulting value for Zterm should be approximately equal to the resistance of the load resistor 140 (Rterm) since no cables are attached. This value is then stored, e.g., to a data file DF, or calibration parameter storage 204. Upon installation of an embodiment of the moisture measurement system 10 at a kiln site, for each channel, its coaxial cabling 78a,b is attached to the metering device (e.g., kiln moisture system 11 as in FIG. 1A), and more particularly to the sensor measurement unit 190. For the circuit model 222 of FIG. 6A that is now completely formed, the voltage across the amplifiers, e.g., 145, is now measured in an "open" circuit condition. That is, in steps 602 and 603 of FIG. 7A, the channel cable 78b is disconnected from the capacitor 17 and placed on a non-conducting surface, and the voltage across the load resistor 140 (FIGS. 1A and 6A) is then measured. Since the cabling for the channel is disconnected from the capacitor 17, this effectively removes the bottom right leg (i.e., 80 and 17) of the circuit shown in FIG. 6A from providing a signal to the rest of the circuit. In other words, Lcable (the inductance of the cabling) and Rcable (the resistance of the cabling), as well as the impedance of the lumber (Zload) no longer provide a current path to the load resistor 140. Therefore, the only current path is the capacitance (Ccable) of the coaxial cable shield 90 to ground, which can then be calculated as described in step 604, and as follows:

a. Impedance load of the cabling (i.e., Zcable) is determined as $(Zterm*V0)/(V1-V0)$, wherein V1 is the generated voltage of the excitation signal, and V0 is the voltage of the excitation signal for the center wire 80 at the point indicated in FIG. 6A, and b. $Ccable=1/(2*\pi*f*Zcable)$, where $\pi$=approximately 3.14159, and f is the excitation frequency. Note that Ccable is dependent on the length of the channel cabling 78a,b.

Subsequently, the cable capacitance to ground (Ccable) is stored in, e.g., the data file DF, or the calibration parameter storage 204.

In step 605, the end of the cable 78b in the kiln is shorted, which can be done with a jumper cable from the coaxial center wire 80 to any grounded structure in the kiln 15, such as a ground lug on the kiln wall or the conduit through which the coaxial cabling 78b extends. The voltage across the load resistor 140 (Rterm) is then measured to obtain the "short" circuit reading, as described in step 606. In this shorted configuration, the impedance of the lumber Zload is then removed from the circuit (of FIG. 6A), and the only impedance remaining down the right leg of this circuit is the cable inductance, Lcable, and the cable resistance, Rcable as shown in FIG. 6A. Lcable and Rcable are then easily calculated as described in step 607, since all the other impedances in the circuit are now known.

Subsequently, the following calibration parameters are stored in, e.g., the calibration file DF, or the calibration parameter storage 204:

(607.1a) Zterm (Rterm),
 (607.2a) Ccable, wherein Ccable is dependent on the length of the cabling 78a,b for the channel being calibrated,
 (607.3a) Lcable, and
 (607.4a) Rcable.

Of course the steps 601 through 607 may be iteratively performed for each channel.

During operation of the moisture measurement system 10, the four calibration parameters immediately above are used to calibrate or adjust the signals from the channel and capacitor 17 as follows:

(Step H-1) Zterm (Rterm) is known (due to the described measurement of step 601), and the differential voltage V1−V0 can be measured with the amplifier 145.

(Step H-2) During the lumber moisture monitoring operation, I*, the total current across the load resistor 140, can be determined as follows:

$I*=(V1-V0)/Zterm$, (Step H-3) Since Ccable is known (as determined in calibration step 604), and since V0 is known, it is possible to determine the impedance of the left leg 226 of the circuit model of FIG. 6A as follows:

$ZCcable=1/(j*\omega*Ccable)$, where ZCcable is the impedance of the channel cabling 78a,b, j indicates that this impedance is reactive, and $\omega$ is the radial frequency of the excitation voltage.

(Step H-4) Accordingly, the current across the capacitance of the cabling of the left leg 226 is:

$I1*=V0/ZCcable$ (FIG. 6A).

(Step H-5) Since I* and I1* are now known, the current (I2*) running down the right circuit leg of FIG. 6A having Lcable, Rcable, and the capacitor 17 can be determined as follows:

$I2*=I*-I1*$.

(Step H-6) Further, since I2* is now known, V0 is known, and both Lcable and Rcable are retrieved from the calibration storage DF or 204, it is possible to calculate Zload* (i.e., the total impedance of the capacitor 17 formed in the kiln stack) as follows. Since $(Zload*+[j*\omega*Lcable]+Rcable)*I2*=V0$, upon rearrangement, the following equation is obtained for determining Zload*:

$Zload*=(V0/I2*)-[j*\omega*Lcable]-Rcable$.

(Step H-7) Resolve Zload* into its rectangular components, i.e., the parallel impedances Cload and Rload, as one of ordinary skill in the art will understand. The impedances Cload and Rload are provided to the kiln moisture analysis 210 (e.g., FIG. 1A) for determining the moisture content of the lumber in the kiln 15 corresponding to the channel.

The phase of the load of the capacitor 17 (denoted "PHASE" hereinbelow) can be determined by comparing the phase of the voltage at the load and the current at the load, using any of a variety of methods including trigonometric methods, zero crossing method, Fourier transform, etc. as one of ordinary skill in the art will understand. It is then straightforward to resolve the impedance into rectangular components, the parallel impedances Cload and Rload, as one of ordinary skill in the art will understand.

(3.2) S-O Calibration Method for Bridge Circuit with Grounded Shield (FIG. 1B)

Note that for an embodiment of the bridge circuit of FIG. 1B where the shield(s) 90 is grounded, for each of the channels (between a corresponding one of the capacitors 17 and the computer 160), the calibration of the channel using the Short-Open calibration method for the grounded shield(s) is modeled by the circuit model 224 in FIG. 6B. In the present bridge circuit embodiment of FIG. 1B, the terminal impedance (Zterm) is not of critical interest. However, Ccable, Lcable, and Rcable remain of critical interest and must be determined. Note that neither FIG. 1B nor FIG. 6B provide measurements of the voltages V1 and V0 as described in section 3.1 above. Instead, the impedance Z4 (FIGS. 1B and 6B) is determined by balancing the bridge in various steps of the short and open procedure. In particular, in the open configuration, by balancing the bridge circuit 125 (FIG. 1B), Z4 is approximately equal to the impedance provided by Ccable.

In the short configuration, Z4 is also obtained by balancing the bridge circuit 125 (FIG. 1B), wherein Z4 is approximately equal to the parallel combination of (a) the impedance provided by Rcable and Lcable, and (b) the impedance provided by Ccable. Accordingly, Rcable and Lcable can be readily determined by decomposing the complex impedance Z4 into its real and imaginary components, as one of ordinary skill in the art will understand.

Accordingly, for the bridge metering embodiment with a grounded shield 90, the calibration parameter storage 204 is provided with the calibration parameter values (607.1b) through (607.3b) following when the steps of FIGS. 7A and 7B are performed.

(607.1b) Ccable (i.e., Z4 in the open configuration), wherein Ccable is dependent on the length of the cabling 78$a,b$ for the channel being calibrated, 607.2b) Lcable, and (607.3b) Rcable, wherein each term identified here has the same meaning as the (any) corresponding identical term used in describing FIGS. 7A through 7B hereinabove.

During operation of the moisture measurement system 10, the three calibration parameters immediately above are used to calibrate or adjust the signals from the channel and capacitor 17 as follows:

(Step I-1) A null signal is transmitted to adjust impedance Z3 such that the bridge is balanced, i.e., such that the voltage across Z5 is maintained near zero volts.

(Step I-2) The value of the balancing impedance (Z3) is recorded by the data acquisition card 170.

(Step I-3) Z4 is then calculated according to the equation: Z4=Z3*Z2/Z1. The impedance Z4 is transmitted to the calibration component 205.

(Step I-4) Z4 is broken into its parallel reactive and resistive components, Cload(uncorrected) and Rload(uncorrected), respectively, in the calibration component 205.

(Step I-5) The cable capacitance (Ccable) stored in DF or the calibration parameter storage 204 is subtracted from the Cload(uncorrected) by the calibration component 205. This provides a new corrected Cload, denoted Cload(corrected).

(Step I-6) The cable resistance (Rcable) and inductance (Lcable) are subtracted from the Rload(uncorrected) by the calibration component 205. This provides a new corrected Rload (denoted Rload(corrected)), which is a complex number.

(Step I-7) The Cload(corrected) and the Rload(corrected) are then combined, by the calibration component 205, to specify Zload* that has the cable 78$a,b$ capacitance, inductance, and resistance removed from it. Note that Zload* is a complex number which can be readily broken down into rectangular components, i.e., the parallel impedances Cload and Rload, as one of ordinary skill in the art will understand.

(Step I-8) The impedances Cload and Rload are provided to the kiln moisture analysis 210 (FIG. 1B) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

(3.3) S-O Calibration Method for LCR Data Acquisition Circuit with Grounded Shield Note that for an embodiment of the LCR data acquisition of FIG. 1C where the shield(s) 90 is grounded, for each of the channels (between a corresponding one of the capacitors 17 and the computer 160), the calibration of the channel using the Short-Open calibration method is modeled by the circuit model 224 in FIG. 6B. In the present LCR metering embodiment, the terminal impedance (Zterm) is not of critical interest, since the terminal impedance is already factored into the LCR data acquisition card 171 outputs. However, Ccable, Lcable, and Rcable remain of critical interest and must be accounted for.

In the open configuration, Z4 is approximately equal to the impedance provided by Ccable, and in the short configuration Z4 is approximately equal to the parallel combination of (a) the impedance provided by Rcable and Lcable, and (b) the impedance provided by Ccable. Moreover, each of Rcable and Lcable can be readily determined by decomposing the complex impedance Z4 (in the short configuration) into its real and imaginary components, as one of ordinary skill in the art will understand. Accordingly, for the present LCR data acquisition circuit embodiment with a grounded shield 90, the calibration parameter storage 204 is provided with the following calibration parameter values (607.1c) through 607.3c) when the steps of FIGS. 7A and 7B are performed:

(607.1c) Ccable (i.e., Z4 in the open configuration), wherein Ccable is dependent on the length of the cabling 78$a,b$ for the channel being calibrated, (607.2c) Lcable, and (607.3c) Rcable, wherein each term identified here has the same meaning as the (any) corresponding identical term used in describing FIGS. 7A through 7B hereinabove.

During operation of the moisture measurement system 10, the three calibration parameters immediately above are used to calibrate or adjust the signals from the channel and capacitor 17 as follows:

(Step J-1) The value of the complex impedance Z4 of the circuit model 224 is determined and recorded by the LCR data acquisition card 171. The impedance Z4 is transmitted to the calibration component 205.

(Step J-2) Z4 is broken into its parallel reactive and resistive components, Cload(uncorrected) and Rload(uncorrected) in the calibration component 205.

(Step J-3) The cable capacitance (Ccable) stored in DF or the calibration parameter storage 204 is subtracted from Cload(uncorrected) in the calibration component 205. This provides a new corrected Cload, denoted Cload(corrected).

(Step J-4) The cable resistance (Rcable) and inductance (Lcable) are subtracted from the Rload(uncorrected) in the calibration component 205. This provides a new corrected Rload (denoted Rload(corrected)), which is a complex number.

(Step J-5) The Cload(corrected) and the Rload(corrected) are then combined, by the calibration component 205, to specify a new value of Z4 (denoted Z4(corrected)) that has the cable 78$a,b$ capacitance, inductance, and resistance removed from it.

(Step J-6) The phase of the impedance load (e.g., lumber 110 or 120) is determined in the calibration component 205 by conversion of the real and imaginary representation of the complex impedance Z4(corrected) into polar coordinates, i.e., by converting the rectangular components of Z4(corrected)'s resistance and reactance into polar coordinates, the magnitude of Z4(corrected) and the corresponding phase angle for Z4(corrected) are determined.

(Step J-7) With accurate determination of the phase angle (Step J-6) and the total impedance Z4(corrected) of the kiln lumber stack, resolution of the impedance Z4(corrected) into rectangular, i.e., the parallel impedances Cload and Rload, components can be performed by the calibration component 205, as one of ordinary skill in the art will understand.

(Step J-8) The impedances Cload and Rload are provided to the kiln moisture analysis 210 (FIG. 1C) for determining the moisture content of the lumber in the kiln 15 corresponding to the channel. In one embodiment, the moisture analysis component 210 translates the impedance data into moisture content. The translation from capacitance to moisture content is facilitated via a moisture data table 220 which includes capacitance-moisture correspondences. The moisture content is then displayed on a user interface 230 and transmitted via a serial communication device 240 to the kiln controller 250, which uses the moisture level to control, e.g., the kiln temperature, kiln dampers, and when to shut down the kiln lumber drying process.

The use of any of the aforementioned calibration methods ensures a response from each of the channels that does not depend (or not substantially so) on the length of the channel's cabling. Additionally, no "tuning" is required for the moisture measurement system 10 to accurately determine the capacitance induced by moisture in the kiln dried lumber. That is, no "tuning" is required wherein physical adjustments (e.g., extra electronics, changes in cable lengths, etc.) to the various channels is required in order to make each channel appear to have an output independent of channel cabling length.

Additionally, note that the various sets of steps disclosed above for using calibration parameter values (in order to adjust or correct measurements of signals from the capacitor(s) 17 so that portions of such measurements related to cabling 87a,b length is at least reduced) may be performed by software or firmware. Alternatively, such sets of steps may be performed via a hardware implementation as one of ordinary skill in the art will understand.

Moreover, it is within the scope of the present disclosure that the disclosed steps for obtaining values for the calibration parameters, and/or for adjusting or correcting the signal measurements from a capacitor(s) 17 so that there is a reduced a dependency on a length of cabling 78a,b should not be interpreted so narrowly that the entire length of the cabling 78a,b must be used. In particular, it is within the scope of the present disclosure that a particular length of cabling could be calibrated for use that may not include the entire length of the cable in use. For example, in some embodiments, calibration that compensates for a majority of the length of installed cabling (e.g., from the multiplexer 70 to the plates of a capacitor 17) may be effective without performing the calibration on, e.g., a short length of cabling between the kiln moisture system 11 and the multiplexer. In some embodiments, it is believed that calibrating for at least approximately 90% of the entire cabling 78a,b length is effective for appropriately estimating moisture content values in the drying lumber Additionally, if some portion of the cabling 78a,b has a trivial total capacitance regardless of the cause, then the length of this portion of the cabling 78a,b may not be used in determining the calibration parameter values, and/or in adjusting capacitor 17 signal measurements to reduce cabling 78a,b length dependencies.

Additionally, the present disclosure should not be interpreted so narrowly that the entire length of the cabling 78a,b must be coaxial cable rather than another type of cabling. For example, in some embodiments, small lengths of regular conducting wire may be substituted for coaxial cable without substantially impacting the lumber moisture content determining methods disclosed herein. For instance, a short section of stainless steel wire rope or standard copper wire may be attached between the plate of a capacitor 17, and the coaxial center wire without substantially impacting the effectiveness of the calibration parameters, and without substantially impacting the effectiveness of the adjusting/correcting of the signal measurements from a capacitor(s) 17 so that there is a reduced a dependency on the length of the cabling 78a,b.

While various embodiments of the present invention have been described in detail, modifications and adaptations of these embodiments will occur to those skilled in the art. It is to be expressly understood, however, that such modifications and adaptations are within the scope of the present invention, as set forth in the following claims. In particular, the calibration methods disclosed hereinabove can be employed in a variety of moisture measurement system 10 embodiments, including but limited to a voltage divider circuit, a bridge circuit, or an LCR data acquisition circuit.

What is claimed is:

1. A method for determining a moisture content of lumber drying, wherein signals transmitted from a sensor are used to determine the lumber moisture content, comprising:
    first obtaining cabling for signal communication between (1) and (2) following:
    (1) a sensor for providing signals related to a capacitance of a stack of drying lumber when the sensor is embedded therein, and
    (2) a data acquisition device for receiving the signals from the sensor in response to an excitation signal provided to the sensor via the cabling, and determining a measurement related to the lumber moisture content from the signals received;
    wherein the cabling includes a conductor, and a conductive shielding surrounding the conductor;
    configuring the cabling in each of one or more circuit configurations so that in each circuit configuration at least one end of the cabling is: not operatively connected to the sensor, and not operatively connected to the data acquisition device;
    second obtaining, for each circuit configuration of the one or more circuit configurations, one or more calibration values, including performing at least one of the following first and second sets of substeps:
    (a) the first set of substeps including (a-1) and (a-2) following:
        (a-1) providing, for the circuit configuration, corresponding impedance data for a predetermined impedance load applied to the cabling; and
        (a-2) obtaining at least one of the calibration values, by determining an impedance including a parallel combination of: (i) a capacitance between the conductor and the shielding, and (ii) a resistance between the conductor and the shielding, wherein the shielding is excited;

(b) the second set of one or more substeps, including the step:
  (b-1) obtaining at least one of the calibration values, CV, by determining a capacitance between the conductor and the shielding of the cabling, wherein the shielding is grounded, and the capacitance is dependent on a length of the cabling;
    wherein for an operative circuit configuration, CC, that varies from the circuit configuration by each end of the cabling being operatively connected to one of the sensor and the data acquisition device, and the operative circuit configuration CC includes the drying lumber, the at least one calibration value CV, for modifying values for the signals, is determined according to the operative circuit configuration being modeled as a voltage divider circuit;
storing the calibration values;
after the second obtaining step, a step of operably connecting the cabling for communicating between the sensor, and the data acquisition device to thereby provide an operable circuit configuration, including the drying lumber, which is identical to the operative circuit configuration CC of step (b-1) above when the second set of steps is performed;
monitoring a moisture content of the drying lumber using the operable circuit configuration, including the substeps of:
  (c-1) applying the excitation signal to the conductor of the cabling;
  (c-2) determining one or more impedance related measurements of a circuit including the cabling, the sensor, and the drying lumber, wherein the at least one end of the cabling is operatively connected to one of the sensor, and the data acquisition device;
  (c-3) obtaining one or more enhanced impedance related values that are substantially independent of an impedance related to at least one length of the cabling, wherein at least one of the one or more enhanced impedance related values is determined as a function of a combination of: (i) one of the impedance related measurements, and (ii) the at least one calibration value from one of (a-2) and (b-1) above; and
  (c-4) using the one or more enhanced impedance related values for estimating the moisture content of the drying lumber.

2. The method of claim 1, wherein the cabling includes one or more cables whose combined length is greater than 50 feet in length.

3. The method of claim 1, wherein the cabling includes one or more cables whose combined length is between 100 feet and 1000 feet in length.

4. The method of claim 1, wherein the second set of steps is performed, and the length of the cabling of (b-1), and the at least one length of the cabling of (c-3) are substantially a same portion of the cabling.

5. The method of claim 1, wherein the step (c-2) includes obtaining a time series of the impedance related measurements, and the stored calibration values used in the step of obtaining (c-3) do not change in a time period for receiving the time series of the impedance related measurements.

6. The apparatus of claim 5, wherein the time period includes one or more days.

7. The method of claim 1, wherein for at least one sequential performance of the steps (c-1), (c-2), and (c-3), the step of configuring is not performed during the sequential performance.

8. The method of claim 1, wherein the step of obtaining (c-3) includes determining a value that varies inversely with one of: (i) a difference between two voltages of the impedance related measurements, each of the two voltages being for the conductor at points having a load resistor therebetween; and (ii) one of the calibration values indicative of a terminal impedance.

9. The method of claim 1, wherein the configuring step includes providing at least one of the one or more circuit configurations by operably connecting at least one length of the cabling to a signal measurement device excluded from the operable circuit configuration for obtaining the impedance related measurements.

10. A method for determining parameters used in estimating a moisture content of lumber drying, wherein signals transmitted, via cabling, from a sensor, are used to determine the lumber moisture content, comprising:
  providing one or more values for a plurality of calibration parameters, the one or more values including at least one of:
    (a) a first value indicative of a terminal impedance at terminals to which the cabling is connected, wherein a first of the terminals is connected to a conductor of the cabling, and a second of the terminals is connected to a shield of the cabling, the shield for shielding the conductor, and
    (b) a second value indicative of a capacitance of the cabling between the conductor and the shield along a length of the cabling;
  determining at least an additional one of the values for one of the parameters of the plurality of calibration parameters using at least one of the first value and the second value, wherein the additional value is the other of the first and second values, or the additional value is indicative of at least one of:
    (i) an impedance gain adjustment,
    (ii) an impedance offset adjustment,
    (iii) an impedance phase gain adjustment,
    (iv) an impedance phase offset adjustment,
    (v) an inductance of the cabling; and
    (vi) a resistance of the cabling;
  accessing the one or more values for the plurality of calibration parameters, wherein the one or more values are used to correct impedance values from a time series of the signals so that impedance values obtained from such correction are more indicative of the moisture content in the drying lumber.

11. An apparatus for determining a moisture content of lumber drying, wherein signals transmitted, via cabling, from a sensor, are used to determine the lumber moisture content, comprising:
  cabling for signal communication between: (i) a sensor for measuring a capacitance of a stack of drying lumber in which the sensor is embedded, and (ii) a data acquisition device for generating an excitation signal provided to the sensor via the cabling, wherein the cabling includes a conductor, and a conductive shielding surrounding the conductor;
  wherein the cabling, sensor, the drying lumber, and data acquisition device form an operative circuit configuration for estimating the moisture content of the drying lumber;
  a device for providing a predetermined impedance load to the cabling, wherein one end of the cabling is connected to the device, and the cabling is disconnected from at least one of the sensor, and the data acquisition device;

wherein, while the device is connected to the cabling, one or more values are obtained, including at least one of the following values of (a-1) and (a-2):
  (a-1) a first value indicative of a terminal impedance at terminals to which the cabling is connected, wherein a first of the terminals connects to the conductor, and a second of the terminals connects to the conductive shielding, the shield, and
  (a-2) a second value indicative of a capacitance along at least one length of the cabling between the conductor and the conductive shielding, wherein the second value is determined according to the operative circuit configuration being modeled as a voltage divider circuit;
wherein when the cabling is disconnected from the device and connected to the sensor and the data acquisition device to thereby provide a particular operable circuit configuration, the particular operable circuit including the at least one length of the cabling, the sensor, and the drying lumber, then the particular operable circuit configuration is operably identical to the operative circuit configuration for obtaining the second value;
wherein a moisture content of the drying lumber is monitored using in the operative circuit configuration, the monitoring resulting in (b-1), (b-2), and (b-3) following:
  (b-1) obtaining one or more measurements of the operative circuit configuration;
  (b-2) determining one or more impedance values that are less dependent upon an impedance for the cabling, and more indicative of an impedance for the drying lumber than the one or more measurements, wherein the one or more impedance values are determined using one of: (i) the first value, and a difference between two voltages of the one or more measurements, and (ii) the second value, and a difference between a capacitance of the one or more measurements; and
  (b-3) using the one or more impedance values for estimating the moisture content of the drying lumber.

* * * * *